US009688653B2

(12) United States Patent
Seed et al.

(10) Patent No.: US 9,688,653 B2
(45) Date of Patent: Jun. 27, 2017

(54) ETHOXYPHENYL THIENYL COMPOUNDS AND METHODS FOR THE TREATMENT OF BACTERIAL INFECTIONS

(71) Applicants: Duke University, Durham, NC (US); The University of Kansas, Lawrence, KS (US); Southern Research Institute, Birmingham, AL (US)

(72) Inventors: Patrick C. Seed, Durham, NC (US); Carlos C. Goller, Durham, NC (US); Steven Rogers, Dallas, TX (US); Brooks Maki, Las Vegas, NV (US); Frank Schoenen, Lawrence, KS (US); James Noah, Birmingham, AL (US); E. Lucile White, Birmingham, AL (US)

(73) Assignees: Duke University, Durham, NC (US); University of Kansas, Lawrence, KS (US); Southern Research Institute, Birmingham, AL (US)

(*) Notice: Subject to any disclaimer, the term of this patent is extended or adjusted under 35 U.S.C. 154(b) by 0 days.

(21) Appl. No.: 14/514,725

(22) Filed: Oct. 15, 2014

(65) Prior Publication Data

US 2015/0031658 A1    Jan. 29, 2015

Related U.S. Application Data

(63) Continuation-in-part of application No. 14/305,649, filed on Jun. 16, 2014, now Pat. No. 9,593,095.

(60) Provisional application No. 61/890,930, filed on Oct. 15, 2013.

(51) Int. Cl.
| | | |
|---|---|---|
| A61K 31/38 | (2006.01) | |
| C07D 333/24 | (2006.01) | |
| C07D 417/12 | (2006.01) | |
| A61K 31/4439 | (2006.01) | |
| A61K 31/43 | (2006.01) | |
| A61K 31/545 | (2006.01) | |
| A61K 31/381 | (2006.01) | |
| C07D 409/12 | (2006.01) | |
| C12Q 1/02 | (2006.01) | |

(52) U.S. Cl.
CPC ......... *C07D 333/24* (2013.01); *A61K 31/381* (2013.01); *A61K 31/43* (2013.01); *A61K 31/4439* (2013.01); *A61K 31/545* (2013.01); *C07D 409/12* (2013.01); *C07D 417/12* (2013.01); *C12Q 1/025* (2013.01)

(58) Field of Classification Search
CPC .................................................... A61K 31/381
USPC ....................................................... 514/447
See application file for complete search history.

(56) References Cited

U.S. PATENT DOCUMENTS

2007/0231406 A1* 10/2007 Bucalo ................. A61K 9/0095
424/617
2014/0371194 A1    12/2014 Seed et al.

FOREIGN PATENT DOCUMENTS

WO    2010029577    3/2010

OTHER PUBLICATIONS

PubChem CID 23602075, Dec. 12, 2007.*
(Continued)

*Primary Examiner* — Shengjun Wang
(74) *Attorney, Agent, or Firm* — Nathan P. Letts; Olive Law Group, PLLC

(57) ABSTRACT

This invention relates generally to the discovery of a method of inhibiting, preventing or treating bacterial infections. The invention also relates to a method of inhibiting bacterial capsule biogenesis.

19 Claims, 14 Drawing Sheets

(56) References Cited

OTHER PUBLICATIONS

Figure 1:
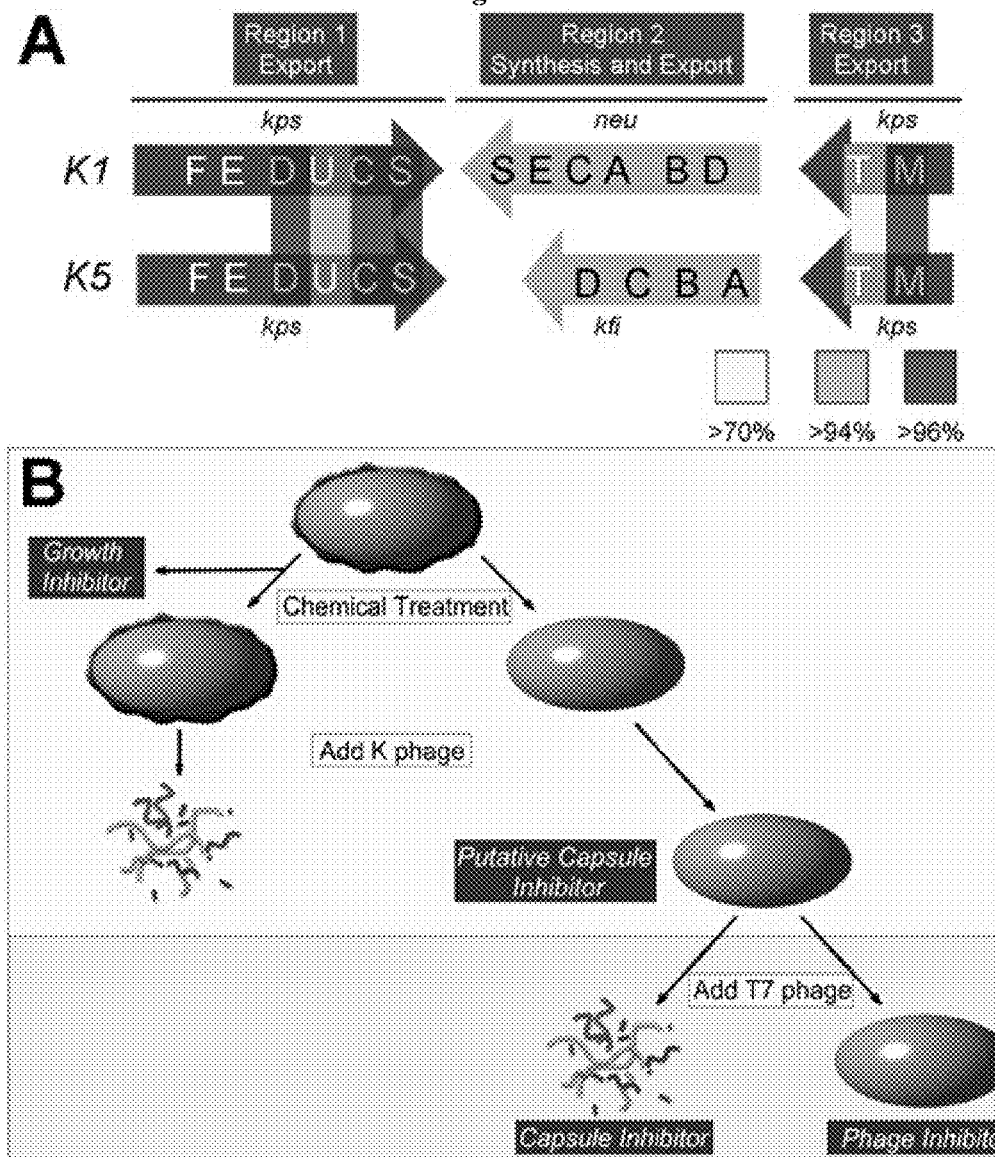

PubChem AID 488970, Oct. 29, 2010.*
PubChem AID 493020, Jan. 10, 2011.*
Goller et al. "High-Throughput identification of Chemical inhibitors of E. coli group 2 capsule biogenesis as anti-virulence agents," PLOS One, Jul. 2010, vol. 5, No. 7 e11642 pp. 1-10.*
Ali. A. S., Townes, C. L., Hall, J., and Pickard, R. S. "Maintaining a sterile uninary tract—the role of antimicrobial peptides". Jou of Urology 182:21-28 (2009).
Anderson, G. G., et al. "Intracellular bacterial biofilm-like pods in urinary tract infections." Science 301: 105-107. (2003).
Anderson, G. G., et al. "Polysaccharide capsule and sialic acid-mediated regulation promote biofilm-like intracellular bacterial communities during cystitis," Infect Immun 78: 963-975. (2010).
Bahrani-Mougeot, F. K., et al. "Type I fimbriae and extracellular polysaccharides are preeminent uropathogenic Escherichia coli virulence determinants in the murine urinmy tract." Molecular Microbology 45(4): 1079-1093. (2002).
Foxman, B "The epidemiology of urinary tract infection." Nature reviews Urology 7: 653-660(2010).
Goller, C. C., and Seed, P. C. "High-throughput identification of chemical inhibitors of E. coli Group 2 capsule biogenesis as anti-virulence agents." PLoS One 5, el1642.(2010).
Gopinathan, S., Nouraldeen, A., Wilson, A.G.E . "Development and application of a highthroughput formulation screening strategy for oral administration in drug discovery," Future Medicinal Chemistry 2: 1391-1398 (2010).
Gupta, K., Hooton, T. M., and Stamm, W. E. "Isolation of fluoroquinolone-resistant rectal · Escherichia coli after treatment of acute uncomplicated cystitis," J Antimicrob Chemother 56: 243-246. (2005).
Gupta, K., Scholes, D., and Stamm, W. E. "Increasing prevalence of antimicrobial resistance among uropathogens causing acute uncomplicated cystitis in women," JAMA 281: 736-738 (1999).
Hames, L., and Rice, C. E. "Antimicrobial resistance of urinary tract isolates in acute uncomplicated cystitis among college-aged women: choosing a first-line therapy," J Am Coll Health 56(2): 153-156.(2007).
Hillier S, Roberts Z, et al. "Prior antibiotics and risk of antibiotic-resistant community-acquired urinary tract infection: a case-control study." The Journal of Antimicrobial Chemotherapy 60: 92-99. (2007).
Hultgren, S. J., et al. "Role of type 1 pili and effects of phase variation on lower urinary tract infections produced by Escherichia coli" Infection and Immunity 50(2): 370-377.(1985).
Hultgren. S. J. "Uropathogenic Escherichia coli: interactions with bladder epithelium." Urology 57: 105-106.(2001).
Johnson, J. R. "Virulence factors in Escherichia coli urinary tract infection", Clin Microbial Rev4, 80-128. (1991).
Justice, S. S ., et al. "Filamentation by Escherichia coli subverts innate defenses during Urinary tract infection," Proc Natl Acad Sci U S A 103(52): 19884-19889. (2006).
Justice, S. S., "Maturation of intracellular Escherichia coli communities requires SurA," Infect Inunun 74: 4793-4800. (2006).
Kahlmeter, G. "The ECO.SENS Project: a prospective, multinational, multicentre epidemiological survey of the prevalence and antimicrobial susceptibility of urinary tract pathogens—interim report," J Antimicrob Chemother 46 Suppl 1, 15-22 (2000).
Karlowsky J. A., et al. "Fluoroquinolone-resistant urinary isolates of Escherichia coli from outpatients are frequently multidrug resistant: results from the North American Urinary Tract Infection Collaborative Alliance-Quinolone Resistance study," Antimicrob Agents Chemother 50: 2251-2254. (2006).
Wright, K.T., Seed, P. C., and Hultgren, S. J. "Development of intracellular bacterial communities of uropathogenic Escherichia coli depends on type 1 pili," Cell Microbial 9, 2230-2241. (2007).

Llobet, E., et al. "Capsule polysaccharicle is a bacterial decoy for antimicrobial peptides," Microbiology 154: 3877-3886. (2008).
Manges, A. R., et al. "Widespread distribution of urinary tract infections caused by a multidmg-resistant Escherichia coli clonal group," N Engl J Med 345: 1007-1013(2001).
Martinez, J. J., et al.."Type I pilus-mediated bacterial invasion of bladder epithelial cells." EMBO J 19: 2803-2812. (2000).
Mulvey, MA et al. "Establishment of a persistent Escherichia coli reservoir during the acute phase of a bladder infection," Infect Imnmn 69: 4572-4579 (2001).
Mushtaq, N., Redpath, et al. "Treatment of experimental Escherichia coli infection with recombinant bacteriophage-derived capsule depolymerase," J Antimicrob Chemother 56: 160-165. (2005).
Noah, J. W., et al. "A cell-based luminescence assay is effective for high-throughput screening of potential influenza antivirals." Antiviral Res 73: 50-59. (2007).
Olson, R. P., et al "Antibiotic resistance in urinary isolates of Escherichia coli from college women with urinary tract infections," Antimicrob Agents Chemother 53, 1285-1286. (2009).
Ploemen, J. H., et al. "Reversible conjugation of ethacrynic acid with glutathione and human glutathione S-transferase PI-1", Cancer Res 54, 915-919. (1994).
Roberts, I. S. "Bacterial polysaccharides in sickness and in health. The 1995 Fleming Lecture," Microbiology 141 (Pt 9), 2023-203 L (1995).
Roberts, I. S. "The biochemistry and genetics of capsular polysaccharide production in bacteria," Annu Rev Microbiol 50, 285-315. (1996).
Romagnoli, R., et al. "Synthesis and biological evaluation of 2-(3',4',5'-trimethoxybenzoyl)-3-amino 5-aryl thiophenes as a new class of tubulin inhibitors," J Med Chem 49, 6425-6428.(2006).
Rosen, D. A., et al. ."Detection of intracellular bacterial conummities in human urinmy tract infection," PLoS Med 4(12), e329. (2007).
Schappert, S. M. "National Ambulatory Medical Care Survey: 1991 summary," Vital Health Statistics 13, 1-110.(1994).
Smith PA and Romesberg FE. "Combating bacteria and drug resistance by inhibiting mechanisms of persistence and adaptation." Nature chemical biology 3: 549-556.(2007).
Spellberg B, Guidos R. et al. "The epidemic of antibiotic-resistant infections: a call to action for the medical community from the Infectious Diseases Society of America. Clinical infectious diseases", an official publication of the Infectious Diseases Society of America 46: 155-164.(2008).
Talan, D. A., et al. "Comparison of ciprofloxacin (7 days) and trimethoprim-sulfumethoxazole (14 days) for acute uncomplicated pyelonephritis pyelonephritis in women: a randomized Trial" JAMA 283(12): 1583-1590. (2000).
Vimr, E. R., Aaronson, W, and Silver, R. P. "Genetic analysis of chromosomal mutations in the polysialic acid gene cluster of Escherichia coli K1." J Bacterial 171(2): 1106-1117. (1989).
Warren, J. W., et al. "Guidelines for antimicrobial treatment of uncomplicated acute bacterial cystitis and acute pyelonephritis in women." Infectious Diseases Society of America (IDSA), Clin Infect Dis 29: 745-758.(1999).
PubChem AID: 493020; "Cytotoxicity Screening for Potential Inhibitors of Bacterial Capsule Biogenesis" Jan. 10, 2010.
PubChem AID: 488970; "Screening for Inhibitors of Bacterial Capsule Biogenesis—Summary" Version 1.13; Feb. 12, 2013.
PubChem CID: 23602075; "SMR000563200" Dec. 12, 2007 modified Mar. 5, 2016.
PubChem AID: 488970; "Screening for Inhibitors of Bacterial Capsule Biogenesis—Summary" Version 1.12; Apr. 16, 2012.
PubChem SID: 126497311; "KSC-242-106-A1CI5" Version 1; Nov. 4, 2011.
PubChem SID: 126497311; "KSC-242-106-A1CI5" Version 2; Nov. 4, 2011.

* cited by examiner

Figure 2
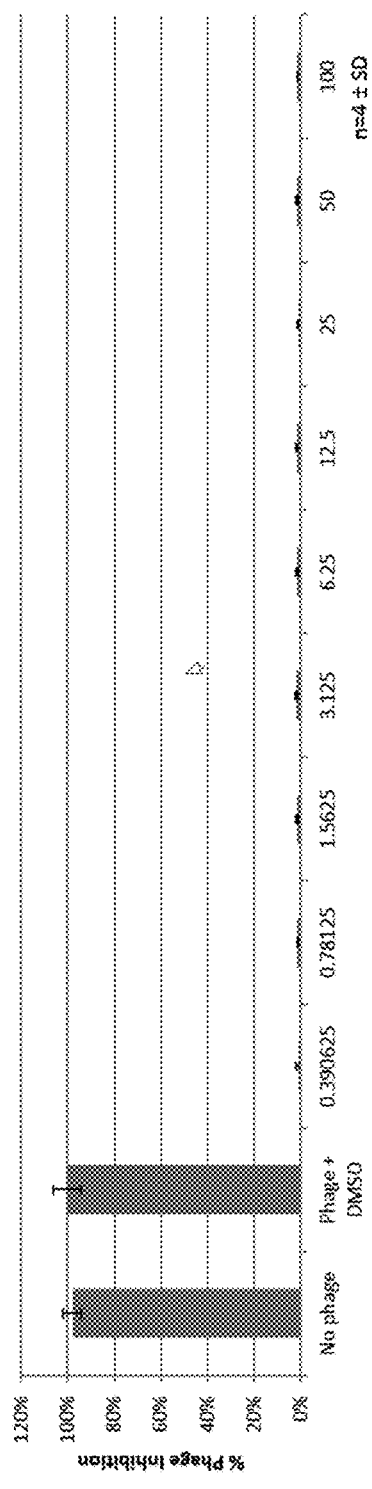
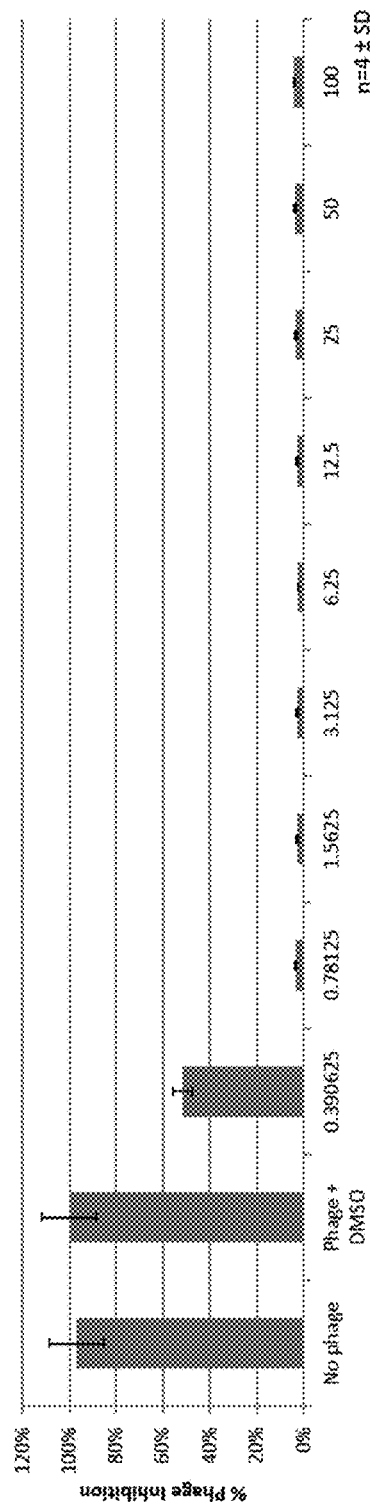

Reagents: (a) POCl$_3$, DMF, H$_2$NOH, (b) NaOMe, MeOH, t-Bu 2-mercaptoacetate, (c) 2,6-difluorobenzoyl chloride, TEA, DCM, 16 h (d) TFA/DCM (1/3) 2 h.

ETHOXYPHENYL THIENYL COMPOUNDS AND METHODS FOR THE TREATMENT OF BACTERIAL INFECTIONS

CROSS REFERENCE TO RELATED APPLICATIONS

This application claims the benefit of U.S. application Ser. No. 14/305,649 filed Jun. 16, 2014 entitled "COMPOSITIONS AND METHODS FOR THE TREATMENT OF BACTERIAL INFECTIONS" and U.S. Provisional Appn. 61/890,930, filed Oct. 15, 2013, entitled "COMPOSITIONS AND METHODS FOR THE TREATMENT OF BACTERIAL INFECTIONS" which are hereby incorporated by reference in their entireties.

STATEMENT REGARDING FEDERALLY SPONSORED RESEARCH OR DEVELOPMENT

This invention was made with government support under Grant No. MH090791 and HG005031 awarded by the National Institutes of Health. The United States Government has certain rights in the invention.

1. FIELD OF THE INVENTION

This invention relates generally to the discovery of a method of inhibiting, preventing or treating bacterial infections. The invention also relates to a method of inhibiting bacterial capsule biogenesis.

2. BACKGROUND OF THE INVENTION

2.1. Introduction

Uropathogenic *Escherichia coli* (UPEC) is the leading cause of community-acquired urinary tract infections (UTIs). Over 100 million UTIs occur annually throughout the world, including more than 7 million cases in U.S. adolescents and adults (14). UTIs in younger children are associated with greater risk of morbidity and mortality than in older children and adults. Antimicrobial resistance among UPEC is on the rise (10, 15-18), driving efforts to discover vulnerable targets in the molecular pathogenesis of infection.

During UTI, UPEC lives in intracellular and extracellular locales. UPEC adheres to the apical bladder epithelium and invades into it (19-21). Within the bladder epithelium, UPEC typically reproduces in a biofilm-like state called intracellular bacterial communities (IBC; (5)). After maturation of IBCs, UPEC disperses away from the IBC and exits the infected cells. Extracellular UPEC must then re-adhere, initiating the invasion and intracellular reproduction phases again. Past studies have revealed bacteria encased in the IBC within a complex matrix of fibrous protein assemblies and polysaccharides (5). Our prior studies have also shown that disruption of the IBC pathway aborts experimental UTI, highlighting the importance of this intracellular lifecycle (22-25). A detailed study of urine samples from women with acute UTI demonstrated IBC in shed bladder epithelial cell, showing that the pathway is conserved in humans (26).

Investigators have found that bacterial encapsulation is an important UPEC virulence factor (4-6), and experiments show that the K capsule contributes to multiple aspects of pathogenesis, including IBC formation. K capsules, also called K antigens, are enveloping structures composed of high-molecular-weight polysaccharides. Among UPEC, the K antigens K1, K2, K5, K30, and K92 are thought to be most prevalent (27). Capsules are well-established virulence factors for a variety of pathogens that are thought to protect the cell from opsonophagocytosis and complement-mediated killing (reviewed in (28, 29)). While they did not study the effects of K antigen from UPEC, Llobet et al. recently demonstrated that the highly acidic polysaccharide capsules of diverse organisms including *Klebsiella pneumoniae, Pseudomonas aeruginosa*, and *Streptococcus pneumoniae* interact strongly with APs, acting as "sponges" to sequester and neutralize the APs (30).

Of the different K types, the Group 2 and Group 3 capsules are most prevalent among UPEC isolates, with K1 and K5 being leading types. Although the capsules have different compositions, they are regulated, synthesized, assembled, and exported by functionally homologous factors, leading us to hypothesize that we can develop small molecular inhibitors of K-type encapsulation that target the most medically important K capsule types. Furthermore, the medically important infectious agents *Campylobacter jejuni, Haemophilus influenzae, Neisseria meningitides*, and *Salmonella typhimurium* among others, use homologous components in the biogenesis of their capsules. The K1 capsule type is closely associated with pathogenic isolates; not only is it the leading type in UTI, but it also accounts for much of the extra-urinary tract complications. Animals studies of *E. coli* K1 sepsis demonstrated that injection of a K1 capsule degrading enzyme abrogates infection (7). However, the enzyme treatment is immunogenic; accordingly, chemical inhibition may prove to be a superior approach.

There are currently no therapeutics that specifically inhibit the formation of any bacterial capsule, and this is a novel strategy for preventing or decreasing the prevalence of chronic or re-occurring urinary tract infections. New insights into the roles of K1 capsules in UPEC virulence during UTI make capsules an attractive target for therapeutic intervention. Antimicrobial resistance among UPEC is on the rise (11, 12, 15, 31, 32), and the discovery of novel small molecules that can act as probes or lead compounds for the investigation and treatment of UTI will add to the arsenal of compounds available for single or combination therapies.

3. SUMMARY OF THE INVENTION

The invention provides compounds having the structure below:

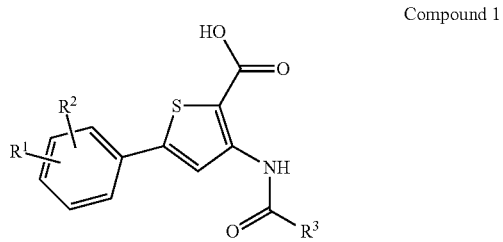

Compound 1 each $R^1$, $R^2$, and $R^3$ may independently be aryl, $C_{1-8}$ alkyl, $C_{1-8}$ alkyl(aryl), $C_{1-8}$ alkoxy, $C_{1-8}$ alkoxy aryl, $C_{1-8}$ haloalkoxy, $C_{2-8}$ alkenyl, $C_{3-8}$ alkynyl, $C_{3-8}$ cycloalkyl, —$CF_3$, —$(CH_{3-8})_xNR_4R_5$, —CN, —$CONR_4R_5$, —$COR_4$, —$CO_2(CH_2)_xNR_4R_5$, —$CO_2R_4$, haloaryl, halogen, heteroaryl, hydroxyl, —$N_3$, —$NHCOR_4$, —$NHSO_2C_{1-8}$ alkyl, —$NHCO_2C_{1-8}$ alkyl, —$NO_2$, —$NR_4R_5$, —$O(CH_2)_xNR_4R_5$, —$O(CH_2)_xCO_2R_4$, —$OCOC_{1-8}$ alkyl, —$OCO(CH_2)_x NR_4R_5$, —$SO_{(1-3)}R_4$, or —$SR_4$; each $R_4$ and $R_4$ are independently aryl, $C_{1-8}$ alkyl, $C_{1-8}$ alkyl alcohol, $C_{1-8}$ alkyl amino, $C_{1-8}$ alkyl amido, $C_{1-8}$ alkyl(aryl), $C_{1-8}$ alkyl ($C_{3-8}$ cycloalkyl), $C_{1-8}$ alkyl guanidinyl, $C_{1-8}$ alkyl heteroaryl, $C_{1-8}$ alkyl imidazolyl, $C_{1-8}$ alkyl indolyl, $C_{1-8}$ alkyl thioether, $C_{1-8}$ alkyl thiol, $C_{2-8}$ alkenyl, $C_{3-8}$ alkynyl, $C_{3-8}$ cycloalkyl, or H; or $R_4$ and $R_5$ together make a 4-8 member ring which may be substituted with one or more heteroatoms; n is 0, 1, 2, 3, 4 or 5; and each x is independently 0-8. The invention also includes salts thereof.

The invention also provides compounds and uses having the structure:

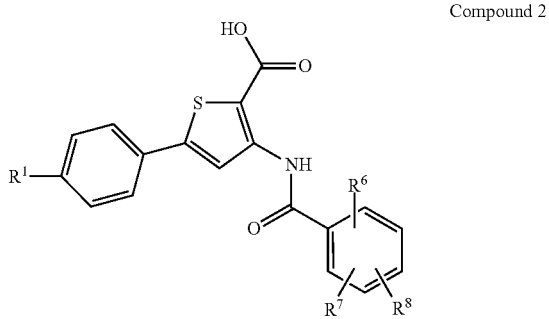

Compound 2 wherein each $R^1$, $R^6$, $R^7$ and $R^8$ may independently be $C_{1-8}$ alkyl, $C_{1-8}$ alkyl(aryl), $C_{1-8}$ alkoxy, $C_{1-8}$ haloalkoxy, $C_{1-8}$ alkoxy aryl, $C_{2-8}$ alkenyl, $C_{3-8}$ alkynyl, $C_{3-8}$ cycloalkyl, —CF$_3$, —CN, halogen, or hydrogen.

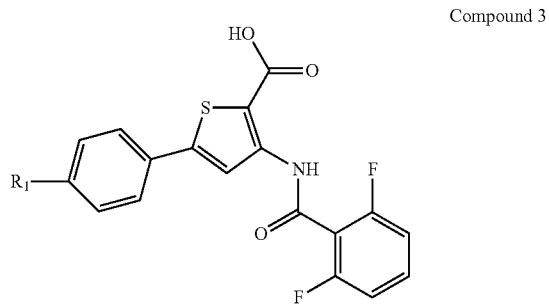

Compound 3 where $R^1$ is $C_{1-8}$ alkyl or $C_{1-8}$ haloalkoxy. Compound 3 where $R^1$ is ethoxy is also referred to as DU011 or ML317 in this disclosure. Compound 3 where $R^1$ is n-butoxy is CID 56643007 and R' is n-trifluoropropyloxy is CID 56643020.

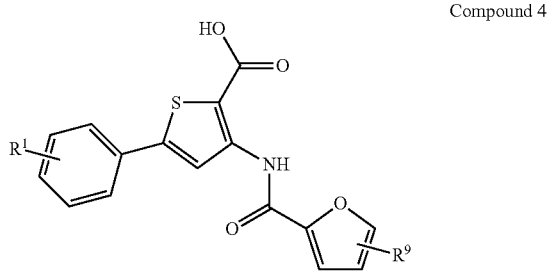

Compound 4 where each of $R^1$ and $R^9$ is $C_{1-8}$ alkyl, $C_{1-8}$ haloalkoxy or halogen. Compound 4 where $R^1$ is n-trifluoropropyloxy and $R^9$ is 5-bromo is CID 56643022. Compound 4 where $R^1$ is n-butoxy and $R^9$ is 5-bromo is CID 56643021 and n-trifluoropropyloxy is CID 56643020.

In particular non-limiting embodiments, the present invention provides a method of inhibiting capsule biogenesis in a bacterium which comprises administering to the bacterium an effective amount of a composition comprising Compound 1, 2, 3, or 4 or salt thereof.

The invention also provides a method of treating a subject suffering from a bacterial infection comprising administering a therapeutically effective amount of a composition comprising Compound 1, 2, 3, or 4 and/or salts thereof. The bacterial infection may be a urinary tract infection (UTI), a bladder infection, a kidney infection, or a disseminated *staphylococcus* infection.

The bacterium may be a gram-negative bacteria such as a *Campylobacter jejuni, Enterobacter cloacae, Haemophilus influenzae, Klebsiella pneumoniae, Legionella pneumophila*, Methicillin-resistant *Staphylococcus aureus* (MRSA), *Neisseria meningitides, Proteus mirabilis, Pseudomonas aeruginosa, Salmonella typhimurium, Serratia marcescens, Staphylococcus aureus*, or a combination thereof. In the methods above, they may further comprise administering an agent that targets a bacterial cell wall such as a penicillin or a cephalosporin.

The subject may be a mammal such as a human.

4. BRIEF DESCRIPTION OF THE FIGURES

FIG. 1. Capsule biogenesis inhibitors. Panel A: *E. coli* capsule biogenesis components and conservation between sequenced pathogenic isolates. Panel B: The bacteriophage-dependent screen for chemical inhibitors. In the first step, *E. coli* is grown in the presence of chemicals to be tested, permitting the elimination of chemicals producing simple growth defects. In the next step, the bacteriophage K1F is added to growing cultures with putative chemical inhibitors. The K1F phage requires the K1 polysaccharide capsule for binding and cellular entry, which when successful results in lysis of the target bacterium. In the presence of a chemical inhibitor of capsule biogenesis or a genetic capsule mutant, K1F fails to lyse the target cells. Thus inhibitors of capsule biogenesis produce growth of *E. coli* in the presence of the K1F phage. The chemical 3-(2,6-difluorobenzamido)-5-(4-ethoxyphenyl)thiophene-2-carboxylic acid as disclosed in this document was identified using this assay.

FIG. 2. Dose-dependent capsule inhibition by N-pyridin-4-yl-1,3-benzothiazole-6-carboxamide and 3-(2,6-difluorobenzamido)-5-(4-ethoxyphenyl)thiophene-2-carboxylic acid leading to T7 phage lysis of target bacteria. Bacteria were grown with or without T7 bacteriophage and with DMSO or chemical inhibitor at increasing micromolar concentrations. A high % phage inhibition indicates loss of polysaccharide capsule that normal precludes T7 phage attachment, entry, and lysis of target bacteria.

Figure 3:
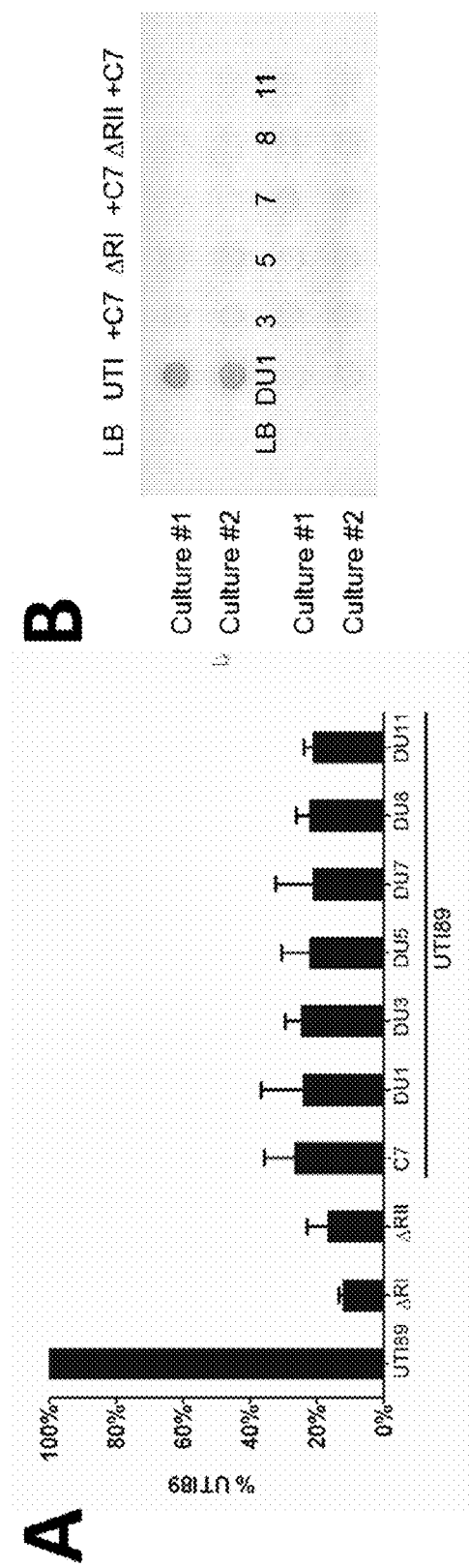

FIG. 3. The orcinol reaction and capsule antigen dot blots to demonstrate reduction in capsule after treatment with N-pyridin-4-yl-1,3-benzothiazole-6-carboxamide (DU003) and 3-(2,6-difluorobenzamido)-5-(4-ethoxyphenyl)thiophene-2-carboxylic acid (DU011). Panel A: Orcinol biochemical tests for extracted K1 capsule polysaccharide from wild type (UT189), genetic capsule mutants (UTI DRegion1 and UTI DRegion11), and chemical treatment (UTI+DU003 at 50 µM). Results are shown as a percentage of wild type. Note that orcinol reacts with other non-capsule sugars in the extract preparations providing some background reactivity even in a capsule synthesis mutant (UTI DRegion11). Panel B: Whole cell immunodot blot using anti-K1 capsule antibody. UTI indicates the wild type *E. coli* strain treated with vehicle control. ΔRI and ΔRII are genetic capsule mutants treated with vehicle control DU003 indicates cells treated with the chemical N-pyridin-4-yl-1,3-benzothiazole-6-carboxamide at 50 µM. LB indicates a negative control in which bacterial growth medium alone was applied to the membrane. Duplicate independent experiments are shown side by side.

Figure 4:
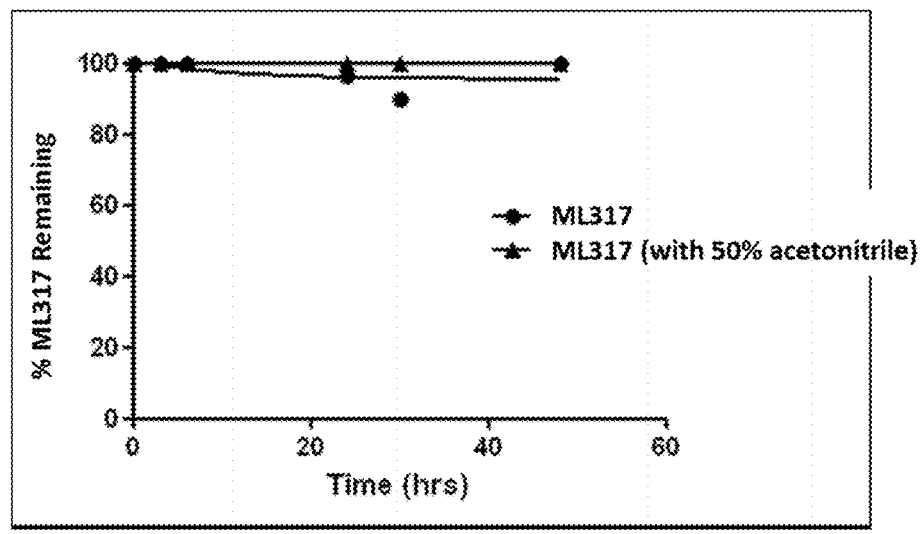

FIG. 4. Graph depicting the stability for ML317 after 48 hours in two separate solvent systems FIG. 5. Graph depicting stability of the probe to thiol.

Figure 6:
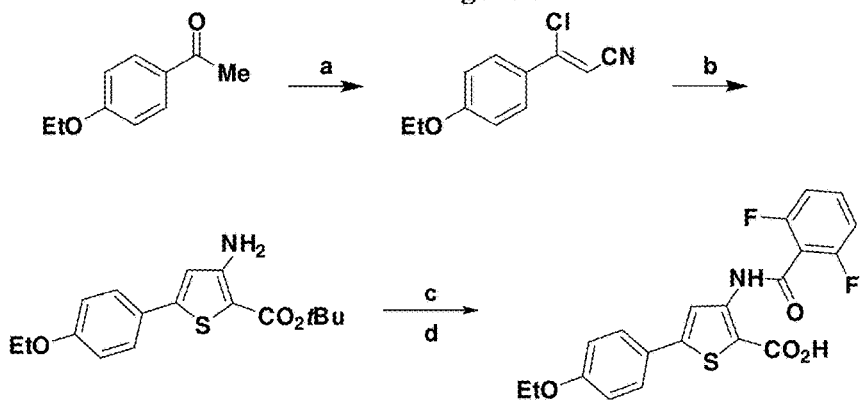

FIG. 6. Synthetic route for probe and analogue generation.

Figure 7:
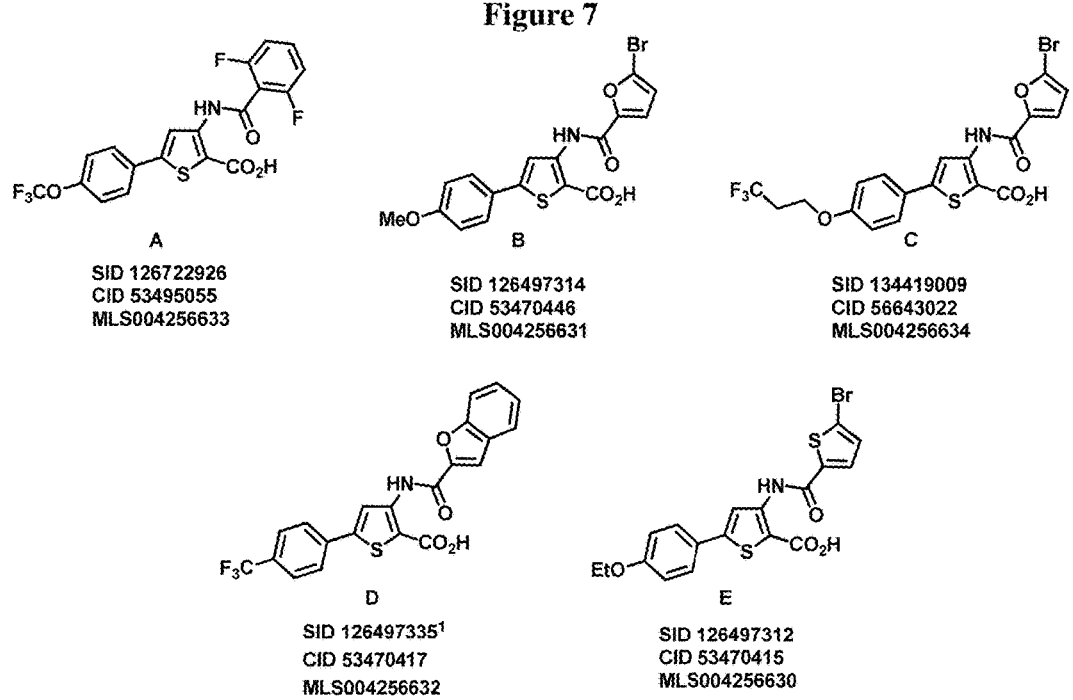

FIG. 7. Five analogues chosen to support probe ML317.

Figure 8:
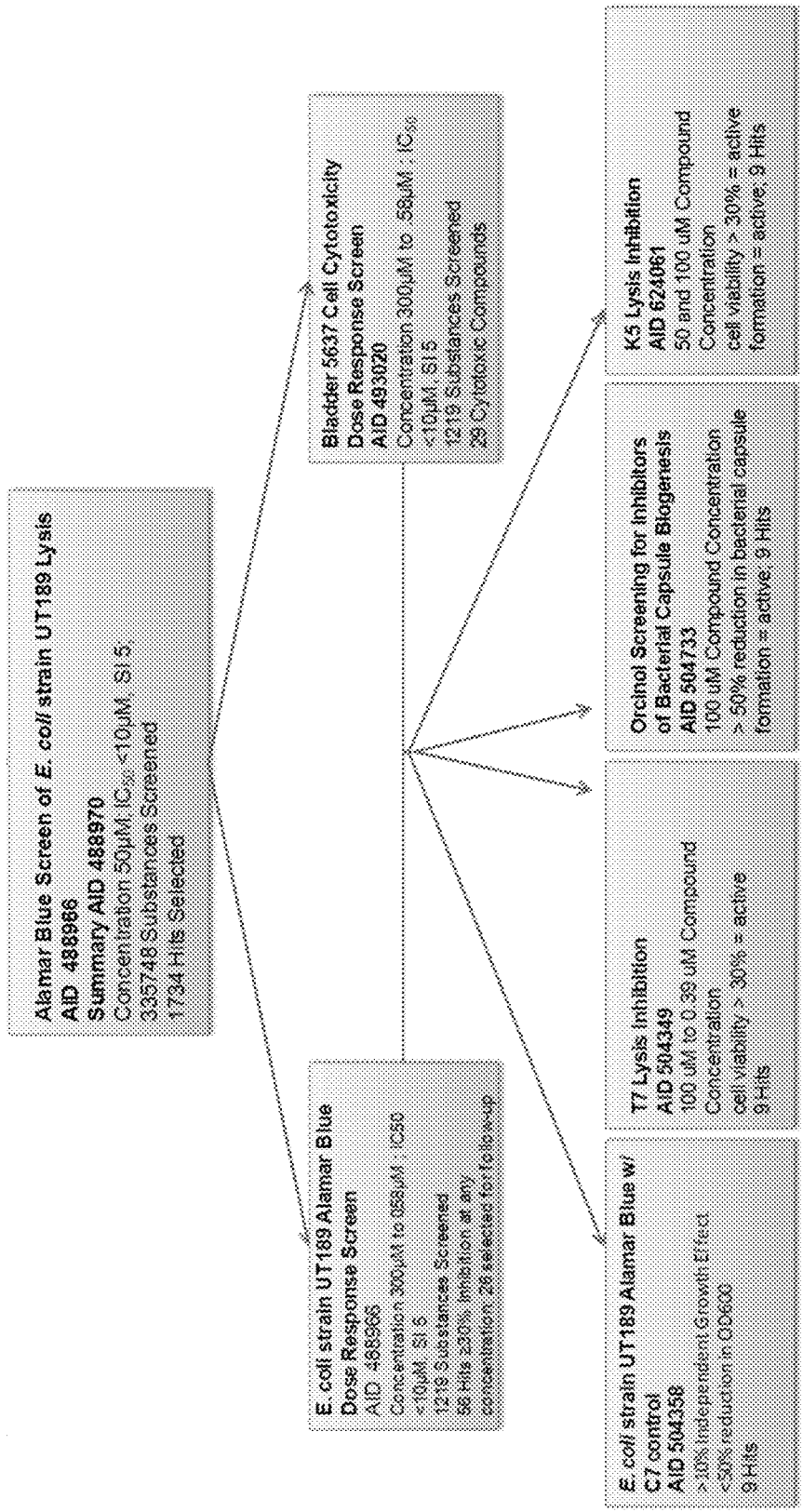

FIG. 8. HTS to compound hit flowchart.

Figure 9:
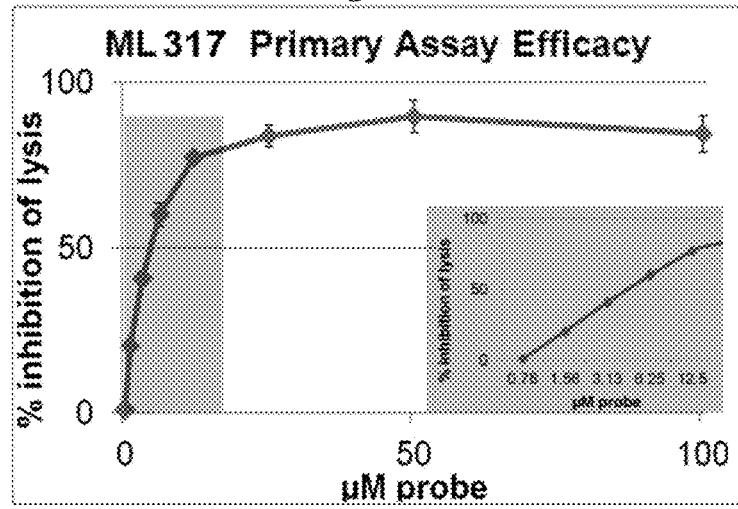
Figure 10:
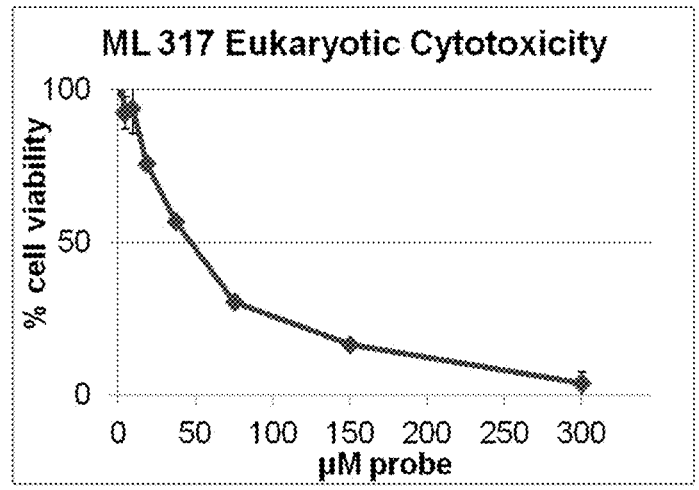

FIGS. 9 and 10. Efficacy and cytotoxicity analysis of ML317.

Figure 11:
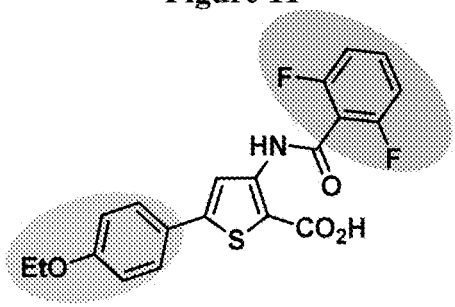

FIG. 11. Regions of the compound hit identified for initial SAR exploration.

Figure 12:
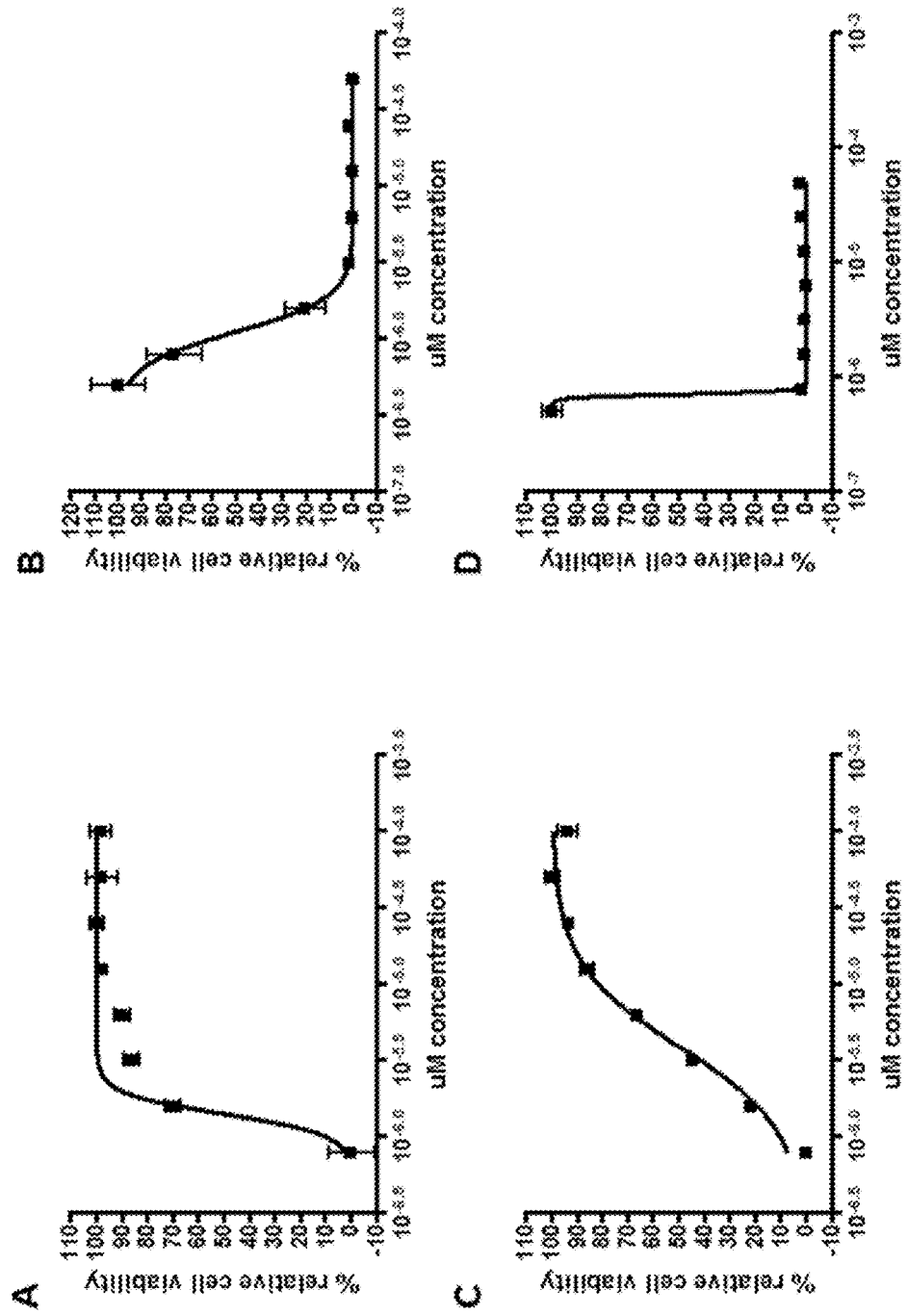

FIG. 12. Concentration-response inhibition of K1 and T7 phage-mediated cell lysis. K1 (A, C) and T7 (B, D) phage activity in *E. coli* strain UTI89 or EV36 (K1:K-12 hybrid strain), respectively, following treatment with various concentrations of DU003 (A, B) or DU011 (C, D).

Figure 13:
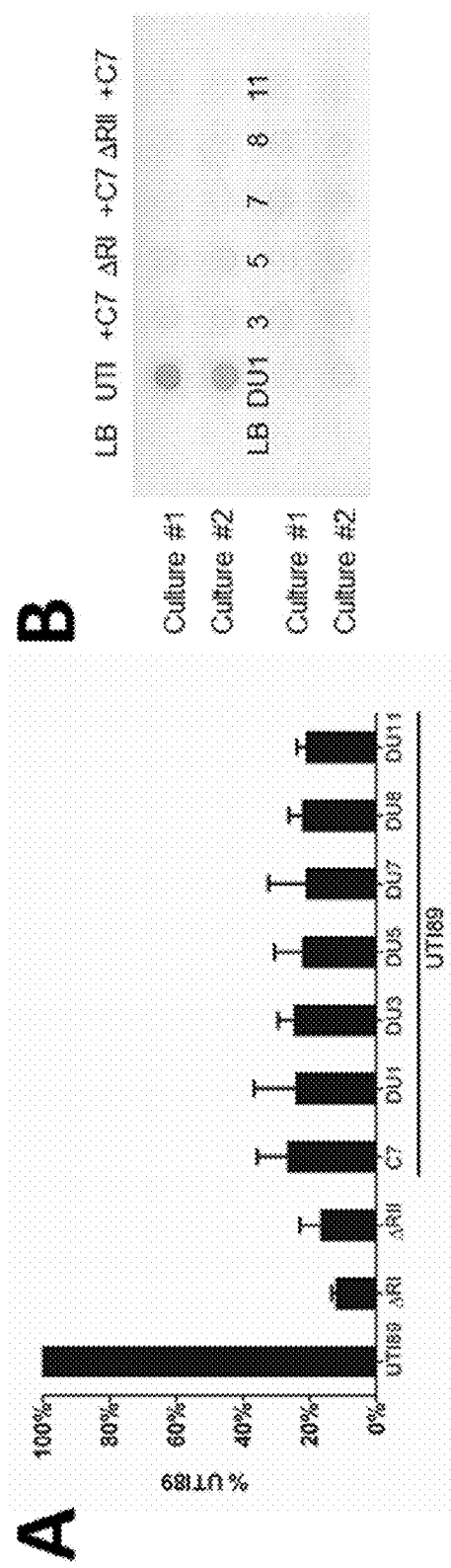

FIG. 13. Biochemical and immunologic verification of *E. coli* Group 2 capsule inhibition through small molecules. A) Orcinol reactivity of capsular material released by mild acid treatment of cultures grown with 1% DMSO vehicle (UTI89 and genetic capsule mutants) or 100 µM C7, DU001, DU003, DU005, DU007, DU008, or DU011. Data represent independent experiments performed in duplicate. Treatment of K1 strain UTI89 with compounds reduces amount of orcinol-reactive polysaccharides on surface of bacteria by ~80%. B) Whole-cell anti-K1 dot blots of cultures of UTI89 or indicated genetic capsule mutants treated with 1% DMSO or 100 µM DU001, DU003, DU005, DU007, DU008, or DU011 indicate that treatment of cultures with compounds reduces K1 reactive material to levels comparable to those of genetic capsule mutants. ΔRI and ΔRII indicate a complete deletion of Region I of the capsule kps and Region II capsule neu loci, respectively.

Figure 14:
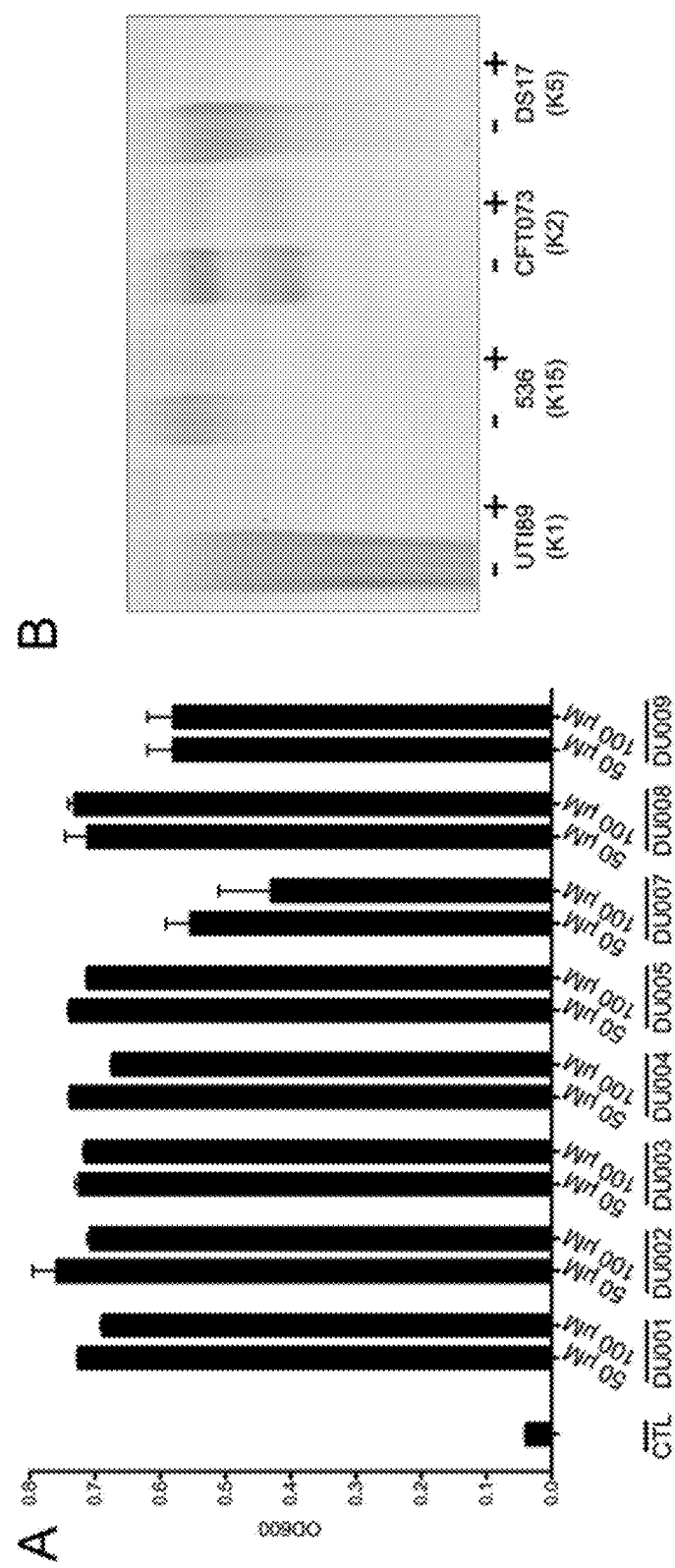

FIG. 14. Inhibitor treatment decreases capsule production in different pathogenic *E. coli* serotypes. A) K5 *E. coli* was grown in vehicle or with different inhibitors (50 and 100 µM) and then challenged with K5 lytic phage, which results in cell death in the presence of capsule. Growth was measured by absorbance at $OD_{600}$. B) Capsular material was isolated from multiple strains grown with and without inhibitor DU011 (200 µM). Capsule preparations were performed in at least 3 independent trials. A single representative image is shown.

Figure 15:
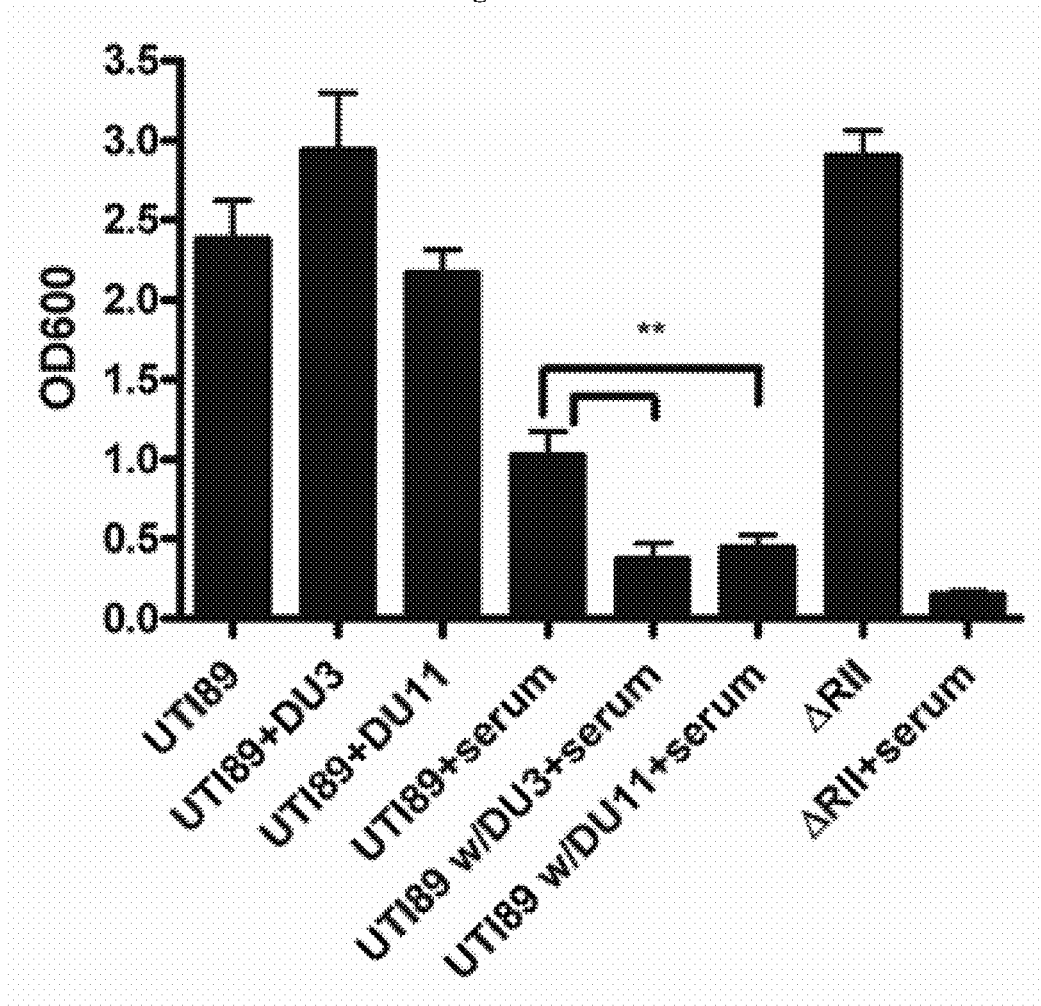

FIG. 15. Capsule inhibitors sensitize UPEC K1 strain to serum-mediated killing. *E. coli* UTI89 and genetic capsule mutants were grown in the presence and absence of DU003 or DU011 at 50 µM and exposed to human serum. Bacterial metabolism and viability was measured using MTT (3-(4,5-Dimethylthiazol-2-yl)-2,5-diphenyltetrazolium bromide). UTI89 grown in the presence of 50 µM DU003 or DU011 were significantly more sensitive to pooled human serum compared to control UTI89 (** $p=0.0067$). This was similar to the serum sensitivity of the capsule mutant UTI89 ΔRII. ΔRI and ΔRII indicate a complete deletion of Region I of the capsule kps and Region II capsule neu loci, respectively.

Figure 16:
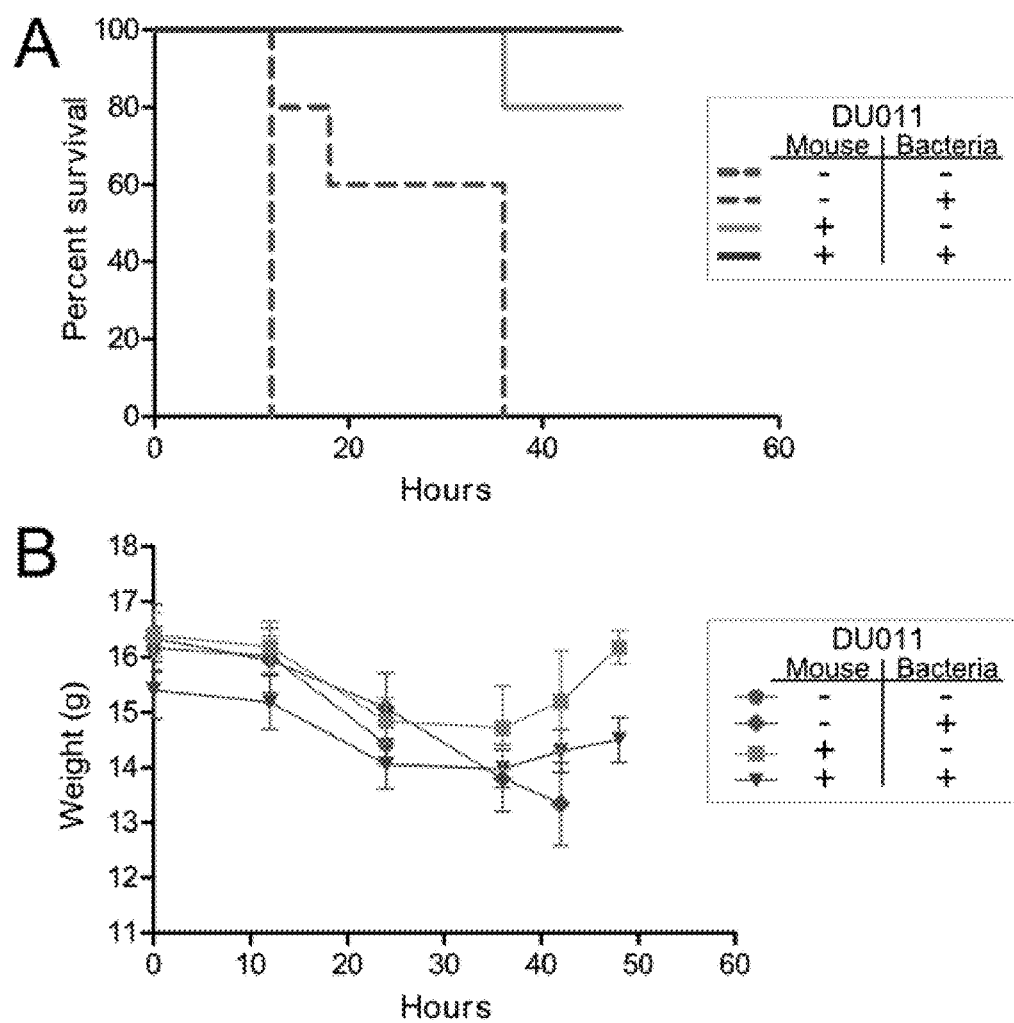

FIG. 16. ML317 (DU011) protects mice against a lethal dose of K1 *E. coli*. A) C57BL/6 mice were administered subcutaneous 1% DMSO (control) or DU011 (100 µL, of 1 mg/ml in 1% DMSO) 12 hours prior to lethal intraperitoneal injection with $10^8$ CFU of UTI89 prepared in media containing 1% DMSO or DU011 (200 µM in 1% DMSO). Surviving animals continued to receive DMSO or DU011 each 12 hours through the course of the experiment, according to their groups (B) Weight was monitored during DMSO and DU011 administration and after infection.

Figure 17:
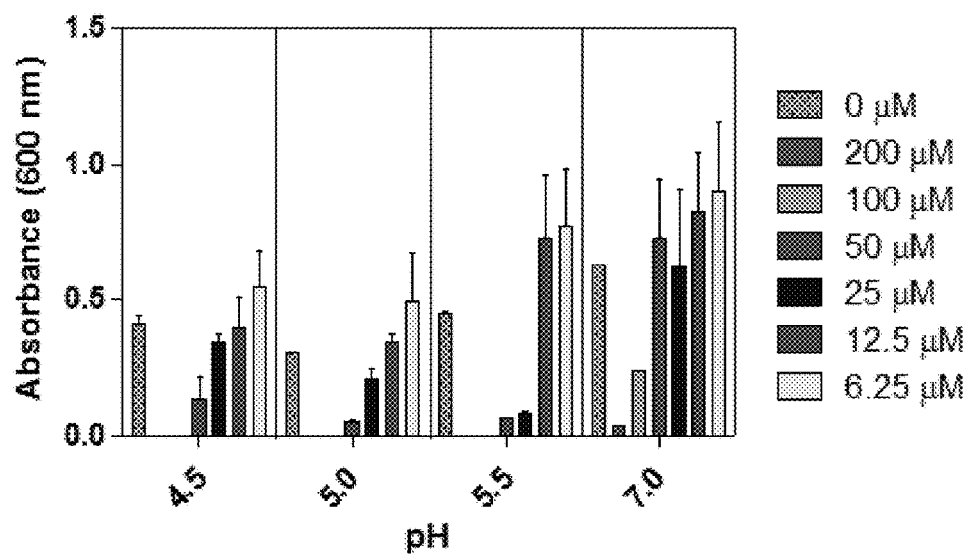

FIG. 17. Inhibition of Methicillin Resistant *Staphylococcus aureus* (MRSA) Strain USA300 by ML317 (DU011). USA300 was grown shaking in TSB medium buffered at different pH as indicated in the figure with the addition of different concentrations of the chemical probe ML317. Growth was measured by absorbance readings as indicated. Concentrations of 25 to 50 µM of ML317 were sufficient to produce inhibition of MRSA at pH 5 and 5.5. ML317 inhibited growth of MRSA at pH 7 when introduced at concentrations of 100 and 200 µM. Culture of bacteria from the experiments indicated that ML317 was bactericidal under the experimental conditions.

5. DETAILED DESCRIPTION OF THE INVENTION

Uropathogenic *Escherichia coli* (UPEC) is the leading cause of community-acquired urinary tract infections (UTIs). Over 100 million UTIs occur annually throughout the world, including more than 7 million cases in U.S. adolescents and adults. UTIs in younger children are associated with greater risk of morbidity and mortality than in older children and adults. During UTI, UPEC exists in both intracellular and extracellular spaces. Infection is initiated by adherence to the apical bladder epithelium and then invading this layer of cells. Within the bladder epithelium, UPEC typically reproduces in a biofilm-like state composed of intracellular bacterial communities (IBC). After maturation of IBCs, UPEC disperses away from the IBC and exits the infected cells. Extracellular UPEC must then re-adhere, initiating the invasion and intracellular propagation phases again. Bacterial-epithelial interactions incite a strong inflammatory response through which the UPEC must persist. One persistence factor is the K type polysaccharide capsule. Capsule protects against phagocytosis, complement action, and antimicrobial peptide killing. Recent studies have also revealed that capsule along with fibrous protein assemblies is a key part of the IBC formation. Antimicrobial resistance among UPEC is increasing, driving efforts to identify therapeutic targets in the molecular pathogenesis of infection. Capsules are an attractive target because of new insights into the roles of bacterial K capsules in UPEC virulence during UTI. Specific investigations have shown that K capsule contributes to multiple aspects of pathogenesis, including IBC formation. In this program we used a cell-based assay to screen 335,740 compounds from the MLSMR library and identified 1,767 hits that inhibited K1 bacterial capsule formation. Of those hits, 59 were confirmed as active in a dose-responsive manner, and eight compounds were shown in secondary assays to specifically inhibit capsule formation. Of those eight compounds, three of those were further characterized for structure-activity relationships, mechanism of action, and therapeutic index. The probe compound, 3-[(2,6-difluorobenzoyl)amino]-5-(4-ethoxyphenyl)thiophene-2-carboxylic acid, was identified as a small molecule inhibitor of K1 capsule formation with an $IC_{50}$ value of 4.5±2.4 µM and a >10-fold selectivity index (SI) in BC5637 bladder cells. The probe has been broadly profiled for off-target liabilities and assessed for aqueous solubility, parallel artificial membrane permeability, and hepatocyte microsome and plasma stability. It is suitable for use as a lead compound for inhibition of K1 capsule formation.

Probe Structure & Characteristics:

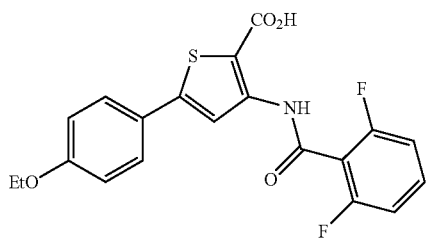 [SMILES: CCOc1ccc(-c2cc(NC(=O)c3c(F)cccc3F)c(C(=O)O)s2)cc1]

ML317

| SID/CID/ML# | Target Name | $IC_{50}$ (μM) [AID] | Anti-target Name(s) | $CC_{50}$ (μM) [SID, AID] | Fold Selective[a] | Secondary Assay(s) Name: $IC_{50}$ (μM) [AID] |
|---|---|---|---|---|---|---|
| 103147605/ 23602075/ ML317 (commercial sample) | K1 Capsule | 4.5 ± 2.4; [488970] | Mammalian cell toxicity | $CC_{50}$ = 47.2 ± 7.2; [10314760], AIDs 488970, 493020, 504769, 504831, 588399 | 10.5 | T7 phage assay <0.39 μM; AID 488970 Orcinol assay 24% of control value; AID 488970, 624060 |
| 126497311/ 23602075/ ML317 (synthesized sample) | K1 Capsule | 1.89 ± 1.56; [488970] | Mammalian cell toxicity | $CC_{50}$ = 51.6 ± 13.69; [126497311, AIDs 488970, 493020, 504769, 504831, 588399 | 27.3 | T7 phage assay <0.625 μM; AID 488970 Orcinol assay 21% of control value; AID 488970, 624060 |

[a]Calculated as $CC_{50}/IC_{50}$

This team previously reported a probe ML317. In short, the probe ML317 was found to have an $IC_{50}$ of 1.89 μM in a bacterial viability assay in the presence of K1 phage, a $TC_{50}$ (toxicity) of 51.6 μM, a selectivity of 27, a T7 phage bacterial viability assay $IC_{50}$ of <0.39 μM, and to reduce the bacterial capsule-dependent orcinol stain to 21% of the control sample. Additional biological characterization for probe ML317 is provided in Section 4.1 of this report.

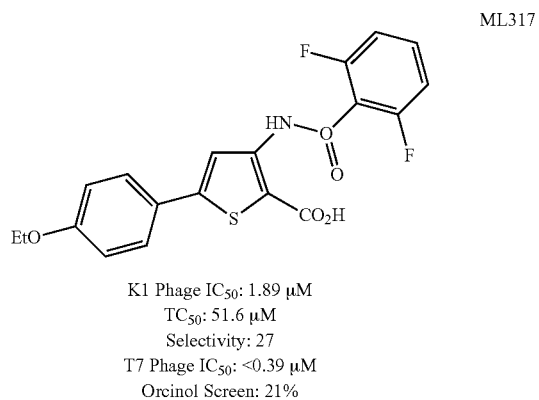

ML317

K1 Phage $IC_{50}$: 1.89 μM
$TC_{50}$: 51.6 μM
Selectivity: 27
T7 Phage $IC_{50}$: <0.39 μM
Orcinol Screen: 21%

Through the efforts of the Seed lab toward developing assay and screening techniques for inhibitors of bacterial capsule biogenesis, a sample of 2,195 compounds obtained from the Developmental Therapeutics Program at the National Cancer Institute were tested. In the K1F phage lysis 96-well plate format assay, 35 (1.59%) of the compounds were found to have inhibitory activity, of which only nine compounds gave reproducible phage lysis inhibition activity in shaken tube format. These nine compounds were taken onto a secondary screening process from which two capsule biogenesis inhibitors emerged. Malachite green oxalate (NCS5550), a compound not known to inhibit capsule biogenesis, was found to produce metabolites with previously reported toxicities to mammalian systems and was thus discarded. The second inhibitor, 2-(4-phenylphenyl)-benzo[g]quinoline-4-carboxylic acid (NSC136469), or C7, was employed as a prototype small molecule inhibitor of capsule biogenesis since it inhibited K1F phage lysis of UPEC K1 strain UTI80 reproducibly in the tests following HTS. Furthermore, this inhibition was found to behave in a dose-dependent manner with the inhibitory effect reaching saturation at approximately 25 μM C7, producing approximately 50% inhibition of K1F phage lysis of UPEC at 12.5-25 μM (33).

The present disclosure provides compositions and methods for the treatment of bacterial infections.

5.1. Definitions

The term "administration" or "administering," as used herein, refers to providing, contacting, and/or delivery of a composition by any appropriate route to achieve the desired effect. These composition may be administered to a subject in numerous ways including, but not limited to, orally, ocularly, nasally, intravenously, topically, as aerosols, suppository, etc. and may be used in combination.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms.

"Alkoxy" refers to a radical —OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted.

As used herein, the term "bacteria" and "bacterium" are used interchangeable any to any bacteria that has a polysaccharide capsule. IN some embodiments, the bacteria comprises a gram-negative bacteria. In certain embodiments, the bacteria is selected from the group consisting of *E. coli, C. jejuni, N. meningitides, K. kingea, Proteus mirabilis, Enterobacter cloacae, Serratia marcescens, Klebsiella pneumoniae, Legionella pneumophila, Pseudomonas aeruginosa* and/or combinations thereof.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted. The substituted heteroaryl group may be a halo substituted thiophene, e.g., bromo thiophene.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, halogen, hydroxyl, $-N_3$, $-NH_2$, $-SO_{(1-3)}H$, or $-SH$.

As used herein, the term "subject" is intended to include human and non-human animals. Exemplary human subjects include a human patient having a bacterial infection. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "therapeutically effective" refers to a dosage of a composition (e.g., N-pyridin-4-yl-1,3-benzothiazole-6-carboxamide, analogues thereof, derivatives thereof, and/or salts thereof) that is effective for eliciting a desired effect. This term as used herein may also refer to an amount effective at bringing about a desired in vivo effect in an animal, mammal, or human, such as reducing inflammation, fever and the like that is commonly associated with a bacterial infection. A therapeutically effective amount may be administered in one or more administrations (e.g., the composition may be given as a preventative treatment or therapeutically at any stage of disease progression, before or after infection, before or after the onset of symptoms, and the like), applications or dosages and is not intended to be limited to a particular formulation, combination or administration route. It is within the scope of the present disclosure that the composition may be administered at various times during the course of infection of the subject. The times of administration and dosages used will depend on several factors, such as the goal of treatment (e.g., treating v. preventing), condition of the subject, etc. and can be readily determined by one skilled in the art. For example, in one embodiment the composition is administered at the onset of infection. In other embodiments, the composition is administered after infection, but prior to symptoms. In yet other embodiments, the composition is administered after symptoms have manifested. In yet other embodiments, the composition is administered prior to the onset of infection.

In certain embodiments, the composition may be in the form of a pharmaceutical compositions. As used herein, the term "pharmaceutical composition" refers to the combination of compound (i.e., N-pyridin-4-yl-1,3-benzothiazole-6-carboxamide, analogues thereof, derivatives thereof, and/or salts thereof) with a pharmaceutically acceptable carrier, inert or active, making the composition especially suitable for diagnostic or therapeutic use in vivo, in vivo or ex vivo. A "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. (1975)).

As used herein, the term "pharmaceutically acceptable salt" refers to any pharmaceutically acceptable salt (e.g., acid or base) of a composition of the present invention which, upon administration to a subject, is capable of providing a composition of this invention or an active metabolite or residue thereof. "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Unless defined otherwise, all technical and scientific terms used herein have the same meaning as commonly understood by one of ordinary skill in the art to which this invention belongs. The article "a" and "an" are used herein to refer to one or more than one (i.e., to at least one) of the grammatical object(s) of the article. By way of example, "an element" means one or more elements.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The following Examples further illustrate the invention and are not intended to limit the scope of the invention. In particular, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

6. EXAMPLES

Examples Section 1

Introduction: Urinary tract infections are the second most common infection in humans, and the bacterium *Escherichia coli* accounts for >80% of the infections in the community and >50% of the nosocomial infections. Polysaccharide capsules are ubiquitous among these pathogenic strains and the mechanism of capsule biogenesis is different than that for the related commensal strains. Pathogenic *E. coli* causing urinary tract infections have surged in antibiotic resistance in the past decade, particularly for the most commonly used oral agents, thus necessitating the development of new targets and chemical probes against these targets to disable the organism during infection. This disclosure describes our novel development of a screening process to identify inhibitors of *E. coli* capsule biogenesis.

Materials and Methods

Overall Assay Strategy:

The ability of the T1 bacteriophage to bind to bacterial capsule, infect, and lyse *E. coli* UT189 was used as the primary assay to identify the effects of screened compounds on bacterial capsule formation. The phenotypic end-point assay measured the fluorescence generated by cellular processing of Alamar Blue as a direct indicator of cell viability. A total of 335,740 compounds were screened using the primary assay. Following this, a concentration-dependent confirmatory assay (in a compound concentration range of 50-0.19 µM) was used in parallel with a eukaryotic cytotoxicity counterscreen (same concentration range) to determine hit $IC_{50}$s and $CC_{50}$s (and selective indices). Hits were further evaluated using three secondary assays for alternative measurement of compound-induced reduction in bacterial capsule formation (secondary assays 1 and 2) and specificity (secondary assays 3 and 4). Confirmed actives with an SI>5 were further investigated and subjected to chemical optimization, followed by secondary assay evaluation. Secondary assays more closely characterized the ability of the compounds to reduce bacterial capsule formation and can be used to examine the mechanism of action of the compounds. The combination of primary assay (to measure capsule reduction), counter assay (for general eukaryotic cell toxicity) and secondary assay (to measure reduction in capsule formation and specificity) were combined to allow a determination of probe efficacy, selectivity, and specificity.

A chemical probe for this project was defined as a small molecule that:

Has an $IC_{50}$ of <10 µM in the primary and confirmatory Alamar Blue Screen of *E. coli* strain UT189 lysis (primary assay)

Has a therapeutic index of >5 relative to the cytotoxicity in the bladder cell line Hu5637 (counterscreen)

Has an $IC_{50}$ of <10 µM in the confirmatory Bacterial Growth Screen of *E. coli* strain UT189 lysis (secondary assay 1)

Has an $IC_{50}$ of <10 µM in the T7 lysis inhibition assay, indicating the desired target specificity (secondary assay 2)

Will yield low orcinol levels that are 50% of the levels for capsule export control strain (secondary assay 3)

Will yield K5 phage sensitivity in *E. coli* strain DS17 (secondary assay 4).

2.1 Assays

A. Primary Assay: Screening for Inhibitors of Bacterial Capsule Biogenesis.

Purpose: The primary inhibition assay using *E. coli* UT189 and bacteriophage K1F was conducted to screen the MLSMR 300K compound library, to confirm 1,767 hits from the primary screen, and to verify the activity for purchased/synthesized compounds.

Summary AID: 488970

Assigned AID: 488966

B. Counterscreen: Cytotoxicity Screening for Potential Inhibitors of Bacterial Capsule Biogenesis.

Purpose: This cell-based assay measures the cytotoxicity of compounds in bladder carcinoma 5637 cells using luminescent cell viability assay readout.

Summary AID: 488970

Assigned AID: 493020, 504769, 504831, 588399

C. Secondary Assay 1: Screening for Inhibitors of Bacterial Capsule Biogenesis—*E. coli* Strain UT189 with C7 Control Purpose: This confirmatory cell-based assay provides an alternative measurement of inhibitory activity on phage-induced lysis. It measures reduction in bacterial capsule formation using an absorbance readout at $A_{600}$ instead of the alamar blue reagent.

Summary AID: 488970

Assigned AID: 504358, 504543, 504675, 504768, 588321, 588386, 588395

D. Secondary Assay 2: Screening for Inhibitors of Bacterial Capsule Biogenesis—T7 Lysis Inhibition Purpose: This secondary assay measures the compound mechanistic specificity for inhibition of bacterial capsule formation and excludes inhibitors of phage replication using a different bacteriophage (T7). In this assay, an increase in phage-induced lysis correlates to a decrease in capsule formation.

Summary AID: 488970

Assigned AID: 504349, 504538, 504676, 504767, 588322

E. Secondary Assay 3: Orcinol Secondary Screening for Inhibitors of Bacterial Capsule Biogenesis.

Purpose: This assay was performed only on the probe candidate. This is an end-point assay to measure the amount of K1 bacterial cell capsule formation in the presence of a test compound. The ability of the test compounds to inhibit the K1 capsule formation was measured by a reduction in absorbance due to the complex formed by orcinol and the capsule polysaccharide. The biochemical determination of cell-surface associated capsule was performed using UTI89 or the Delta Region I and Delta Region II capsule mutant bacterial strains.

Summary AID: 488970

Assigned AID: 504733, 624060

F. Secondary Assay 4: K5 Secondary Screening for Inhibitors of Bacterial Capsule Biogenesis.

Purpose: This assay was performed only on the probe candidate, and determined if compounds considered active in the T7 and orcinol secondary assays were able to also inhibit K5 capsule biogenesis. This assay was performed using a method identical to the T7 assay test with modification of only the test strain and bacteriophage used. In this validation test, we used *E. coli* strain DS17, a pyelonephritis clinical isolate expressing a K5 capsule. DS17 is highly susceptible to K5 phage mediated lysis. Thus, compounds that were active in the K1F phage assay and promoted lysis in the T7 phage assay were analyzed using this assay. The positive control drug C7 was used in this assay.

Summary AID: 488970
Assigned AID: 624061
2.2 Probe Chemical Characterization
2.2.1. Probe Chemical Structure and Properties

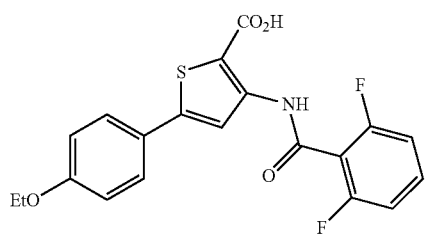

ML317

Molecular Formula: $C_{20}H_{15}F_2NO_4S$
Molecular Weight: 403.39
Exact Mass: 403.0690
CLogP: 5.1747
Topological Polar Surface Area: 75.63
Purity (RP HPLC/UV 214 nM): 97.6%
Physical State: colorless solid 2.2.2. Structure Verification and Purity: 1H NMR, 13C NMR, RP HPLC/UV/HRMS Data Proton and carbon NMR data for ML317/ MLS004256629/SID 126497311/CID 23602075: Detailed analytical methods and associated instrumentation are described in section 2.3, entitled "Probe Preparation", under general experimental and analytical details. The numerical experimental proton and carbon NMR data are presented below.

Proton NMR Data for ML317/SID 126497311/CID 23602075: $^1$H NMR (400 MHz, DMSO) δ 13.62 (s, 1H), 8.24 (s, 1H), 7.68 (d, J=6.8 Hz, 2H), 7.64 (m, 1H), 7.31 (t, J=6.8 Hz, 2H), 7.03 (d, J=7.2 Hz, 2H), 4.09 (q, J=5.6 Hz, 2H), 1.36 (t, J=5.6 Hz, 3H) ppm.

Carbon NMR Data for ML317/SID 126497311/CID 23602075: $^{13}$C NMR (100 MHz, DMSO) δ 164.6, 160.2, 159.6, 158.2, 158.1, 157.0, 148.4, 142.6, 133.5, 133.3, 127.4, 124.7, 116.7, 115.2, 113.5, 112.7, 112.5, 111.1, 63.3, 14.5 ppm.

RP HPLC/UV/HRMS Data for ML317/SID 126497311/ CID 23602075: Detailed analytical methods and associated instrumentation are described in section 2.3, entitled "Probe Preparation", under general experimental and analytical details. Purity assessment by RP HPLC/UV/HRMS at 214 nm for SID 126497311 (CID 23602075) revealed purity of 97.6% (retention time=2.423 minutes). The experimental RP HPLC/UV/HRMS spectra were measured (data not shown). HRMS (m/z) calcd for $C_{20}H_{15}F_2NO_4S$ [M+H$^+$] 404.0763. found 404.0770.

2.2.3. Aqueous Solubility:

Solubility was measured in phosphate buffered saline (PBS) at room temperature (23° C.). PBS by definition is 137 mM NaCl, 2.7 mM KCl, 10 mM sodium phosphate dibasic, 2 mM potassium phosphate monobasic and a pH of 7.4 (34). Probe ML317 (SID 103147597/CID18109210) was found to have a solubility measurement of 92.6 μg/mL, or 230 μM, under these conditions. Solubility was also assessed in primary assay media (Luria-Bertani Broth). Probe ML317 was determined to have an assay media solubility of 68 μg/mL or 169 μM. The solubility in PBS buffer is good, and only slightly less than in assay media, and, in any case, the solubility for the probe is well above its activity in the K1 and T7 assays.

2.2.4. Aqueous Stability:

Aqueous stability for the probe was assessed using two solvent systems (100% aqueous PBS, and 50:50 aqueous PBS: acetonitrile). The probe stability was measured in aqueous PBS (no antioxidants or other protectants, DMSO concentration below 0.1%, room temperature) and the results are reported as circles in the graph in FIG. 4. The probe stability was also measured in 50:50 aqueous PBS and acetonitrile and the results are reported as squares in the graph in FIG. 4. Stability data in each case is depicted as the loss of compound with time over 48 hours with a minimum of six time points and providing the percent compound remaining after 48 hours. ML317 was found to be stable in both solvent systems under these experimental conditions over the entire 48 hour study (FIG. 4).

Figure 5:
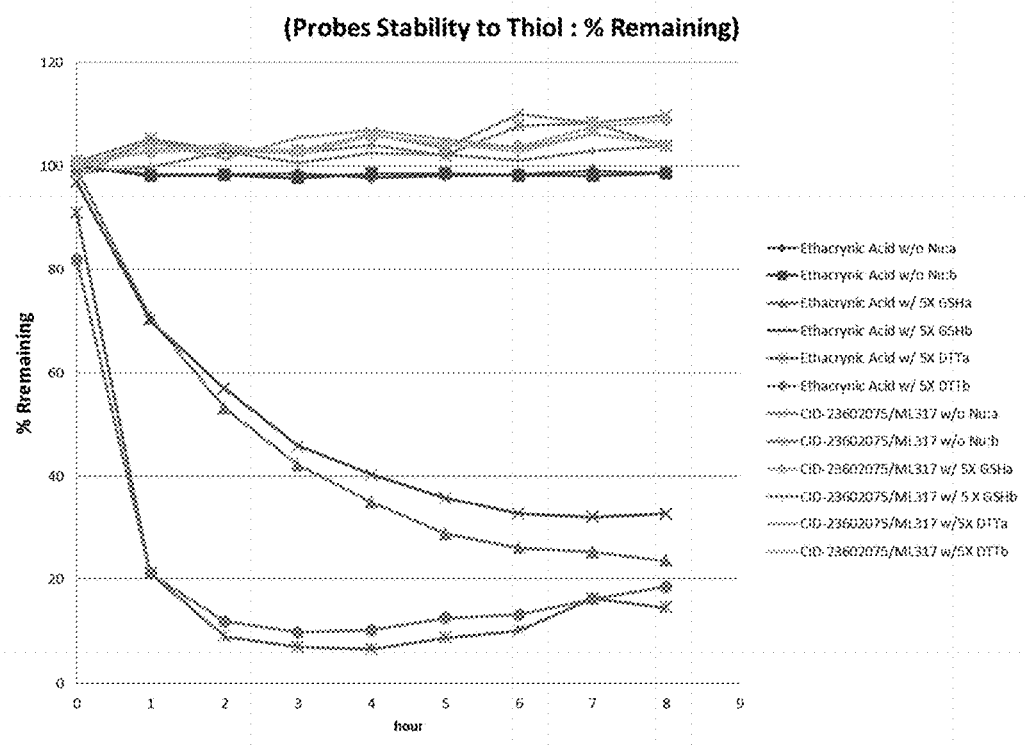

Thiol Stability:

Compounds were dissolved at 10 μM in PBS at pH 7.4 (1% DMSO) and incubated at room temperature with either no thiol source as a negative control, 50 μM glutathione (GSH), or 50 μM dithiothreitol (DTT). The mixtures were sampled every hour for eight hours and analyzed by RP HPLC/UV/HRMS. The analytical RP HPLCUV/HRMS system utilized for the analysis was a Waters Acquity system with UV-detection and mass-detection (Waters LCT Premier). The analytical method conditions included a Waters Acquity HSS T3 C18 column (2.1×50 mm, 1.8 um) and elution with a linear gradient of 1% water to 100% CH$_3$CN at 0.6 mL/min flow rate. Peaks on the 214 nm chromatographs were integrated using the Waters OpenLynx software. Absolute areas under the curve were compared at each time point to determine relative percent compound remaining. The masses of potential adducts were searched for in the final samples to determine if any detectable adduct formed. All samples were prepared in duplicate (FIG. 5). Ethacrynic acid, a known Michael acceptor, was used as a positive control. If solubility of the compound was an issue at 10 μM, PBS was substituted with PBS with 50% acetonitrile (35).

ML317 was found to be completely stable to the presence of five times its concentration of both glutathione and DTT thiol sources across all time points in our analysis (FIG. 5). Statistically, there is no drop in the % remaining concentration of ML317 in the course of these experiments. This data is easily contrasted to the data for the ethacrynic acid control compound, which is shown to react rapidly with five times its concentration of glutathione and even more rapidly with DTT.

2.2.6. Synthesis Route:

The probe compound ML317 and numerous analogues were synthesized using the reaction sequence shown in FIG. 6. Briefly, a series of aryl ketones was converted to (Z)-3-chloro-3-arylacrylonitriles through treatment with POCl$_3$, DMF and hydroxylamine. These nitriles were then converted via Fisselman reaction to tert-butyl 3-amino-5-(aryl) thiophene-2-carboxylates through a reaction with sodium methoxide and tert-butyl 2-mercaptoacetate. Lastly, these amines were coupled with various acid chlorides in the presence of triethylamine in dichloromethane followed by a removal of the tert-butyl group with trifluoroacetic acid in dichloromethane.

2.2.7. Submission of Probe and Five Analogues to the MLSMR

Samples of the probe and five analogues were prepared, analytically characterized, and shipped to the MLSMR. The structures for the five supporting analogues are shown in FIG. 7.

TABLE. 2.2.7.1

Five probe analogues with screening data

| Entry | PubChemID | K1 phage IC$_{50}$ (μM) | Cytotoxicity IC$_{50}$ (μM) | Selectivity | T7 phage IC$_{50}$ (μM) |
|---|---|---|---|---|---|
| A | SID 126722926 CID 53495055 MLS004256633 | 13.02 ± 4.6 | 51.01 ± 2.62 | 3.91 | 1.355 |
| B | SID 126497314 CID 53470446 MLS004256631 | 11.11 ± 3.33 | 50.48 ± 0.52 | 4.55 | 1.235 |
| C | SID 134419009 CID 56643022 MLS004256634 | 0.84 | 41.67 | 49.61 | <0.625 |
| D[1] | SID 126497335 CID 53470417 MLS004256632 | >100 | 72.06 | ND | 14.12 |
| E | SID 126497312 CID53470415 MLS004256630 | 17.03 ± 4.49 | 49.72 ± 6.49 | 2.92 | 3.335 |

[1]Compound selected as negative control 2.3 Probe Preparation

General Experimental and Analytical Details:

All reagents were used as received from commercial suppliers. The $^1$H and $^{13}$C spectra were recorded on a Bruker Avance 400 MHz or 500 MHz spectrometer. Chemical shifts are reported in parts per million and were referenced to residual proton solvent signals. Flash column chromatography separations were performed using the Teledyne Isco CombiFlash R$_F$ using RediSep R$_F$ silica gel columns TLC was performed on Analtech UNIPLATE silica gel GHLF plates (gypsum inorganic hard layer with fluorescence). TLC plates were developed using iodine vapor. RP HPLC/UV/HRMS analysis was carried out with gradient elution (5% CH$_3$CN to 100% CH$_3$CN) on an Agilent 1200 RRLC with a photodiode array UV detector and an Agilent 6224 TOF mass spectrometer (also used to produce high resolution mass spectra). Purification was carried out by mass directed fractionation with gradient elution (a narrow CH$_3$CN gradient was chosen based on the retention time of the target from LCMS analysis of the crude sample) on an Agilent 1200 instrument with photodiode array detector, an Agilent 6120 quadrupole mass spectrometer, and a HTPAL LEAP autosampler. Fractions were triggered using a MS and UV threshold determined by RP HPLC/UVHRMS analysis of the crude sample. The conditions for RP HPLC analysis included the following: Waters BEH C-18, 1.7 μm, 2.1×50 mm column; 0.6 ml/min flow rate; and pH 9.8 NH$_4$OH aqueous mobile phase. The conditions for purification included: Waters XBridge C18 5 μm, 19×150 mm column; 20 ml/min flowrate pH 9.8 NH$_4$OH aqueous mobile phase.

The probe was prepared using the following protocols:

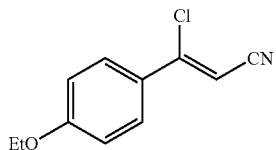 [SMILES: CCOc1ccc(/C(Cl)=C/C#N)cc1]

(Z)-3-Chloro-3-(4-ethoxyphenyl)acrylonitrile: Prepared according to an experimental outlined by Romagnoli et al. (36). To an ice cold solution of dry dimethyl formamide (8.90 g, 122 mmol) was added phosphorus oxychloride (5.57 ml, 60.9 mmol) dropwise while stirring for 15 minutes. To this cold mixture, 1-(4-ethoxyphenyl)ethanone (5.00 g, 30.5 mmol) was added dropwise while maintaining the temperature between 45-55° C. via external heat source for ten minutes. The reaction mixture was then cooled to room temperature and allowed to stir for 30 minutes. Then, a solution of hydroxylamine hydrochloride (8.46 g, 122 mmol) in dry DMF was added slowly (7 mL of 33 mL for 10 g reaction). This mixture was allowed to stir at 80° C. (an ice bath was briefly employed to control a rapid exotherm) for five minutes. Then, the remaining hydroxylamine solution was added so that the reaction mixture heated exothermically to no greater than 150° C. After the completion of addition, the reaction mixture was allowed to cool to RT and stir for an additional 30 minutes. The reaction mixture was cooled to 0° C. Cold water was then added and the reaction mixture was extracted with chloroform. The crude product was purified via normal phase, silica gel chromatography (98:2 ethylacetate/hexane) (59.1%, 6.32 g). $^1$H NMR (400 MHz, DMSO) δ 7.62 (d, J=9.2, 2H), 6.93 (d, J=9.2 Hz, 2H), 5.89 (s, 1H), 4.09 (q, J=7.2 Hz, 2H), 1.46 (t, J=6.8 Hz, 3H); ppm; $^{13}$C NMR (100 MHz, DMSO) δ 162.1, 152.9, 128.7, 126.3, 115.9, 114.7, 93.4, 63.9, 14.7 ppm; IR (ATR) 2983, 2217, 1593, 1506, 1238, 1039 cm$^{-1}$.

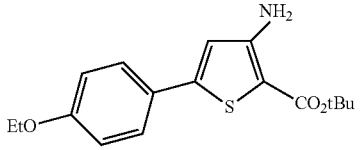 [SMILES: CCOc1ccc(-c2cc(N)c(C(=O)OC(C)(C)C)s2)cc1]

tert-Butyl 3-amino-5-(4-ethoxyphenyl)thiophene-2-carboxylate: Following the protocol outlined by Gokaraju et al. (37), to a solution of tert-butyl 2-mercaptoacetate (1.1 g, 7.42 mmol) in methanol (5 mL) was added a solution of sodium methoxide (0.401 g, 7.42 mmol) in methanol (5 mL). The reaction mixture was then stirred for 30 minutes. A solution of (Z)-3-chloro-3-(4-ethoxyphenyl)acrylonitrile (1.23 g, 5.94 mmol) in DMF was added dropwise for 10 minutes to the reaction mixture and then stirred at 60° C. for an additional two hours. Then, a solution of sodium methoxide (0.802 g, 14.84 mmol) in methanol (10 mL) was added dropwise to the reaction mixture which was then stirred for another two hours at 60° C. Cold water was added to the reaction mixture and the mixture was allowed to stir for 15 minutes. The aqueous solution was extracted three times with chloroform. The combined organic phases were washed with water, brine, dried over sodium sulfate and then concentrated in vacuo. The crude residue was purified with a DCM/MeOH eluent on a normal phase, silica gel column, giving the product (60.5%, 1.67 g). $^1$H NMR (400 MHz, DMSO) δ 7.51 (d, J=8.8 Hz, 2H), 6.89 (d, J=8.8 Hz, 2H), 6.64 (s, 1H), 5.37 (s, 2H), 4.06 (q, J=6.8 Hz, 2H), 1.57 (s, 9H), 1.41 (t, J=6.8 Hz, 3H) ppm; $^{13}$C NMR (100 MHz, DMSO) δ 164.3, 159.6, 148.4, 127.2, 126.2, 114.8, 114.5, 80.6, 63.6, 28.6, 14.8 ppm; IR (ATR) 3459, 3352, 2978, 1664, 1602, 1548, 1460 cm$^{-1}$; HRMS calcd for $C_{17}H_{21}NO_3S$ [M+H$^+$] 320.1242. found 320.1320.

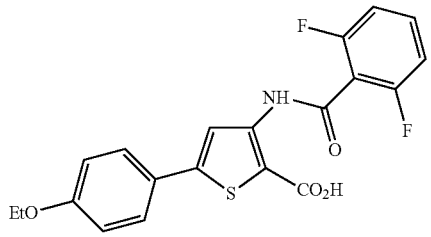 [SMILES: CCOc1ccc(-c2cc(NC(=O)c3c(F)cccc3F)c(C(=O)O)s2)cc1]

3-(2,6-Difluorobenz amido)-5-(4-ethoxyphenyl)thiophene-2-carboxylic acid (ML317, SID 126497311, CID 23602075): To a solution of tert-butyl 3-amino-5-(4-ethoxyphenyl)thiophene-2-carboxylate (0.1866 g, 0.584 mmol) and triethylamine (0.163 mL, 1.168 mmol) in dichloromethane was added 2,6-difluorobenzoyl chloride (0.103 g, 0.584 mmol) dropwise. The reaction mixture was allowed to stir overnight. Then, 1N HCl was added to the reaction mixture. The organic phase was then washed with brine, concentrated en vacuo. A 1:3 solution of trifluoroacetic acid:dichloromethane was added slowly to the residue. The reaction was allowed to stir for two hours. The reaction was then concentrated and the residue was triturated with diethyl ether, resulting in a white solid (94%, 0.221 g). $^1$H NMR (400 MHz, DMSO) δ 13.62 (s, 1H), 8.24 (s, 1H), 7.68 (d, T=6.8 Hz, 2H), 7.64 (m, 1H), 7.31 (t, J=6.8 Hz, 2H), 7.03 (d, J=7.2 Hz, 2H), 4.09 (q, J=5.6 Hz, 2H), 1.36 (t, J=5.6 Hz, 3H) ppm; $^{13}$C NMR (100 MHz, DMSO) δ 164.6, 160.2, 159.6, 158.2, 158.1, 157.0, 148.4, 142.6, 133.5, 133.3, 127.4, 124.7, 116.7, 115.2, 113.5, 112.7, 112.5, 111.1, 63.3, 14.5 ppm; IR (ATR) 3319, 2942, 2531, 1693, 1651, 1607, 1565, 1449, 1254, 1024 cm$^{-1}$; HRMS calcd for $C_{20}H_{15}F_2NO_4S$ [M+H$^+$] 404.0763. found 404.0770.

3 Results 3.1 Summary of Screening Results

Primary assay: An end-point assay to measure the amount of K1 phage-induced bacterial cell lysis was employed to determine the compound effect on capsule biogenesis. K1 bacteriophage specifically binds the bacterial capsule during the initial stages of infection. Bacteria without capsule cannot be infected and lysed by the bacteriophage. The ability of the test compounds to inhibit the K1 capsule formation was measured by an increase in the fluorescence of Alamar Blue, which correlated with the amount of intact bacterial cells compared to control reaction wells Inhibition of phage-induced lysis indicated an active compound in the primary screen. A total of 338,740 compounds were screened at 100 μM in the primary screen Inhibition of phage lysis was calculated relative to the mean of the bacterial (positive) control on each microtiter plate. Primary screen average Z values=0.75; average signal to background (S/B)=11; and average coefficient of variance=4.6%. For calculation of S/B/Z value, and CV, the following formulae (in which SD stands for standard deviation) were used: S/B=mean signal/mean background; Z=1-3SD of sample+3SD of control mean of sample−mean of control; % CV= (SD mean signal/mean signal)×100.

Confirmatory efficacy: The background cutoff (15% inhibition) for the primary screen was calculated using the mean of all compound results plus 3×SD. Compounds that inhibited more than 30% (1,767) were considered for evaluation by confirmatory dose response and cytotoxicity counter screening assays. Only 1,219 compounds were available for confirmatory assays. The confirmatory efficacy assay was performed as described for the primary screen except that each compound was tested at 10 concentration points starting from 300 μM and continuing to lower concentrations by serial 2-fold dilutions to 0.69 μM. Twenty-six compounds were confirmed as effective at inhibiting the formation of capsule at compound concentrations below 50 μM. Confirmatory screen average Z values=0.79; average signal to background (S/B)=32; and average coefficient of variance=6.4%. IC$_{50}$ values were calculated using a 4 parameter Levenburg-Marquardt algorithm, with the maximum and minimum locked at 0 and 100 respectively.

Cytotoxicity assay: The cytotoxicity assay was performed as described in Section 6: Appendix. Hit cytotoxicity and the 50% toxic concentration (CC$_{50}$) was determined and compared to the IC$_{50}$ to calculate the selectivity index. Twenty-nine compounds were tested, and 11 were inactive (CC$_{50}$>50 μM).

Outcome 3.2 Dose Response Curves for Probe

The primary assay (Summary AID: 488970) and counterscreen methods (AID: 493020); were used to measure both probe efficacy and cytotoxicity. The probe ML317 potency in the primary phase lysis inhibition assay was determined: IC$_{50}$=4.5±2.4 μM, and the CC$_{50}$ 47.2±7.2 μM. The calculated selectivity was determined as (CC$_{50}$/IC$_{50}$)=10.5. The ML317 dose response profiles for efficacy and cytotoxicity curves are graphed below (FIG. 3.2.1).

FIG. 9 and FIG. 10. Efficacy and cytotoxicity analysis of ML317. The graph on the left shows the efficacy of the probe in the primary bacterial phage lysis inhibition assay (n=3). The small gray inset magnifies the corresponding region in the larger graph. The graph on the right shows the probe cytotoxicity after a 72 hr incubation with bladder carcinoma 5637 cells (n=2).

3.3 Scaffold/Moiety Chemical Liabilities

The probe compound and analogues appears to be stable based on our observations from day-to-day handling related to their synthesis, analysis, dissolution-transfer, lyophilization, and storage. The probe compound and analogues do not contain moieties that are known or expected to be reactive. The probe was found to be stable in aqueous solution and in the presence of thiol (please see sections 2.2.4 and 2.2.5).

3.4 SAR Tables

The HTS of 338,740 compounds at 100 μM in the primary screen (AID 488966) resulted in a cluster of 20 thiophene analogues, in which one hit (CID 23602075) was discovered. Structures of six of the 19 inactive analogues as well as the active hit are shown in Table 3.4.1. In the best case, one might discern useful SAR information from the HTS data, however we found these initial data to be of limited value.

TABLE 3.4.1

HTS data for compounds in the thiophene chemotype

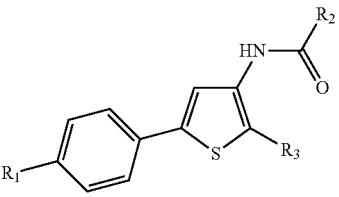

| # | CID SID | $R_1$ | $R_2$ | $R_3$ | % Inhibition at 100 μM |
|---|---------|-------|-------|-------|------------------------|
| 1 | 23602075 49649781 | EtO | 2,6-dimethoxyphenyl | $CO_2H$ | 9.12 |
| 2 | 6710528 17514982 | H | Phenyl | $CO_2Me$ | 4.18 |
| 3 | 3669658 17514946 | H | p-F-phenyl | $CO_2Me$ | 2.58 |
| 4 | 3268361 17514798 | H | 2,6-dimethoxy | $CO_2Me$ | 2.52 |
| 5 | 16012569 49668096 | H | m-F-phenyl | $CO_2Me$ | 0.19 |
| 6 | 4114774 24816444 | H | Me | $CO_2Me$ | 0.68 |
| 7 | 2814791 26728894 | Cl | o-$CO_2H$ | $CO_2Me$ | −0.17 |

To gain insight on where to focus our SAR optimization efforts, a set of 14 compounds was purchased, which included the hit itself, as well as 13 structurally related analogues. Each compound was screened thoroughly to determine $IC_{50}$ values in K1 phage, cytotoxicity, and T7 phage assays (Table 3.4.2). The sample for the original compound hit (CID 23602075, SID 103147605) gave $IC_{50}$ values in the K1 phage, cytotoxicity and T7 phage assays of 4.5±2.4 μM, 47.2±7.2 μM and <0.39 μM, respectively, with a selectivity of 10.49; all values consistent with the probe criteria. Other SAR information was discovered from this set of compounds, in that, converting the carboxylic acid to a methyl ester at the two-position of the thiophene core resulted in a loss of desired activity. This is seen in comparing entry 1 to entry 11, in which our K1 phage $IC_{50}$ went from 4.5±2.4 μM to >100 μM. Also, para-phenyl substitution was determined to be important since when $R_1$ was substituted with hydrogen instead of an ethoxy group, as in the case of comparing entry 1 to entry 10, K1 phage activity was lost with an accompanied fourfold increase in cytotoxicity. When examining $R_2$, substitutions involving halogenation gave better overall activity. The SAR observation is supported when comparing entries 4 and 5, where K1 phage, cytotoxicity, selectivity and T7 phage activity are all improved by switching a methyl group for a bromine substituent at the five position of the thiophene 2-carboxamide.

TABLE 3.4.2

Purchased Analogue series

| | | | | | | K1 phage (μM) (n = # replicated) | | | Cytotoxicity (μM) (n = # repli pcated) | | | | T7 phage (μM) | |
|---|---|---|---|---|---|---|---|---|---|---|---|---|---|---|
| # | CID SID | $R_1$ | $R_2$ | $R_3$ | n | $IC_{50}$ | $IC_{50}$ STDEV | n | $IC_{50}$ | $IC_{50}$ STDEV | Selectivity (Cyt./K1) | n | $IC_{50}$ | $IC_{50}$ STDEV |
| 1 | 23602075 103147605 | EtO | 2,6-difluorophenyl | $CO_2H$ | 3 | 4.5 | 2.4 | 2 | 47.2 | 7.2 | 10.49 | 2 | <0.39 | ND* |
| 2 | 16393058 121360790 | H | cyclopentyl | $CO_2H$ | 3 | >100 | | 2 | 169 | | ND | 2 | 56.6 | ND* |
| 3 | 16393057 121360791 | H | cyclohexyl | $CO_2H$ | 3 | >100 | | 2 | 114.6 | | ND | 2 | 65.2 | ND* |
| 4 | 17546665 121360792 | H | 2-(5-Me-thiophene) | $CO_2H$ | 3 | >100 | | 2 | 63.6 | | ND | 2 | 29.7 | ND* |
| 5 | 17546666 121360795 | H | 2-(5-Br-thiophene) | $CO_2H$ | 3 | 50.28 | 11.49 | 2 | 78.91 | 36.1 | 1.57 | 2 | 8.9 | ND* |
| 6 | 17546661 121360796 | H | 2-(3-Me-benzofuran) | $CO_2H$ | 3 | >100 | | 2 | 48.7 | | ND | 2 | 33.3 | ND* |
| 7 | 17547200 121360798 | H | 2-(5-Cl-thiophene) | $CO_2H$ | 3 | >100 | | 2 | 71.5 | | ND | 2 | 15.1 | ND* |
| 8 | 9945365 121360799 | H | 2-thiophene | $CO_2H$ | 3 | 75.39 | 10.34 | 2 | 62.01 | 38.59 | 0.82 | 2 | 6.9 | ND* |
| 9 | 17548073 121360800 | H | 2-benzofuran | $CO_2H$ | 3 | >100 | | 2 | 167.1 | | ND | 2 | 6.7 | ND* |
| 10 | 121360801 23602069 | H | 2,6-difluorophenyl | $CO_2H$ | 3 | >100 | | 2 | 10.4 | | ND | 2 | ND | ND* |
| 11 | 16012549 121360802 | EtO | 2,6-difluorophenyl | $CO_2Me$ | 3 | >100 | | 2 | >300 | | ND | 2 | ND | ND* |
| 12 | 23602077 121360803 | H | 3-Cl-phenyl | $CO_2H$ | 3 | 84.5 | 1.43 | 2 | 43.81 | 12.43 | 0.52 | 2 | 34.4 | ND* |
| 13 | 16012569 121360805 | H | 3-F-phenyl | $CO_2H$ | 3 | >100 | | 2 | 76.9 | | ND | 2 | 26.9 | ND* |
| 14 | 23602082 121360806 | EtO | 3,4-dimethoxyphenyl | $CO_2H$ | 3 | 57.94 | 2.74 | 2 | 72.31 | 14.84 | 1.25 | 2 | 8.0 | ND* |

*ND = not determined

Having exhausted the commercial supply of interesting analogues for the chemotype, the team turned to synthesis of analogues in order to expand the SAR. Given that the set of purchased compounds showed that the carboxylic acid moiety was important, we decided not to attempt to tune it further, but chose to focus on varying the 3-carboxamide and 5-aryl substituents of the thiophene core highlighted in red and blue, respectively, in FIG. 11.

Initially, 32 analogues were synthesized in parallel to assess the effects of methoxy, ethoxy, methyl, isopropyl, tert-butyl, trifluoromethyl and trifluoromethoxy aryl substitution, as well as 2,6-difluorophenyl, m-fluorophenyl, 5-bromofuran-2-yl, benzofuran-2-yl and the 5-bromothiophen-2-yl carboxamide substitution, on anti-capsule activity (Table 3.4.3). Upon screening these compounds through the same four assays as used for the purchased analogues, it was immediately noticeable that every analogue displayed statistically significant activity in the T7 phage assay. In fact, only three analogues (entries 13, 24 and 27) did not exhibit T7 phage $IC_{50}$ values within the probe criteria of <10 μM. Interestingly, these three analogues contained the benzofuran-2-yl, m-fluorophenyl and 5-bromothiophe-2-yl carboxamide moieties; features shared by many of the analogues that performed poorly in the K1 phage assay (entries 2, 8, 11, 13, 14, 18, 19, 22, 24, 26, 27, 29, 31, 32). However, quite notable activity was observed for analogues with the 2,6-difluorophenyl and 5-bromofuran-2-yl carboxamide substituents. Furthermore, the compounds shown in entries 5 (resynthesized hit), 7, 15, 17 and 30 met probe criteria ($IC_{50}$<10 μM) for both K1 phage and T7 phage anti-capsule activity, while three of these analogues (entries 5, 7 and 17) also met probe criteria for selectivity based on cytotoxicity (selectivity index >10). Lastly, when examining the aryl substitution, there was an activity trend, in which ethoxy>methoxy>methyl≈tert-butyl, which is evident when examining entries 3, 7, 12 and 17. In Table 3.4.3, confirmatory assay efficacy and standard deviations are provided for all compounds with determined $IC_{50}$ values.

TABLE 3.4.3

First Round of Synthetic Analogues

| # | CID SID | $R_1$ | $R_2$ | K1 phage (μM) (n = # replicated) | | | Cytotoxicity (μM) (n = # replicated) | | | Selectivity (Cyt./K1) | T7 phage (μM) | | |
|---|---|---|---|---|---|---|---|---|---|---|---|---|---|
| | | | | n | $IC_{50}$ | $IC_{50}$ STDEV | n | $IC_{50}$ | $IC_{50}$ STDEV | | n | $IC_{50}$ | $IC_{50}$ STDEV |
| 1 | 53470430 126497317 | MeO | 2,6-difluorophenyl | 3 | >100 | | 3 | 238.8 | | ND | 2 | 2.645 | ND* |
| 2 | 53470445 126497316 | MeO | m-F-phenyl | 3 | >100 | | 3 | 44.77 | | ND | 2 | 8.36 | ND* |
| 3 | 53470446 126497314 | MeO | 5-Br-furan-2-yl | 3 | 11.11 | 3.33 | 3 | 50.48 | 0.52 | 4.55 | 2 | 1.235 | ND* |
| 4 | 53470443 126497315 | MeO | Benzofuran-2-yl | 3 | >100 | | 3 | 44.77 | | ND | 2 | 8.36 | ND* |
| 5 | 23602075 126497311 | EtO | 2,6-difluorophenyl | 3 | 1.89 | 1.56 | 3 | 51.6 | 13.69 | 27.3 | 2 | <0.625 | ND* |
| 6 | 23602076 126497308 | EtO | m-F-phenyl | 3 | 14.68 | 2.31 | 3 | 61.34 | 5.86 | 4.18 | 2 | 2.61 | ND* |
| 7 | 23602086 126497309 | EtO | 5-Br-furan-2-yl | 3 | 3.42 | 1.55 | 3 | 68.71 | 7.42 | 20.09 | 2 | <0.625 | ND* |
| 8 | 53470427 126497310 | EtO | Benzofuran-2-yl | 3 | >100 | | 3 | 193.17 | | ND | 2 | 2.75 | ND* |
| 9 | 53470415 126497312 | EtO | 5-Br-thiophen-2-yl | 3 | 17.03 | 4.49 | 3 | 49.72 | 6.49 | 2.92 | 2 | 3.335 | ND* |
| 10 | 53470422 126497338 | Me | 2,6-difluorophenyl | 3 | 40.26 | 26.84 | 3 | 57.29 | 2.76 | 1.42 | 2 | 2.425 | ND* |
| 11 | 53470441 126497320 | Me | m-F-phenyl | 3 | 53.73 | 13.07 | 3 | 43.94 | 6.41 | 0.82 | 2 | 7.205 | ND* |
| 12 | 53470423 126497319 | Me | 5-Br-furan-2-yl | 3 | 15.7 | 6.14 | 3 | 50.72 | 4.04 | 3.23 | 2 | 1.0125 | ND* |
| 13 | 53470436 126497337 | Me | Benzofuran-2-yl | 3 | >100 | | 3 | 94.58 | | ND | 2 | 19.955 | ND* |
| 14 | 53470429 126497321 | Me | 5-Br-thiophen-2-yl | 3 | >50 | | 3 | 64.04 | | ND | 2 | 10.73 | ND* |
| 15 | 53470439 126797324 | i-Pr | 2,6-difluorophenyl | 3 | 7.09 | 2.7 | 3 | 32.36 | 2.83 | 4.56 | 2 | 1.27 | ND* |
| 16 | 53470444 126497323 | i-Pr | m-F-phenyl | 3 | 24.82 | 9.14 | 3 | 37.55 | 2.31 | 1.51 | 2 | 2.81 | ND* |
| 17 | 53470420 126497336 | i-Pr | 5-Br-furan-2-yl | 3 | 3.075 | 0.37 | 3 | 50.35 | 8.46 | 16.37 | 2 | 1.245 | ND* |
| 18 | 53470434 126497322 | i-Pr | Benzofuran-2-yl | 3 | 42.88 | 27.32 | 3 | 47.18 | 6.4 | 1.10 | 2 | 2.705 | ND* |
| 19 | 53470432 126497325 | i-Pr | 5-Br-thiophen-2-yl | 3 | >100 | | 3 | 33.06 | | ND | 2 | 2.745 | ND* |

TABLE 3.4.3-continued

First Round of Synthetic Analogues

| | | | | K1 phage (μM) (n = # replicated) | | Cytotoxicity (μM) (n = # replicated) | | | T7 phage (μM) | | |
|---|---|---|---|---|---|---|---|---|---|---|---|
| # | CID SID | $R_1$ | $R_2$ | n | $IC_{50}$ | $IC_{50}$ STDEV | n | $IC_{50}$ | $IC_{50}$ STDEV | Selectivity (Cyt./K1) | n | $IC_{50}$ | $IC_{50}$ STDEV |
| 20 | 53470433 126497329 | t-Bu | 2,6-difluorophenyl | 3 | 11.53 | 6.42 | 3 | 35.07 | 7.5 | 3.04 | 2 | 1.635 | ND* |
| 21 | 53470435 126497328 | t-Bu | m-F-phenyl | 3 | 19.88 | 14.36 | 3 | 21.12 | 0.76 | 1.06 | 2 | 2.7 | ND* |
| 22 | 53470424 126497327 | t-Bu | Benzofuran-2-yl | 3 | >100 | | 3 | 34.47 | | ND | 2 | 2.825 | ND* |
| 23 | 53470440 126497333 | $F_3C$ | 2,6-difluorophenyl | 3 | 23.67 | 3.84 | 3 | 44.77 | 0.73 | 1.89 | 2 | 3.8 | ND* |
| 24 | 53470418 126497332 | $F_3C$ | m-F-phenyl | 3 | >100 | | 3 | 35.13 | | ND | 2 | 12.79 | ND* |
| 25 | 53470416 126497331 | $F_3C$ | 5-Br-furan-2-yl | 3 | 12.29 | 3.61 | 3 | 47.52 | 14.03 | 3.87 | 2 | 2.59 | ND* |
| 26 | 53470417 126497335 | $F_3C$ | Benzofuran-2-yl | 3 | >100 | | 3 | 72.06 | | ND | 2 | 7.175 | ND* |
| 27 | 53470428 126497334 | $F_3C$ | 5-Br-thiophen-2-yl | 3 | >50 | | 3 | 38.52 | | ND | 2 | 14.12 | ND* |
| 28 | 53495055 126722926 | $F_3CO$ | 2,6-difluorophenyl | 3 | 13.02 | 4.6 | 3 | 51.01 | 2.62 | 3.92 | 2 | 1.355 | ND* |
| 29 | 53495056 126722925 | $F_3CO$ | m-F-phenyl | 3 | >100 | | 3 | 52.14 | | ND | 2 | >5 | ND* |
| 30 | 53495057 126722927 | $F_3CO$ | 5-Br-furan-2-yl | 3 | 6.39 | 1.73 | 3 | 33.62 | 2.88 | 5.26 | 2 | 1.165 | ND* |
| 31 | 53495058 126722924 | $F_3CO$ | Benzofuran-2-yl | 3 | >100 | | 3 | 40.63 | | ND | 2 | 3.83 | ND* |
| 32 | 53495054 126722928 | $F_3CO$ | 5-Br-thiophen-2-yl | 3 | >100 | | 3 | 20.45 | | ND | 2 | 2.695 | ND* |

Since, overall, ethoxy aryl substitution gave better activity than methoxy aryl substitution, the team chose to homologate this group further to see if the trend would continue. Trifluoroalkylation at the aryl position was also studied in order to anticipate PK issues that might be associated with hydrocarbon chain elongation. Thirdly, because halogenation of carboxamide substituents provided useful anti-capsule activity, we further halogenated at these sites (Table 3.4.3). In every case, except in comparing entries 15 to 16, adding additional halogen groups resulted in a drastic loss in activity in the K1 phage assay. We also found that hydrocarbon chain elongation resulted in more potent analogues as exemplified by comparing the K1 phage activity of CID 53470446, CID 23602086 and 56643021 (entry 9) that gave $IC_{50}$ values of 11.11 μM, 3.42 μM and 0.85 μM, respectively, as well as comparing the K1 phage activity of CID 53470430, CID 23602075 and CID 56643007 (entry 7) that gave $IC_{50}$ values of >100 μM, 1.89 μM and <0.78 μM, respectively. This trend was somewhat mirrored with the trifluoro analogues in that, while examining the 2,6-difluorophenylcarboxamide series, in comparing trifluoromethoxy (CID 53495055), trifluoroethoxy (CID 56643002, entry 4), and trifluoropropoxy (CID 56643020, entry 1), the activity increased in the K1 phage assay as chain length increased with $IC_{50}$ values of 13.02 μM, 2.86 μM and 0.84 μM, respectively. However, when increasing the chain length one more carbon unit as seen in the trifluorobutoxy analogue, the K1 phage $IC_{50}$ value increased to 10.32 μM.

This final round of SAR has resulted in the most potent analogue to date, entry 1, Table 3.4.3, exhibiting a K1 phage $IC_{50}$ of 0.84 μM, a cytotoxicity $IC_{50}$ of 68.41 μM, a selectivity index of 81.44 and a T7 phage $IC_{50}$ of <0.156 μM.

TABLE 3.4.3

Second Round of Synthetic Analogues

| | CID SID | $R_1$ | $R_2$ | n | IC$_{50}$ K1 phage (μM) | STDEV | n | IC$_{50}$ Cytotoxicity (μM) | STDEV | Selectivity (Cyt./K1) | n | IC$_{50}$ T7 phage (μM) | STDEV |
|---|---|---|---|---|---|---|---|---|---|---|---|---|---|
| 1 | 56643020 134419017 | n-trifluoropropoxy | 2,6-difluorophenyl | 3 | 0.84 | 0.51 | 3 | 68.41 | 5.49 | 81.44 | 2 | <.0156 | ND* |
| 2 | 56643010 134419022 | n-trifluoropropoxy | 2,4,6-trifluorophenyl | 3 | 3.11 | 0.86 | 3 | 63.63 | 4.22 | 20.46 | 2 | <0.625 | ND* |
| 3 | 56643022 134419009 | n-trifluoropropoxy | 5-Br-furan-2-yl | 3 | 0.84 | 0.66 | 3 | 41.67 | 1.26 | 49.61 | 2 | <0.625 | ND* |
| 4 | 56643002 134419021 | trifluoroethoxy | 2,6-difluorophenyl | 3 | 2.86 | 1.25 | 3 | 75.18 | 9.85 | 26.29 | 2 | <0.625 | ND* |
| 5 | 56643012 134419020 | trifluoroethoxy | 2,4,6-trifluorophenyl | 3 | 94.94 | 7.58 | 3 | 161.1 | 11.58 | 1.7 | 2 | 2.5-5 | ND* |
| 6 | 56643003 134419010 | trifluoroethoxy | 5-Br-furan-2-yl | 3 | 4.90 | 1.20 | 3 | 50.0 | 3.65 | 10.2 | 2 | 0.625 | ND* |
| 7 | 56643007 134419008 | n-butoxy | 2,6-difluorophenyl | 3 | <0.78 | | 3 | 42.63 | | >54.65 | 2 | <0.625 | ND* |
| 8 | 56643023 134419018 | n-propoxy | 2,4,6-trifluorophenyl | 3 | 8.06 | 2.75 | 3 | 85.57 | 8.12 | 10.62 | 2 | <0.625 | ND* |
| 9 | 56643021 134419012 | n-butoxy | 5-Br-furan-2-yl | 3 | 0.85 | 1.07 | 3 | 43.43 | 2.58 | 51.09 | 2 | <0.625 | ND* |
| 10 | 56643019 134419014 | n-butoxy | 4,5-dibromo-furan-2-yl | 3 | 23.26 | 2.65 | 3 | 31.66 | 4.97 | 1.36 | 2 | 1.25-2.5 | ND* |
| 11 | 56643016 134419019 | n-propyl | 2,6-difluorophenyl | 3 | 2.63 | 1.40 | 3 | 54.87 | 6.88 | 20.86 | 2 | <0.625 | ND* |
| 12 | 56643011 134419023 | n-propyl | 2,4,6-trifluorophenyl | 3 | 15.88 | 2.39 | 3 | 69.9 | 12.41 | 4.4 | 2 | 2.5-5 | ND* |
| 13 | 56643013 134419007 | n-propyl | 5-Br-furan-2-yl | 3 | 1.43 | 0.88 | 3 | 46.39 | 3.77 | 32.44 | 2 | <0.625 | ND* |
| 14 | 56643005 134419011 | n-propyl | 4,5-dibromo-furan-2-yl | 3 | 6.78 | 0.95 | 3 | 40.99 | 2.53 | 6.05 | 2 | <5.0 | ND* |
| 15 | 56643024 134419031 | n-trifluorobutoxy | 2,6-difluorophenyl | 3 | 10.32 | 2.21 | 3 | 241.21 | 12.68 | 23.37 | 2 | <2.5 | ND* |
| 16 | 56643015 134419016 | n-trifluorobutoxy | 2,4,6-trifluorophenyl | 3 | 5.53 | 5.84 | 3 | 54.72 | 7.81 | 9.9 | 2 | <1.25 | ND* |
| 17 | 56643008 134419013 | n-trifluorobutoxy | 5-Br-furan-2-yl | 3 | 1.78 | 0.50 | 3 | 38.69 | 1.69 | 21.74 | 2 | <2.5 | ND* |
| 18 | 56643009 134419030 | n-trifluorobutoxy | 4,5-dibromo-furan-2-yl | 3 | >100 | | 3 | 250.98 | | ND | 2 | <2.5 | ND* |
| 19 | 56643025 134419029 | n-Azidoethoxy | 2,6-difluorophenyl | 3 | 17.52 | 3.68 | 3 | 273.32 | 26.84 | 15.6 | 2 | <0.625 | ND* |
| 20 | 56643017 134419004 | Ethoxy | 2-trifluoromethyl-6-fluorophenyl | 3 | 52.59 | 5.75 | 3 | 62.03 | 7.91 | 1.18 | 2 | <5 | ND* |
| 21 | 56643006 134419025 | Ethoxy | 2,4,6-trifluorophenyl | 3 | 19.99 | 2.48 | 3 | 76.62 | 6.82 | 3.83 | 2 | <5 | ND* |

*ND = not determined

Probe Selection:

Several compounds generated during these studies met the criteria established at the outset of the project for a useful probe compound. Early in the project, however, ML317 was found to have good activity across the suite of assays used to define the probe criteria and in a suite of in vitro PK assays. In addition, in PubChem, the probe ML317 is reported to have shown activity in only 16 of 341 bioassays in which it was tested (4.7% hit rate), which suggests that ML317 is not a promiscuous hitter. In as much, this compound was used for advanced, preliminary studies such as those described in sections 3.5, 4.2, and 4.3. In any case, as was mentioned previously, quite a number of useful compounds were identified across the ML317 chemotype, and, depending on the specific intended use for these compounds, many of them could have been chosen as probes (for example, CID56643007, entry 7, Table 3.4.3; CID56643020, entry 1, Table 3.4.3; CID56643021, entry 9, Table 3.4.3 and CID56643022, entry 3, Table 3.4.3).

3.5 Cellular Activity

ML317 was identified using a phenotypic bacterial cell-based assay that determined the amount of bacterial capsule formation in the presence of the probe compound. No biochemical assays were used for determination of compound biological activity. Additional cell-based assays were performed to determine probe specificity. Also, a counter-assay was performed to determine eukaryotic cytotoxicity using human bladder cell carcinoma 5637 cells, which are considered the physiologically-relevant target cell type. The compound was shown to have no effect on bacterial cell viability in the highest tested concentration (100 µM), and the cytotoxic concentration was 47.2±7.2 µM, which determined a calculated selective index of 10.5. Although the primary and secondary assays were performed using bacterial cultures, it is recognized that probe will be used in in vitro eukaryotic and in vivo assay systems. Because of this, each synthesized probe and analogs were routinely tested using the cytotoxicity counterassay.

3.6 Profiling Assays

In Vitro Pharmacokinetics Profiling:

The in vitro pharmacokinetic (PK) properties of the probe (ML317) were profiled using a standard panel of assays (Table 3.6.2) across which the probe displayed encouraging results.

Targeting factors required by microbial pathogens almost exclusively during infection, so called anti-virulence therapeutics, is predicted to dramatically reduce chemical stress on commensal microbes and thus lessen the emergence of resistance. Furthermore, many infections may be cleared by inhibiting microbial factors that subvert the host immune response, thus allowing natural clearance of the infection and possibly enhancing immune memory of the infectious agent to allow the immune system to better recognize and clear subsequent infections. Since the vast majority of UTI occur in the community in other healthy individuals with competent immune systems, this strategy for novel anti-virulence agents is rationale and practical.

TABLE 3.6.2

Summary of in vitro ADME properties of ML317

| Aqueous Solubility$^a$ (µg/mL, µM) | Assay Media Solubility$^b$ (µg/mL, µM) | PAMPA Pe$^c$ ($\times 10^{-6}$ cm/s @ Donor pH) | Plasma Protein Binding (% Bound) | | Plasma Stability$^d$ Human Mouse/1:1 Plasma:PBS | Hepatic Microsome Stability$^e$ Human/ Mouse | Hepatic Toxicity$^f$ LC$_{50}$ (µM) |
|---|---|---|---|---|---|---|---|
| | | | Human 1 µM/10 µM | Mouse 1 µM/10 µM | | | |
| 93/229 | 68/169 | 14 @ 5.0 209 @ 6.2 52 @ 7.4 | 99.68/99.85 | 98.97/99.31 | 95.3/78.4 | 89.6/74.3 | 26 |

$^a$in 1x PBS, pH 7.4
$^b$in Luria-Bertani broth (10 g tryptone, 5 g yeast extract, 10 g NaCl)
$^c$in aqueous buffer (pION),; Donor compartment pH 5.0/6.2/7.4; Acceptor compartment pH 7.4 @ RT
$^d$% remaining at 3 hr @ 37° C.
$^e$% remaining at 1 hr @ 37° C.
$^f$towards Fa2N-4 immortalized human hepatocytes Broad-spectrum Target Profiling:

The probe compound ML317 was submitted to Ricerca for LeadProfiling to assess off-target pharmacology. The probe was tested in duplicate at 10 µM concentration and no significant activity was noted across the panel of 67 targets (i.e., <50% inhibition, see Appendix 2 for the complete list of results). In addition, in PubChem, the probe ML317 is reported to have shown activity in only 16 of 341 (4.7%) bioassays in which it was tested. These results suggest that ML317 is not a promiscuous compound with respect to off-target effects.

4 Discussion 4.1 Comparison to Existing Art and how the New Probe is an Improvement Traditional anti-infectives for the treatment of UTI are almost exclusively directed toward inhibiting central metabolic and structural targets such as folate metabolism, protein synthesis, DNA replication machinery, and cell wall assembly. Traditional targets of inhibition are attractive because of the potential broad spectrum of inhibition of a variety of organisms. However, the lack of specificity then also means that microbes not involved in an infectious process and not intended as targets of the therapeutic are indiscriminately targeted. The major consequences are twofold: 1) Normal flora are eliminated, resulting in side effects such as antibiotic-associated diarrhea and the emergence of pathogens such as Clostridium difficile, and 2) stress within microbial reservoirs such as the enteric tract drives the acquisition and emergence of antibiotic resistance. Furthermore, more traditional anti-infectives are not disease specific, and thus the multiplicity of their use for a variety of infection prevention and treatment increases the amount of human and agricultural exposure to these agents, further driving antibiotic resistance.

The probe described herein is entirely novel with the only precedent being the structurally dissimilar molecule 2-(4-phenylphenyl)benzo[g]quinoline-4-carboxylic acid that we previously described in proof-of-concept studies (33). The probe described herein is uniquely poised for development as an infection-specific prevention and treatment therapeutic that enhances natural immune clearance of an infection, namely UTI. The highly soluble probe abrogates capsule development in several K type UPEC as demonstrated through capsule-specific phage assays and orcinol biochemical tests. However, the probe has no effect on in vitro growth and viability of UPEC in the absence of immune factors. Unlike with many traditional antibiotics, exposure of UPEC to a range of concentrations of the probe has not resulted in the emergence of spontaneous resistance in the laboratory, consistent with the concept that this probe does not induce stress and adaptive changes that confer resistance. Furthermore, this probe would be expected to act upon traditional antibiotic resistant strains of E. coli.

As previously outlined, 2-(4-phenylphenyl)-benzo[g]quinoline-4-carboxylic acid C7, was used as the prototype small-molecule inhibitor of capsule biogenesis and serves as the only prior art for this probe development project. The probe discovered during this MLPCN project demonstrates improved potency in the K1 phage assay, a better selectivity index, similar performance in the orcinol screen, and greater than an order-of-magnitude lower IC$_{50}$ value in the T7 phage assay (FIG. 12). Furthermore, we have demonstrated the synthetic tractability for the ML317 chemotype, and prepared an array of highly active analogues, whereas C7 does not share either of positive these attributes. We feel these factors to be of utmost importance, since these compounds are believed to have a unified mode of action. To further demonstrate the usefulness of ML317 as a probe, we have shown ML317 to have good in vitro pharmacokinetic properties. Aqueous stability in 1×PBS at pH 7.4, aqueous stability in LB, both human and mouse hepatic microsomal stability, PAMPA permeability and both human and mouse stability were all found to be good. In contrast, while C7 has not been screened in such in vitro PK assays, one might predict poor results. For example, one would not imagine a compound such as C7 to have good solubility characteristics. Lastly, the many aryl rings of the C7 structure pose liabilities to oxidative metabolism that might render this compound less attractive compared to ML317.

Mechanism of Action Studies

Studies to date indicate that UPEC treatment with the probe results in significantly reduced transcript for the capsule genes from each of the two major promoters. These data suggest that the ultimate mechanism through which capsule expression is inhibited is by reduction of transcription. Genetic studies of the currently known regulators of both capsule promoters have not indicated their role in this process, suggesting an alternative regulatory system is responsible.

Moving forward, genetic and biochemical approaches are being employed to identify the mechanism of action. Currently, overexpression of a whole genome open reading frame library of E. coli is being used to identify gene products that enhance or reduce susceptibility to the probe. The screen is expected to select transporters of the probe and a regulatory target that interacts with the probe. The target of the probe may be within a signal transduction pathway to capsule regulation but distinct from the actual transcription factor affecting capsule expression. Cellular localization of probe-interacting factors and biochemical studies of probe-target interactions will be explored.

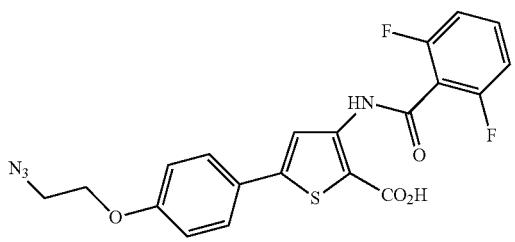

SID134419029. Azide derivative of probe for copper-free click chemical modification Through the SAR around DU011, SID134419029 (shown), an azide derivative of ML317, has been synthesized that is amenable to copper-free click chemistry to permit straightforward additions of R groups including biotin and fluorophore labels. Preliminary studies indicate that this DU011 analogue retains substantial capsule inhibitor activity with an approximate $IC_{50}$ of 17 μM. Using a fluorophore labeled derivative, the localization of the compound (outer membrane, periplasm, inner membrane, or cytoplasm) will be determined by microscopy. A biotinylated derivative will be employed for affinity isolation of the target using bacterial fractions to which the probe localizes. Mass spectrometry will be used to identify the target. Biochemical and genetic studies will be used to elucidate the interaction between the probe and putative target.

Recent studies have also employed chemical mutagenesis to derive strains resistant to the action of the probe. Whole genome sequencing using Illumina Hiseq technology has been completed on five independent isolates. An analysis of polymorphisms shared among independent resistant bacterial clones will be used to localize putative factors that interact with the probes. These may be transporters or the actual target of the probe. The genes from the mutant and wild type strains will be cloned and expressed in the isogenic bacterial backgrounds to ascertain their roles in sensitivity to the probe. The biochemical affinity tools described earlier in this section may then be used to examine direct interactions of the probe with these resistance-associated factors.

4.3 Planned Future Studies

The probe will be advanced through medicinal chemistry to improve in vitro pharmacokinetics and biological activity. Subsequently, in vivo pharmacokinetic measurements will be collected in a murine preclinical murine model with additional optimization of the probe for bioavailability and renal excretion. After completion of these studies and refinements to the probe, the refined probe will be employed in prophylaxis and treatment trials using preclinical murine infection models of E. coli urinary tract infection and bloodstream infection.

References Section 1

5 References

1. Spellberg B, Guidos R, Gilbert D, Bradley J, Boucher H W, et al. (2008) The epidemic of antibiotic-resistant infections: a call to action for the medical community from the Infectious Diseases Society of America. Clinical infectious diseases: an official publication of the Infectious Diseases Society of America 46: 155-164.
2. Foxman B (2010) The epidemiology of urinary tract infection. Nature reviews Urology 7: 653-660.
3. Smith P A, Romesberg F E (2007) Combating bacteria and drug resistance by inhibiting mechanisms of persistence and adaptation. Nature chemical biology 3: 549-556.
4. Ali, A. S., Townes, C. L., Hall, J., and Pickard, R. S. (2009) Maintaining a sterile urinary tract: the role of antimicrobial peptides, J Urol 182, 21-28.
5. Anderson, G. G., Palermo, J. J., Schilling, J. D., Roth, R., Heuser, J., and Hultgren, S. J. (2003) Intracellular bacterial biofilm-like pods in urinary tract infections, Science 301, 105-107.
6. Bahrani-Mougeot, F. K., Buckles, E. L., Lockatell, C. V., Hebel, J. R., Johnson, D. E., Tang, C. M., and Donnenberg, M. S. (2002) Type 1 fimbriae and extracellular polysaccharides are preeminent uropathogenic Escherichia coli virulence determinants in the murine urinary tract, Mol Microbiol 45, 1079-1093.
7. Mushtaq, N., Redpath, M. B., Luzio, J. P., and Taylor, P. W. (2005) Treatment of experimental Escherichia coli infection with recombinant bacteriophage-derived capsule depolymerase, J Antimicrob Chemother 56, 160-165.
8. Olson, R. P., Harrell, L. J., and Kaye, K. S. (2009) Antibiotic resistance in urinary isolates of Escherichia coli from college women with urinary tract infections, Antimicrob Agents Chemother 53, 1285-1286.
9. Warren, J. W., Abrutyn, E., Hebel, J. R., Johnson, J. R., Schaeffer, A. J., and Stamm, W. E. (1999) Guidelines for antimicrobial treatment of uncomplicated acute bacterial cystitis and acute pyelonephritis in women. Infectious Diseases Society of America (IDSA), Clin Infect Dis 29, 745-758.
10. Gupta, K., Hooton, T. M., and Stamm, W. E. (2005) Isolation of fluoroquinolone-resistant rectal Escherichia coli after treatment of acute uncomplicated cystitis, J Antimicrob Chemother 56, 243-246.

11. Karlowsky, J. A., Hoban, D. J., Decorby, M. R., Laing, N. M., and Zhanel, G. G. (2006) Fluoroquinolone-resistant urinary isolates of *Escherichia coli* from outpatients are frequently multidrug resistant: results from the North American Urinary Tract Infection Collaborative Alliance-Quinolone Resistance study, Antimicrob Agents Chemother 50, 2251-2254.
12. Hames, L., and Rice, C. E. (2007) Antimicrobial resistance of urinary tract isolates in acute uncomplicated cystitis among college-aged women: choosing a first-line therapy, J Am Coll Health 56, 153-156.
13. Hillier S, Roberts Z, Dunstan F, Butler C, Howard A, et al. (2007) Prior antibiotics and risk of antibiotic-resistant community-acquired urinary tract infection: a case-control study. The Journal of Antimicrobial Chemotherapy 60: 92-99.
14. Schappert, S. M. (1994) National Ambulatory Medical Care Survey: 1991 summary, Vital Health Statistics 13, 1-110.
15. Gupta, K., Scholes, D., and Stamm, W. E. (1999) Increasing prevalence of antimicrobial resistance among uropathogens causing acute uncomplicated cystitis in women, JAMA 281, 736-738.
16. Kahlmeter, G. (2000) The ECO.SENS Project: a prospective, multinational, multicentre epidemiological survey of the prevalence and antimicrobial susceptibility of urinary tract pathogens—interim report, J Antimicrob Chemother 46 Suppl 1, 15-22; discussion 63-15.
17. Manges, A. R., Johnson, J. R., Foxman, B., O'Bryan, T. T., Fullerton, K. E., and Riley, L. W. (2001) Widespread distribution of urinary tract infections caused by a multidrug-resistant *Escherichia coli* clonal group, N Engl J Med 345, 1007-1013.
18. Talan, D. A., Stamm, W. E., Hooton, T. M., Moran, G. J., Burke, T., Iravani, A., Reuning-Scherer, J., and Church, D. A. (2000) Comparison of ciprofloxacin (7 days) and trimethoprim-sulfamethoxazole (14 days) for acute uncomplicated pyelonephritis pyelonephritis in women: a randomized trial, JAMA 283, 1583-1590.
19. Hultgren, S. J. (2001) Uropathogenic *escherichia coli*: interactions with bladder epithelium, Urology 57, 105-106.
20. Hultgren, S. J., Porter, T. N., Schaeffer, A. J., and Duncan, J. L. (1985) Role of type 1 pili and effects of phase variation on lower urinary tract infections produced by *Escherichia coli*, Infect Immun 50, 370-377.
21. Martinez, J. J., Mulvey, M. A., Schilling, J. D., Pinkner, J. S., and Hultgren, S. J. (2000) Type 1 pilus-mediated bacterial invasion of bladder epithelial cells, EMBO J 19, 2803-2812.
22. Justice, S. S., Hunstad, D. A., Seed, P. C., and Hultgren, S. J. (2006) Filamentation by *Escherichia coli* subverts innate defenses during urinary tract infection, Proc Natl Acad Sci USA 103, 19884-19889.
23. Anderson, G. G., Goller, C. C., Justice, S., Hultgren, S. J., and Seed, P. C. Polysaccharide capsule and sialic acid-mediated regulation promote biofilm-like intracellular bacterial communities during cystitis, Infect Immun 78, 963-975.
24. Justice, S. S., Lauer, S. R., Hultgren, S. J., and Hunstad, D. A. (2006) Maturation of intracellular *Escherichia coli* communities requires SurA, Infect Immun 74, 4793-4800.
25. Wright, K. J., Seed, P. C., and Hultgren, S. J. (2007) Development of intracellular bacterial communities of uropathogenic *Escherichia coli* depends on type 1 pili, Cell Microbiol 9, 2230-2241.
26. Rosen, D. A., Hooton, T. M., Stamm, W. E., Humphrey, P. A., and Hultgren, S. J. (2007) Detection of intracellular bacterial communities in human urinary tract infection, PLoS Med 4, e329.
27. Johnson, J. R. (1991) Virulence factors in *Escherichia coli* urinary tract infection, Clin Microbiol Rev 4, 80-128.
28. Roberts, I. S. (1995) Bacterial polysaccharides in sickness and in health. The 1995 Fleming Lecture, Microbiology 141 (Pt 9), 2023-2031.
29. Roberts, I. S. (1996) The biochemistry and genetics of capsular polysaccharide production in bacteria, Annu Rev Microbiol 50, 285-315. Llobet, E., Tomas, J. M., and Bengoechea, J. A. (2008) Capsule polysaccharide is a bacterial decoy for antimicrobial peptides, Microbiology 154, 3877-3886.
31. Mulvey, M. A., Schilling, J. D., and Hultgren, S. J. (2001) Establishment of a persistent *Escherichia coli* reservoir during the acute phase of a bladder infection, Infect Immun 69, 4572-4579.
32. Vimr, E. R., Aaronson, W., and Silver, R. P. (1989) Genetic analysis of chromosomal mutations in the polysialic acid gene cluster of *Escherichia coli* K1, J Bacteriol 171, 1106-1117.
33. Goller, C. C., and Seed, P. C. (2010) High-throughput identification of chemical inhibitors of *E. coli* Group 2 capsule biogenesis as anti-virulence agents, PLoS One 5, e11642.
34. Gopinathan, S., Nouraldeen, A., Wilson, A. G. E. (2010) Development and application of a highthroughput formulation screening strategy for oral administration in drug discovery, Future Medicinal Chemistry 2, 1391-1398.
35. Ploemen, J. H., Van Schanke, A., Van Ommen, B., and Van Bladeren, P. J. (1994) Reversible conjugation of ethacrynic acid with glutathione and human glutathione S-transferase P1-1, Cancer Res 54, 915-919.
36. Romagnoli, R., Baraldi, P. G., Remusat, V., Carrion, M. D., Cara, C. L., Preti, D., Fruttarolo, F., Pavani, M. G., Tabrizi, M. A., Tolomeo, M., Grimaudo, S., Balzarini, J., Jordan, M. A., and Hamel, E. (2006) Synthesis and biological evaluation of 2-(3',4',5'-trimethoxybenzoyl)-3-amino 5-aryl thiophenes as a new class of tubulin inhibitors, J Med Chem 49, 6425-6428.
37. Gokaraju, G. R. e. a. (2010) Preparation of triazene analogs useful in treatment of metastatic malignant melanoma and other cancers, PCT Int. Appl. 2010029577.
38. Noah, J. W., Severson, W., Noah, D. L., Rasmussen, L., White, E. L., and Jonsson, C. B. (2007) A cell-based luminescence assay is effective for high-throughput screening of potential influenza antivirals, Antiviral Res 73, 50-59.

Appendix Section 1

Appendix 6.1 Detailed Assay Descriptions 6.1.a Screening for Inhibitors of Bacterial Capsule Biogenesis.

Purpose: The primary screening was conducted to screen the MLSMR 300K compound library for selection of 1,767 hit compounds.

Summary AID: 488966

Assigned AID: 488970

Assay Description: Screening for Inhibitors of Bacterial Capsule Biogenesis.

Primary assay: The primary assay was conducted in the 1,536 well plate format. Bacterial cultures of *E. coli* K1 strain UTI89 (cystitis isolate) and isogenic capsule mutant strains (as controls for phage infection) were grown and prepared at the screening center immediately prior to use.

Overnight starting cultures of UTI89 were grown at 37° C., and inoculated into 1 liter of LB (starting $OD_{600}$~0.03), which was sufficient for screening 40 plates (including ~10% waste) and ~40,000 compounds as single points.

Control wells contained UTI89 (wt K1) with 0.5% DMSO as a simulated positive control; UTI89 with 0.5% DMSO and tetracycline for a negative growth control; and media plus vehicle control. 50 mL of LB Broth was inoculated with stock 150 μL E. coli UT189 and grown overnight at 37° C. The next day, cultures were diluted 1:75 in 1 L of LB Broth containing 0.5% DMSO. 3 μL of this culture was added to each plate well, and plates were incubated, inverted, at 37° C. for 2 hr. The K1F bacteriophage stock was diluted 1:8 in LB Broth containing 0.5% DMSO, and 1.5 μL of diluted phage (or media only) was added to the pre-plated test compound wells and appropriate control wells. The plates were centrifuged briefly, and then were incubated, inverted, at 37° C. for an additional 2 hr. Afterward, Alamar Blue reagent (Invitrogen, #DAL1100) was diluted 1:2 with LB broth and 1 μL was added to each plate well. The plates were again centrifuged briefly, and then were further incubated, inverted, at 37° C. for 30 min.

Single Dose Compound Preparation: For single dose screening, compounds or carrier control (DMSO) were diluted to a final well concentration of 1:200 in assay media. Compounds (45 nL in 100% DMSO) were dispensed to assay plates using an Echo non-contact dispenser. Compounds from the libraries were added to the plates at a final concentration of 100 μM, before the addition of bacteria or phage. Each compound was tested as a single point, and ~1200 compounds were tested per plate. The entire primary screening campaign was divided into eight batches, each screened in this manner.

Control Drug: The positive control drug C7 in 1% DMSO (2-(4-phenylphenyl)benzo[g]quinoline-4-carboxylic acid) that was previously identified in a pilot screen was not used in the primary screen due to aqueous insolubility. Tetracycline (50 μM) was used as a negative growth control drug.

Endpoint Read: The plates were read at ambient temperature from the top for fluorescence intensity in an Envision plate reader (Perkin Elmer) by excitation at 560 nm and emission at 590 nm, and the degree of phage-mediated lysis was determined based on the metabolic processing of Alamar Blue by live bacterial cells. A positive hit was defined by the compound producing greater than a 50% inhibition of phage-induced lysis.

Dose Response Compound Preparation:

Concentration dependent confirmatory and cytotoxicity assays. Dose response testing (dose range=300-0.58 μM) was used to confirm and characterize the primary screen hits, which was necessary to determine the number of compounds advanced to secondary screens.

Efficacy: Compounds were plated in 1536-well microplates, and the dose response efficacy assay was performed as described for the primary screen, with the exception that each compound was tested in duplicate at 10 concentration points starting from 300 μM and continuing to lower concentrations by 2-fold serial dilutions. The strain UTI89 delta-kpsM, a K1 capsule export mutant, was evaluated with the wt strain as a phage insensitive control (mimicking 100% capsule inhibition).

6.1.b Counterscreen: Cytotoxicity screening for potential Inhibitors of Bacterial Capsule Biogenesis.

Purpose: This cell-based assay measures the cytotoxicity of compounds in bladder carcinoma 5637 cells using luminescent cell viability assay readout.

Summary AID: 488970

Assigned AID: 493020, 504769, 504831, 588399

Assay Description: Cytotoxicity: Dose response testing (dose range=300-0.58 μM) established the hit cytotoxicity data. Compounds were plated in 384-well microplates in a stacked dose response format using the same doses used in the efficacy dose response. Bladder carcinoma 5637 cells were added to the compounds, and 72 hr later cell viability was measured using CellTiter Glo (38). Hit cytotoxicity and the 50% toxic concentration ($TC_{50}$) was determined and compared to the IC50 to calculate the therapeutic index. Test compounds are serially diluted in a plate to plate matrix or stacked plate matrix. All 320 compounds in a source plate are diluted together resulting in a 10 point dose response dilution series. It is visualized as a serial dilution series proceeding vertically through a stack of plates with the high dose plate on top and the low dose plate on the bottom.

Control Drug: Hyamine was used as a positive cytotoxic control. All wells contained 0.5% DMSO.

Preparation of Bladder carcinoma 5637 cells: Cells are harvested and resuspended to 80,000 cells per ml in Complete DMEM/F12®.

Endpoint Read: Following the three day incubation period, the assay plates were equilibrated to room temperature for 30 min and an equal volume (30 μL) of Cell Titer-Glo® reagent (Promega Inc.) is added to each well using a WellMate™ (Matrix, Hudson, N.H.) and plates are incubated for an additional 10 min at room temperature. At the end of the incubation, luminescence is measured using a Perkin Elmer Envision™ multi-label reader (PerkinElmer, Wellesley, Mass.) with an integration time of 0.1 s.

6.1.c Secondary Assay: Screening for Inhibitors of Bacterial Capsule Biogenesis E. coli Strain UT189

Purpose: This confirmatory cell-based assay provides an alternative measurement of inhibitory activity on phage-induced lysis. It measures reduction in bacterial capsule formation using an absorbance readout at $A_{600}$ instead of the alamar blue reagent.

Summary AID: 488970

Assigned AID: 504358, 504543, 504675, 504768, 588321, 588386, 588395

Assay Set-up: This secondary assay was conducted in the 96 well plate format. Bacterial cultures of E. coli K1 strain UTI89 (cystitis isolate) and isogenic capsule mutant strains (as controls for phage infection) were grown and prepared at the screening center immediately prior to use. Overnight starting cultures of UTI89 were grown at 37° C., and diluted 1:100 into LB. Compounds were added to plates in a concentration dependent manner in the range of 100-0.39 μM, followed by addition of 100 μL of bacterial culture. Each concentration was tested in quadruplicate. 1% DMSO (final well concentration) was included. The plates were tape sealed and shaken vigorously for 1.5 hr. An initial $OD_{600}$ reading at the time of infection was measured to identify compounds that cause growth retardation or bacterial killing in the absence of phage. Next, K1F phage (5 μL) was added to all of the test wells. The plates were resealed and shaken vigorously at 37° C., and measurements of $OD_{600}$ for phage-mediated lysis were taken after 3 hr.

Endpoint Read: The plates were read at ambient temperature from the bottom for absorbance at $A_{600}$ in an Envision plate reader (Perkin Elmer) and the degree of phage-mediated lysis was determined based on the absorbance.

6.1.d Secondary Assay: Screening for Inhibitors of Bacterial Capsule Biogenesis—T7 Lysis Inhibition Purpose: This secondary assay measures the compound mechanistic specificity for inhibition of bacterial capsule formation using a different bacterial phage (T7). In this assay, an increase in phage-induced lysis correlates to a decrease in capsule formation.

Summary AID: 488970 Assigned AID: 504349, 504538, 504676, 504767, 588322

Assay Description: T7 phage-mediated lysis assay: This assay determined if the mechanism of action of the compound is inhibition of phage infectivity or replication. The T7 phage has a nearly identical genome to K1F, without encoding an endosialidase. Its cycle of replication is similar to that of K1F as well. However, T7 entry into *E. coli* is inhibited by K capsules. This secondary assay was conducted in the 96 well plate format. Bacterial cultures of *E. coli* K1 strain UTI89 (cystitis isolate) and isogenic capsule mutant strains (as controls for phage infection) were grown and prepared immediately prior to use. Overnight starting cultures of UTI89 were grown at 37° C., and diluted 1:100 into LB. Compounds were added in quadruplicate to plates in a concentration dependent manner in the range of 100-0.39 μM, followed by addition of 100 μL of bacterial culture. 1% DMSO (final well concentration) was included. The plates were tape sealed and shaken vigorously for 1.5 hr. An initial $OD_{600}$ reading was measured to identify compounds that cause growth retardation or bacterial killing in the absence of phage. Next, T7 phage (5 μL) was added to all of the test wells. The plates were resealed and shaken vigorously at 37° C., and measurements of $OD_{600}$ for phage-mediated lysis were taken after 3 hr. True inhibitors of capsule yielded bacteria that were susceptible to T7 phage and lysed within 2 hr of the addition of phage. However, compounds inhibiting phage replication did not promote bacterial lysis. The positive control drug C7 (100 μM final well concentration) was used in this screen.

Endpoint Read: The plates were read at ambient temperature from the bottom for absorbance at $A_{600}$ in a BioTek Quantplate reader and the degree of phage-mediated lysis was determined based on the absorbance.

6.1.e Secondary Assay: Orcinol Secondary Screening for Inhibitors of Bacterial Capsule Biogenesis.

Purpose: This assay was performed only on the probe candidate. This is an end-point assay to measure the amount of K1 bacterial cell capsule formation in the presence of a test compound concentration range. The ability of the test compounds to inhibit the K1 capsule formation was measured by a reduction of absorbance from the complex formed by orcinol and the capsule polysaccharide. The biochemical determination of cell-surface associated capsule was performed using UTI89 or the delta Region I and Region II capsule mutant bacterial strains.

Summary AID: 488970

Assigned AID: 504733, 624060

Assay Description: The biochemical measurement of cell-surface associated capsule was performed. UTI89 or capsule mutants were grown in culture tubes with and without the test compound (50 μM). The cultures were centrifuged, and the cell pellets were washed in PBS and resuspended in Tris buffer, pH5. We have found that low pH releases surface polysaccharide without lysing the bacteria. Released polysaccharide was harvested by separation from whole bacteria by centrifugation followed by deproteination with phenol/chloroform and precipitation with ethanol. The precipitated material was subjected to acid hydrolysis (pH 2 at 80° C. for 1 hr) and incubated with orcinol, which reacts with periodic intermediates to produce a violet color quantified at OD 570 (3) Inhibitors reducing or abrogating surface encapsulation yielded low orcinol levels similar to the capsule export and synthesis mutants (Region I and II). The positive control drug C7 (100 μM final well concentration) was used in this screen.

Endpoint Read: The samples were read at ambient temperature from the bottom for absorbance at $A_{570}$ in a BioTek Quantplate reader and the degree of orcinol-reactive material was determined based on the absorbance compared to a wild-type encapsulated strain (UTI89) and a standard curve using purified sialic acid.

6.1.f Secondary Assay: K5 Secondary Screening for Inhibitors of Bacterial Capsule Biogenesis.

Purpose: This assay was performed only on the probe, and determined if compounds considered active in the T7 and orcinol secondary assays were able to inhibit also inhibit K5 capsule biogenesis.

Summary AID: 488970

Assigned AID: 624061

Assay Description: This assay was performed only on the probe candidate, and determined if compounds considered active in the T7 and orcinol secondary assays were able to also inhibit K5 capsule biogenesis. This assay was performed in a method identical to the T7 assay test, but a different bacterial test strain and bacteriophage are used. In this validation test, we used *E. coli* strain DS17, a pyelonephritis clinical isolate expressing a K5 capsule. DS17 is highly susceptible to K5 phage-mediated lysis. Thus, compounds that were active in the K1F phage assay but did not inhibit phage in the T7 phage assay were analyzed using this assay. This secondary assay was conducted in the 96 well plate format. Bacterial cultures of *E. coli* strain DS 17 were grown and prepared immediately prior to use. Overnight starting cultures of DS17 were grown at 37° C. and diluted 1:100 in LB. Compounds were added to plates in quadruplicate at 50 and 100 μM, followed by addition of 100 μL of bacterial culture. 1% DMSO (final well concentration) was included. The plates were tape sealed and shaken vigorously for 1.5 hr. An initial $OD_{600}$ reading was measured to identify compounds that cause growth retardation or bacterial killing in the absence of phage. Next, K5 bacteriophage (5 μL) was added to all of the test wells. The plates were resealed and shaken vigorously at 37° C., and measurements of $OD_{600}$ for phage-mediated lysis were taken after 3 hr. True inhibitors of capsule yielded bacteria that were not susceptible to K5 bacteriophage and did not show lysis within 2 hr of the addition of phage. The positive control drug C7 (100 μM final well concentration) was used in this screen.

Endpoint Read: The plates were read at ambient temperature from the bottom for absorbance at $A_{600}$ in a BioTek Quantplate reader and the degree of inhibition of phage-mediated lysis was determined based on the absorbance.

Analytical Characterization Data for the Five Supporting Analogues

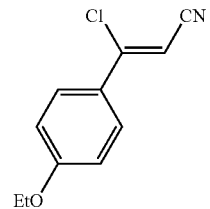 [SMILES: CCOc1ccc(/C(Cl)=C/C#N)cc1]

(Z)-3-Chloro-3-(4-ethoxyphenyl)acrylonitrile: $^1$H NMR (400 MHz, DMSO) δ 7.62 (d, J=9.2, 2H), 6.93 (d, J=9.2 Hz, 2H), 5.89 (s, 1H), 4.09 (q, J=7.2 Hz, 2H), 1.46 (t, J=6.8 Hz, 3H); ppm; $^{13}$C NMR (100 MHz, DMSO) δ 162.1, 152.9, 128.7, 126.3, 115.9, 114.7, 93.4, 63.9, 14.7 ppm; IR (ATR) 2983, 2217, 1593, 1506, 1238, 1039 cm$^{-1}$.

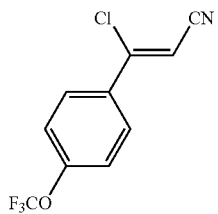 [SMILES: N#C/C=C(\Cl)c1ccc(OC(F)(F)F)cc1]

(Z)-3-Chloro-3-(4-(trifluoromethoxy)phenyl)acrylonitrile: $^1$H NMR (400 MHz, DMSO) δ 7.72 (d, J=9.2 Hz, 2H), 7.28 (dd, J=0.8, 8.0 Hz, 2H), 6.03 (s, 1H) ppm; $^{13}$C NMR (100 MHz, DMSO) δ ppm; IR (ATR) 2979, 2223, 1603, 1506, 1414, 1250, 1160 cm$^{-1}$.

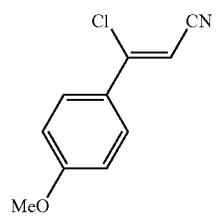

(Z)-3-Chloro-3-(4-methoxyphenyl)acrylonitrile: $^1$H NMR (400 MHz, DMSO) δ 7.67 (d, J=9.2 Hz, 2H), 6.97 (d, J=8.8 Hz, 2H), 5.93 (s, 1H), 3.89 (s, 3H) ppm; $^{13}$C NMR (100 MHz, DMSO) δ 164.1, 153.3, 145.9, 136.9, 130.6, 125.9, 125.9, 116.8, 81.2, 28.5 ppm; IR (ATR) 3051, 2562, 2211, 1594, 1504 cm$^{-1}$.

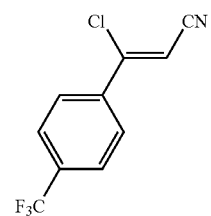 [SMILES: N#C/C=C(\Cl)c1ccc(C(F)(F)F)cc1]

(Z)-3-Chloro-3-(4-(trifluoromethyl)phenyl)acrylonitrile: $^1$H NMR (400 MHz, DMSO) δ 7.8 (d, J=8.0 Hz, 2H), 7.71 (d, J=8.4 Hz, 2H), 6.12 (s, 1H) ppm; $^{13}$C NMR (100 MHz, DMSO) δ 151.6, 137.5, 128.8, 127.4, 126.1, 125.3, 124.7, 114.8, 98.53 ppm; IR (ATR) 2978, 2224, 1604, 1410, 1322, 1169, 1118, 1068 cm$^{-1}$.

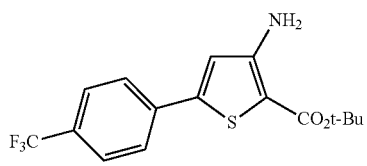 [SMILES: CC(C)(C)OC(=O)c1sc(-c2ccc(C(F)(F)F)cc2)cc1N]

tert-Butyl 3-amino-5-(4-(trifluoromethyl)phenyl)thiophene-2-carboxylate: $^1$H NMR (400 MHz, DMSO) δ 7.69 (d, J=8.4 Hz, 2H), 7.64 (d, J=8.4 Hz, 2H), 6.82 (s, 1H), 5.41 (s, 2H), 1.58 (s, 9H) ppm; $^{13}$C NMR (100 MHz, DMSO) δ 164.1, 153.3, 145.9, 136.9, 130.6, 130.3, 126.0, 125.9, 116.8, 81.2, 28.5 ppm; IR (ATR) 3350, 2981, 1659, 1604, 1320, 1169, 1107 cm$^{-1}$; HRMS calcd for $C_{16}H_{16}F_3NO_2S$ [M+H$^+$] 342.0853. found 342.0755.

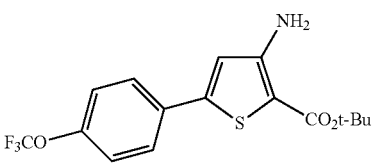 [SMILES: CC(C)(C)OC(=O)c1sc(-c2ccc(OC(F)(F)F)cc2)cc1N]

tert-Butyl 3-amino-5-(4-(trifluoromethoxy) phenyl)thiophene-2-carboxylate: $^1$H NMR (400 MHz, DMSO) δ 7.61 (d, J=8.8 Hz, 2H), 7.23 (d, J=8.8 Hz, 2H), 6.73 (s, 1H), 5.39 (s, 2H), 1.58 (s, 9H) ppm; $^{13}$C NMR (100 MHz, DMSO) δ 164.1, 153.4, 149.4, 146.3, 132.4, 127.3, 121.7, 119.1, 116.2, 81.0, 28.5, 27.9 ppm; IR (ATR) 3489, 3351, 2981, 1658, 1603, 1549, 1281, 1124 cm$^{-1}$; HRMS calcd for $C_{16}H_6F_3NO_3S$ [M+H$^+$] 359.0803. found 360.0884.

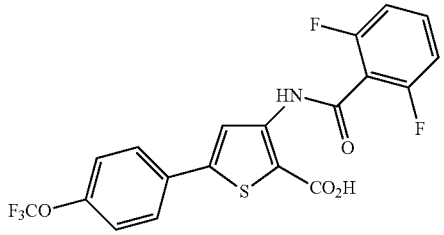 [SMILES: O=C(O)c1sc(-c2ccc(OC(F)(F)F)cc2)cc1NC(=O)c1c(F)cccc1F]

tert-Butyl 3-amino-5-(4-(trifluoromethoxy) phenyl)thiophene-2-carboxylate: $^1$H NMR (400 MHz, DMSO) δ 7.25 (d, J=8.8 Hz, 2H), 6.90 (d, J=8.8 Hz, 2H), 6.65 (s, 1H), 5.30 (s, 1H), 4.23 (t, J=8.0 Hz, 2H), 2.64 (m, 2H), 1.65 (s, 9H) ppm; $^{13}$C NMR (100 MHz, DMSO) δ 164.3, 158.6, 153.6, 147.9, 127.3, 127.2, 127.1, 124.5, 114.9, 114.8, 80.7, 61.1, 34.2, 28.5 ppm; IR (ATR) 3394, 2986, 1671, 1598, 1241, 1129, 1067, 827 cm$^{-1}$; HRMS calcd for $C_{18}H_{20}F_3NO_3S$ [M+H$^+$] 387.1116. found 387.1132.

3-(2,6-Difluoro benzamido)-5-(4-(trifluoro methoxy) phenyl)thiophene-2-carboxylic acid (CID-53495055, SID-126722926): $^1$H NMR (400 MHz, DMSO) δ 13.72 (s, 1H), 10.85 (s, 1H), 8.37 (s, 1H), 7.89 (d, J=7.2 Hz, 2H), 7.67 (m, 1H), 7.47 (d, J=6.4 Hz, 2H), 7.30 (t, J=6.8 Hz, 2H) ppm; $^{13}$C NMR (100 MHz, DMSO) δ 164.4, 160.2, 158.2, 157.1, 148.8, 146.1, 142.3, 133.5, 133.3, 131.5, 1127.9, 121.8, 118.9, 113.4, 112.6, 112.4 ppm; IR (ATR) 2908, 1668, 1572, 1259, 1212, 1168, 1004 cm$^{-1}$; HRMS calcd for $C_{19}H_{10}F_5NO_4S$ [M+H$^+$] 444.0323. found 444.0312.

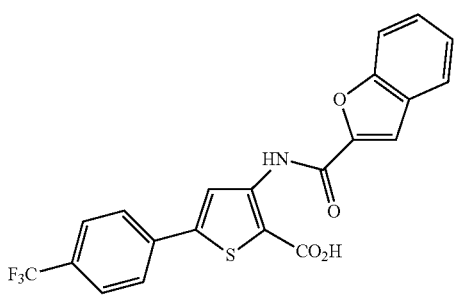 [SMILES: O=C(Nc1cc(-c2ccc(C(F)(F)F)cc2)sc1C(=O)O)c1cc2ccccc2o1]

3-(Benzofuran-2-carboxamido)-5-(4-(trifluoro methyl) phenyl)thiophene-2-carboxylic acid (CID-53470417, SID-126497335): $^1$H NMR (400 MHz, DMSO) δ 13.91 (s, 1H), 11.41 (s, 1H), 8.54 (s, 1H), 7.98 (d, J=6.4 Hz, 1H), 7.84-7.80 (m, 4H), 7.73 (d, J=6.8 Hz, 1H), 7.57 (t, J=6.4 Hz, 1H), 7.38 (t, J=6.0 Hz, 1H) ppm; $^{13}$C NMR (100 MHz, DMSO) δ 164.8, 155.0, 154.5, 147.5, 145.7, 142.9, 136.1, 129.3, 127.9, 127.2, 126.6, 124.2, 123.2, 119.1, 112.8, 111.9 ppm; IR (ATR) 1678, 1589, 1452, 1246, 1114 cm$^{-1}$; HRMS calcd for $C_{16}H_{16}F_3NO_3S$ [M+H$^+$] 430.0366. found 430.0375.

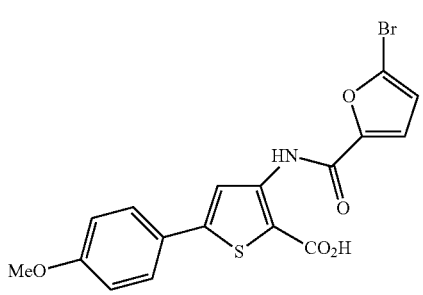 [SMILES: COc1ccc(-c2cc(NC(=O)c3ccc(Br)o3)c(C(=O)O)s2)cc1]

3-(5-Bromofuran-2-carboxamido)-5-(4-methoxy phenyl) thiophene-2-carboxylic acid (CID-53470446, SID-126497314): $^1$H NMR (400 MHz, DMSO) δ 13.63 (s, 1H), 11.13 (s, 1H), 8.21 (s, 1H), 7.66 (d, J=7.2 Hz, 2H), 7.35 (d, J=2.8 Hz, 1H), 7.03 (d, J=6.8 Hz, 2H), 6.91 (d, J=2.8 Hz, 1H), 3.80 (s, 3H) ppm; $^{13}$C NMR (100 MHz, DMSO) δ 16531, 160.3, 153.2, 148.4, 148.3, 143.3, 127.3, 126.1, 124.9, 118.5, 116.2, 115.2, 114.7, 109.7, 55.3 ppm; IR (ATR) 2941, 2834, 2562, 1674, 1648, 1591, 1017 cm$^{-1}$; HRMS calcd for $C_{17}H_{12}BrNO_5S$ [M+H$^+$] 421.9527. found 421.9534.

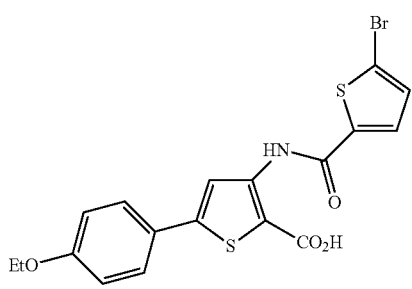 [SMILES: CCOc1ccc(-c2cc(NC(=O)c3ccc(Br)s3)c(C(=O)O)s2)cc1]

3-(5-Bromothiophene-2-carboxamido)-5-(4-ethoxy phenyl)thiophene-2-carboxylic acid (CID-53470415, SID-126497312): $^1$H NMR (400 MHz, DMSO) δ 13.64 (s, 1H), 11.07 (s, 1H), 8.13 (s, 1H), 7.65 (d, J=7.2 Hz, 2H), 7.56 (d, J=3.2 Hz, 1H), 7.42 (d, J=3.2 Hz, 1H), 7.01 (d, J=6.8 Hz, 2H), 4.09 (q, J=5.6 Hz, 2H), 1.35 (d, J=5.6 Hz, 3H) ppm; $^{13}$C NMR (100 MHz, DMSO) δ 165.2, 159.6, 157.1, 148.3, 143.4, 139.9, 132.2, 129.9, 127.2, 124.7, 118.9, 116.4, 115.1, 110.1, 63.3, 14.5 ppm; IR (ATR) 3351, 1648, 1590, 1415, 1259, 1184 cm$^{-1}$; HRMS calcd for $C_{18}H_{14}BrNO_4S_2$ [M+H$^+$] 451.9455. found 451.9472.

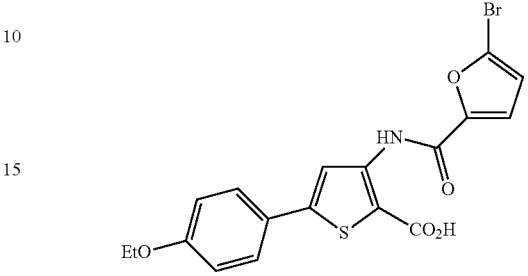

3-(5-Bromofuran-2-carboxamido)-5-(4-ethoxy phenyl)thiophene-2-carboxylic acid: $^1$H NMR (400 MHz, DMSO) δ 13.71 (s, 1H), 11.15 (s, 1H), 8.22 (s, 1H), 7.67 (d, J=6.8 Hz, 2H), 7.37 (d, J=2.8 Hz, 1H), 7.03 (s, J=7.2 Hz, 2H), 6.93 (d, J=2.8 Hz, 1H), 4.11 (q, J=5.6 Hz, 2H), 1.36 (t, J=5.6 Hz, 3H) ppm; $^{13}$C NMR (100 MHz, DMSO) δ 165.1, 159.6, 153.3, 148.4, 143.3, 127.3, 126.11, 124.8, 118.6, 116.2, 115.2, 109.7, 63.3, 14.5 ppm; IR (ATR) 3736, 2979, 2300, 1974, 1677, 1636, 1591, 1523, 1178 cm$^{-1}$; HRMS calcd for $C_{18}H_{14}BrNO_5S$ [M+H$^+$] 435.9684. found 435.9685.

Appendix 2: Ricerca LeadProfiling Report for ML317

Study Objective:

To evaluate, in radioligand binding assays, the activity of probe compound ML317 across a panel of 68 receptors.

Methods:

Methods employed in this study have been adapted from the scientific literature to maximize reliability and reproducibility. Reference standards were run as an integral part of each assay to ensure the validity of the results obtained.

Where presented, IC$_{50}$ values were determined by a non-linear, least squares regression analysis using MathIQ™ (ID Business Solutions Ltd., UK). Where inhibition constant (K$_i$) are presented, the Ki values were calculated using the equation of Cheng and Prusoff (Cheng. Y., Prusoff, W. H., Biochem. Pharmacol. 22:3099-3108, 1973) using the observed IC$_{50}$ of the tested compound, the concentration of radioligand employed in the assay, and the historical values of the KD of the ligand (obtained experimentally at Ricerca Biosciences, LC). Where presented, the Hill coefficient (n$_H$), defining the slope of the competitive binding curve, was calculated using MathIQ™. Hill coefficients significantly different than 1.0, may suggest that the binding displacement does not follow the laws of mass action with a single binding site. Where IC$_{50}$, and/or nH data are presented without Standard Error of the Mean (SEM), data are insufficient to be quantitative, and the values presented (Ki, IC50, n$_H$) should be interpreted with caution.

Detailed methods for any of the listed assays can be found by searching by catalog number for the assay (listed) at:

https ://pharmacology.ricerca.com/Catalog/AssayCatalog/AssayCatalog.aspx

| Cat # | Assay Name | Batch* | Spec. | Rep. | Conc. | % Inh. | IC$_5$ |
|---|---|---|---|---|---|---|---|
| | Compound: KUC107784N-02, PT #: 1160398 | | | | | | |
| 200510 | Adenosine A$_1$ | 314096 | hum | 2 | 10 μM | 28 | |
| 200610 | Adenosine A$_{2A}$ | 314151 | hum | 2 | 10 μM | 19 | |
| 200720 | Adenosine A$_3$ | 314213 | hum | 2 | 10 μM | 29 | |
| 203100 | Adrenergic α$_{1A}$ | 314153 | rat | 2 | 10 μM | 16 | |
| 203200 | Adrenergic α$_{1B}$ | 314154 | rat | 2 | 10 μM | 0 | |
| 203400 | Adrenergic α$_{1D}$ | 314156 | hum | 2 | 10 μM | 2 | |
| 203620 | Adrenergic α$_{2A}$ | 314100 | hum | 2 | 10 μM | −1 | |
| 204010 | Adrenergic β$_1$ | 314161 | hum | 2 | 10 μM | 2 | |
| 204110 | Adrenergic β$_2$ | 314163 | hum | 2 | 10 μM | 3 | |
| 285010 | Androgen (Testosterone) AR | 314097 | rat | 2 | 10 μM | −5 | |
| 212510 | Bradykinin B$_1$ | 314221 | hum | 2 | 10 μM | 3 | |
| 212620 | Bradykinin B$_2$ | 314223 | hum | 2 | 10 μM | 6 | |
| 214510 | Calcium Channel L-Type, Benzothiazepine | 314226 | rat | 2 | 10 μM | 2 | |
| 214600 | Calcium Channel L-Type, Dihydropyridine | 314169 | rat | 2 | 10 μM | 32 | |
| 216000 | Calcium Channel N-Type | 314227 | rat | 2 | 10 μM | −16 | |
| 217030 | Cannabinoid CB$_1$ | 314171 | hum | 2 | 10 μM | 13 | |
| 219500 | Dopamine D$_1$ | 314173 | hum | 2 | 10 μM | 5 | |
| 219700 | Dopamine D$_{2S}$ | 314174 | hum | 2 | 10 μM | 4 | |
| 219800 | Dopamine D$_3$ | 314297 | hum | 2 | 10 μM | 4 | |
| 219900 | Dopamine D$_{42}$ | 314238 | hum | 2 | 10 μM | 7 | |
| 224010 | Endothelin ET$_A$ | 314240 | hum | 2 | 10 μM | 8 | |
| 224110 | Endothelin ET$_B$ | 314241 | hum | 2 | 10 μM | 3 | |
| 225510 | Epidermal Growth Factor (EGF) | 314243 | hum | 2 | 10 μM | 6 | |
| 226010 | Estrogen ERα | 314245 | hum | 2 | 10 μM | 9 | |
| 226600 | GABA$_A$, Flunitrazepam, Central | 314115 | rat | 2 | 10 μM | 16 | |
| 226500 | GABA$_A$, Muscimol, Central | 314175 | rat | 2 | 10 μM | 9 | |
| 228610 | GABA$_{B1A}$ | 314248 | hum | 2 | 10 μM | 5 | |
| 232030 | Glucocorticoid | 314321 | hum | 2 | 10 μM | −2 | |
| 232700 | Glutamate, Kainate | 314298 | rat | 2 | 10 μM | 11 | |
| 232810 | Glutamate, NMDA, Agonism | 314250 | rat | 2 | 10 μM | 9 | |
| 232910 | Glutamate, NMDA, Glycine | 314253 | rat | 2 | 10 μM | −1 | |
| 233000 | Glutamate, NMDA, Phencyclidine | 314178 | rat | 2 | 10 μM | 6 | |
| 239610 | Histamine H$_1$ | 314180 | hum | 2 | 10 μM | 2 | |

| Cat # | Assay Name | Batch* | Spec. | Rep. | Conc. | % Inh. |
|---|---|---|---|---|---|---|
| 239710 | Histamine H$_2$ | 314258 | hum | 2 | 10 μM | 2 |
| 239820 | Histamine H$_3$ | 314302 | hum | 2 | 10 μM | 14 |
| 241000 | Imidazoline I$_2$, Central | 314181 | rat | 2 | 10 μM | −1 |
| 243520 | Interleukin IL-1 | 314186 | mouse | 2 | 10 μM | 3 |
| 250460 | Leukotriene, Cysteinyl CysLT$_1$ | 314262 | hum | 2 | 10 μM | 0 |
| 251600 | Melatonin MT$_1$ | 314266 | hum | 2 | 10 μM | 3 |
| 252610 | Muscarinic M$_1$ | 314320 | hum | 2 | 10 μM | 1 |
| 252710 | Muscarinic M$_2$ | 314183 | hum | 2 | 10 μM | −8 |
| 252810 | Muscarinic M$_3$ | 314185 | hum | 2 | 10 μM | 14 |
| 257010 | Neuropeptide Y Y$_1$ | 314271 | hum | 2 | 10 μM | 5 |
| 257110 | Neuropeptide Y Y$_2$ | 314303 | hum | 2 | 10 μM | −3 |
| 258590 | Nicotinic Acetylcholine | 314188 | hum | 2 | 10 μM | 13 |
| 258700 | Nicotinic Acetylcholine α1, Bungarotoxin | 314189 | hum | 2 | 10 μM | 8 |
| 260130 | Opiate δ$_1$, (OP1, DOP) | 314191 | hum | 2 | 10 μM | 0 |
| 260210 | Opiate κ(OP2, KOP) | 314304 | hum | 2 | 10 μM | 14 |
| 260410 | Opiate μ(OP3, MOP) | 314194 | hum | 2 | 10 μM | 3 |
| 264500 | Phorbol Ester | 314195 | mouse | 2 | 10 μM | −1 |
| 265010 | Platelet Activating Factor (PAF) | 314197 | hum | 2 | 10 μM | 4 |
| 265600 | Potassium Channel [K$_{ATP}$] | 314201 | ham | 2 | 10 μM | 9 |
| 265900 | Potassium Channel hERG | 314202 | hum | 2 | 10 μM | −11 |
| 268420 | Prostanoid EP$_4$ | 314208 | hum | 2 | 10 μM | −4 |
| 268700 | Purinergic P$_{2X}$ | 314300 | rabbit | 2 | 10 μM | −2 |
| 268810 | Purinergic P$_{2Y}$ | 314301 | rat | 2 | 10 μM | 8 |
| 270000 | Rolipram | 314203 | rat | 2 | 10 μM | 9 |
| 271110 | Serotonin (5-Hydroxytryptamine) 5-HT$_{1A}$ | 314275 | hum | 2 | 10 μM | 4 |
| 271700 | Serotonin (5-Hydroxytryptamine) 5-HT$_{2B}$ | 314205 | hum | 2 | 10 μM | 11 |
| 271910 | Serotonin (5-Hydroxytryptamine) 5-HT$_3$ | 314281 | hum | 2 | 10 μM | −11 |
| 278110 | Sigma σ$_1$ | 314095 | hum | 2 | 10 μM | 5 |
| 255520 | Tachykinin NK$_1$ | 314269 | hum | 2 | 10 μM | 7 |
| 285900 | Thyroid Hormone | 314309 | rat | 2 | 10 μM | −3 |
| 220320 | Transporter, Dopamine (DAT) | 314094 | hum | 2 | 10 μM | 8 |
| 226400 | Transporter, GABA | 314450 | rat | 2 | 10 μM | 10 |
| 204410 | Transporter, Norepinephrine (NET) | 314086 | hum | 2 | 10 μM | 13 |
| 274030 | Transporter, Serotonin (5-Hydroxytryptamine) (SERT) | 314284 | hum | 2 | 10 μM | 8 |

Note:
Items meeting criteria for significance (≥50% stimulation or inhibition) are highlighted.
*Batch: Represents compounds tested concurrently in the same assay(s).
R = See Remarks (if any) at end of this section.
ham = Hamster; hum = Human

7. EXAMPLES SECTION 3

Methods

Bacterial strains, phage, and growth conditions. All *E. coli* strains and phage used in the present study are listed in Table 1. Unless otherwise indicated, bacteria were routinely grown at 37° C. in Luria-Bertani medium (LB) with shaking at 250 rpm. LB was supplemented with 1% dimethyl sulfoxide (DMSO; Acros) with or without compound. Phage lysates were prepared from 50 mL cultures of *E. coli* strains UTI89 (for K1F phage), MG1655 (for T7 phage) or DS17 (for K5 phage) and stored at 4° C. over several drops of chloroform as described [37].

Screen for Inhibitors of Bacterial Capsule Biogenesis.

Primary assay. The primary assay consisted of detection of the presence and absence of the K1 capsule on the *E. coli* urinary tract isolate UTI89 under growth conditions with compounds from a large chemical library. The assay was conducted as previously described [36] with the following modifications. The primary assay was conducted in 1,536-well plate format. UTI89 ΔkpsM, an isogenic K1 capsule export mutant, was included as an unencapsulated control. Tetracycline, 50 µM, was used as a negative growth control. A 1:75 dilution of overnight cultures were made in LB broth containing 0.5% DMSO, and 3 µL of this culture was added to each plate well, and plates were incubated, inverted, at 37° C. for 2 hr. K1F phage stock was diluted 1:8 in LB Broth containing 0.5% DMSO, and 1.5 µL of diluted phage (or media only) was added to the pre-plated test compound wells and appropriate control wells. The plates were centrifuged briefly, and then were incubated, inverted, at 37° C. for an additional 2 hr. To increase sensitivity of detection of viable bacteria, 1 µL of a 1:2 dilution of AlamarBlue reagent (Invitrogen, #DAL1100) in LB broth was added to each plate well. Alamar Blue, resazurin, is converted in living cells to the fluorescent molecule, resorufin. The plates were again centrifuged briefly, and then were further incubated, inverted, at 37° C. for 30 min Resorufin fluorescence was measured using excitation of 560 nm and emission of 590 nm, as per the manufacturer's recommendations.

Compounds from the NIH Molecular Libraries Small Molecule Repository (MLSMR) were utilized in the primary assay. The MLSMR collection of over 300,000 compounds generically grouped into one of the following five categories: (a) specialty sets, comprising bioactive compounds such as known drugs and toxins, (b) non-commercial compounds, mainly from academic labs, (c) targeted libraries, (d) natural products, and (e) diversity compounds [38]. The MLSMR library covers a diverse sample of the chemical space occupied by drugs and natural products, but only narrowly represents combinatorial chemical space [39]. Compounds or vehicle control (DMSO) were diluted to a final well concentration of 1:200 in assay media. Compounds (22.5 nL in 100% DMSO) were dispensed to assay plates using an Echo non-contact dispenser (Labcyte). Compounds from the libraries were added to the plates at a final concentration of 50 µM, before the addition of bacteria or phage. Each compound was tested as a single point, and ~1,200 compounds were tested per plate. A positive hit was defined by the compound producing greater than a 50% inhibition of K1F phage-induced lysis. Compound hits were further confirmed using an optical density-based detection method in a 96-well format as previously described [36].

Concentration-response to chemical inhibition. Concentration-response testing (concentration range=0.58-300 µM) was used to confirm and characterize the primary screen hits, which was necessary to determine the number of compounds advanced to secondary screens. Compounds were plated in 1536-well microplates, and the concentration-response efficacy assay was performed as described for the primary screen, with the exception that each compound was tested in duplicate at 10 concentration points starting from 300 µM and continuing to lower concentrations by 2-fold serial dilutions. The strain UTI89 ΔkpsM, a K1 capsule export mutant, was evaluated with the wild-type strain as a phage-insensitive control (mimicking 100% capsule inhibition).

T7 phage counter assay. This secondary assay was performed as previously described [36] and was used to distinguish compounds with phage inhibitory effects from true polysaccharide capsule inhibitors. T7 phage has a nearly identical genome to K1F phage and thus a similar life cycle [40]; however, T7 phage does not encode for an endosialidase, and its entry into *E. coli* is inhibited by K capsules. Thus, the presence of a capsule inhibits T7-mediated lysis [41]. In this assay, an increase in phage-induced lysis correlates to a decrease in capsule formation. True inhibitors of capsule yielded bacteria that were susceptible to T7 phage and lysed within 2 hr of the addition of phage. However, compounds inhibiting phage replication did not promote bacterial lysis. The positive control molecule C7 (100 µM final well concentration) was used in this screen.

Pan Assay Interference Compound (PAINS) analysis. Groups of compound substructural features are associated with compound biological promiscuity, and compounds containing these features arise as frequent hits in biochemical high throughput screens. These molecules have been described as PAINS [42]. To determine if molecules of interest were within chemical groups with known non-specific interference with the bioassays, the structures for compounds DU001, DU003, DU005, DU007, DU008, and DU011 were retrieved from PubChem and saved in the Structure Data Format (SDF). The structures were then compared to the SYBYL PAINS compounds library, to see which, if any, of the compounds contain PAINS functional groups [43].

Cytotoxicity. Testing was performed essentially as previously described [36,44]. Concentration-response testing was performed over a range 0.58-300 µM in a 386 well plate format. Bladder carcinoma 5637 cells (ATCC HTB-9) were added to the compounds, and 72 hrs later cell viability was measured using CellTiter Glo (Promega). The 50% toxic concentration ($TC_{50}$) was determined and compared to the $IC_{50}$ to calculate the therapeutic index. Hyamine was used as a positive cytotoxic control. All wells contained 0.5% DMSO.

Evaluation of off-target effects. Off target effects of lead molecules of interest were evaluated using the LeadProfilingScreen commercial assay at Eurofins Panlabs (Bothell, Wash.). Reference standards were run as an integral part of each assay to ensure the validity of the results obtained. Assay results are presented as the percent inhibition of specific binding or activity (for n=2 replicates) for the probe compound tested at a concentration of 10 µM. Details regarding the individual assays and methods are provided in Supplementary Information File 51.

Orcinol assay for released capsule material. Orcinol reactivity was used as a biochemical confirmation of altered extracellular capsule after compound treatment. UTI89 or an isogenic capsule mutant was grown in 100 µM of test compound or 1% DMSO. The assay was performed as previously described [36]. The molecule C7 (100 µM final concentration) was used as a positive control. The assay was performed 3 times with replicate samples.

K1 antigen dot blot. K1 antigen was detected by dot blot assays of culture extracts probed with anti-K1 H46 serum. The assay was performed as previously described [36]. The experiment was repeated twice with similar results, and a representative dot blot is shown.

Visualization of capsule using Alcian blue staining. Overnight cultures of clinical *E. coli* strains were diluted 1:100 in the presence of 1% DMSO or 100 µM DU011. Cultures were grown for ~6 hrs ($OD_{600}$=1.2) at 37° C. Samples were centrifuged at 13,200 RPM for 5 min. The medium was removed and the cells were resuspended in 500 µL of Tris-Acetate (pH 5) and shaken for 1 hr at 37° C. Samples were re-centrifuged, and the supernatant was concentrated ~100 fold in Amicon 3K microconcentrators. The preparations were separated on a 7.5% SDS-PAGE gel and stained with 0.125% Alcian blue as previously described [45].

K5 phage assay. This assay determined if compounds found to be active in the K1F, T7, orcinol, and K1 antigen dot blot secondary assays were able to also inhibit K5 capsule biogenesis. The assay was performed in a method identical to the T7 assay test [36]. *E. coli* strain DS17, a pyelonephritis clinical isolate expressing a K5 capsule and susceptible to K5 phage (K5), was used as a K5 prototypic test strain. The degree of inhibition of phage-mediated lysis was determined based on the absorbance ($OD_{600}$).

Human serum sensitization by capsule inhibitor treatment. Overnight cultures of UTI89 were diluted 1:100 and grown with or without 50 µM compound for approximately 1.5 hrs on a shaker at 37° C. Then 25 µL of anonymous, non-identified, sterile filtered pooled human serum (purchased from Equitech Bio) was added per 100 µL of growth media. This was returned to the shaker for another 3 hrs, after which 20 µL of 5 mg/mL MTT (3-(4,5-Dimethylthiazol-2-yl)-2,5-diphenyltetrazolium bromide) was added. MTT is reduced to purple formazan by bacterial reductase enzymes, thus measuring viable bacteria. This was shaken for another 15 min at 37° C. The sample was spun to remove the growth media, followed by two washes with PBS. The formazan crystals were dissolved in 100 µL of DMSO and measured at $OD_{570}$.

Murine UPEC sepsis model and treatment with DU011. Groups of five 6-7 week old C57BL/6NCr female mice (purchased from Frederick National Laboratory for Cancer Research) were injected subcutaneously twice daily with 100 µL of 1% DMSO (vehicle control) or DU011 (1 mg/ml) starting 12 hrs prior to the intra peritoneal infection. Weights were recorded twice daily to monitor health of the animals and tolerance to the compound. Mice were challenged by intraperitoneal injection with $10^8$ CFU of the indicated *E. coli* UTI89 in 100 µL of PBS. Briefly, cultures were prepared by diluting overnight cultures (18 hrs) 1:100 into 3 mL of LB supplemented with 1% DMSO final or 100 µM DU011 (1% DMSO final). Shaken cultures were grown at 37° C. for 6 hours to an $OD_{600}$ of 1.2, and then cells were pelleted and resuspended in 1 mL of PBS. Absorbance was adjusted to $OD_{600}$ of 0.8 in PBS, and the cultures were then diluted 1:10 in sterile PBS Animals were also given an intraperitoneal dose of 1% DMSO or DU011, in a site different than the administration of bacteria, to ensure sufficient systemic delivery of drug. Animal survival was assessed after 12 hours. Surviving mice were re-dosed according to the treatment groups and continued to be monitored. The experiment was concluded 48 hours post infection. The entire experiment was repeated with similar results.

Throughout each experiment, animals were monitored each 6 hours from the time of infection until conclusion for serious morbidity, including ruffled fur, decreased activity, slowed respirations, and ill appearance. Animals were provided gel packs for easily accessible additional hydration throughout the experiments. When a moribund state was suspected or anticipated by these criteria, animals were immediately euthanized to minimize potential pain and/or suffering. Of the total animals with an outcome categorized as death, the following numbers were euthanized for terminal morbidity prior to septic death (euthanized/total deaths): 3/10, no prior treatment; 3/5 prior chemical treatment of bacteria alone; 0/2 prior chemical treatment of mice alone. Euthanasia for all animals was through complete respiratory cessation using the inhaled anesthetic isoflurane followed by secondary assurance of death using bilateral thoracotomy. All animal experiments were conducted with prior approval from the Institutional Animal Care and Use Committee of Duke University.

Statistical analyses. Results were calculated as averages and standard deviations of the means using the Graph Pad Prism 5 software package (San Diego, Calif.). Nonparametric t-tests were used for statistical analysis of data and calculation of p-values using Graph Pad Prism 5 or Graph Pad online calculators. Significant differences are highlighted with a single asterisk when the p value is less than 0.05, with two asterisks when the p value is less than 0.01, and three asterisks when the p value is less than 0.001.

Results

Primary screen for novel capsule inhibitors. Our initial screen of 2,195 compounds from the Developmental Therapeutics Program at the National Cancer Institute successfully identified a small-molecule inhibitor of uropathogenic *E. coli* Group 2 capsule biogenesis. We described this compound, termed C7, in a previous report as proof-of-principle that small-molecule inhibition of capsule biogenesis is possible and that these novel anti-infectives can block encapsulation and attenuate a pathogen through exposure to host innate immune factors [36]. Based on this proof-of-concept, the primary assay was adapted to a 1,536-well format with the modifications for high-throughput screening necessary to search for additional active molecules in significantly larger chemical repositories. The K1 encapsulated strain of uropathogenic *E. coli* UTI89 was grown in a 1,536-well plate format in the presence of 50 µM compounds. After an initial growth step, K1F phage specific for K1 capsule was added. Compounds with no effect on capsule biogenesis allowed the growth of organisms with an intact capsule that were subsequently lysed by the addition of the K1F phage. However, those compounds that presumably inhibited capsule biogenesis and allowed growth of the unencapsulated organism did not lyse with the addition of the K1F phage. These compounds were then selected for a secondary assay.

In total, 338,740 compounds were screened in the primary assay (using K1F phage), and 1,767 compounds associated with resistance to phage lysis (0.52% of total) were tested in concentration-response format. Of these, 29 compounds passed concentration-response validation (1.6% of compounds passing the primary screen), and 6 were selected after demonstrating high activity in the T7 phage secondary assay, the reciprocal phage assay in which chemical unencapsulation sensitizes a K1:K12 hybrid strain, EV36, to lysis by the T7 phage. Concentration response curves for 2 of these compounds are shown in FIG. 12. Compounds with promising chemical structures and low cytotoxicity to cultured bladder epithelial cells were selected for further characterization. As seen in Table 2, the activity of these compound hits in primary and secondary assays is consistent with molecules with capsule inhibitory action. Cytotoxicity data further indicate that these molecules are non-toxic to cultured bladder epithelial cells. Furthermore, these new compounds, designated DU001, DU003, DU005, DU007, DU008, and DU011, are more active in the phage assays than the original proof-of-concept agent C7, with $IC_{50}$ values in the micromolar range.

Identification of potential Pan Assay Interference Compounds (PAINS) among capsule inhibitor hits. A number of compound substructural features have been identified that are associated with compound biological promiscuity, and, in particular, compounds with certain structural features appear as frequent hits in biochemical high throughput screens. These molecules have been described as PAINS. Although PAINS may remain useful hits, we sought to prioritize the compound hits DU001, DU003, DU005, DU007, DU008, and DU011 by identifying and removing PAINS-like molecules from our prioritization. Three of the six most active and selective compound hits, DU005, DU007, and DU008, are considered PAINS [40], and thus were not submitted for additional biological characterization.

Confirmation of primary hits and spectrum of activity. Compounds were further characterized by determining biochemically the level of surface capsule upon compound treatment of a wild-type K1 encapsulated UPEC strain. We used mild-acid to release capsule from cultures of UTI89 grown in the presence of 100 μM compound. We then used the orcinol reagent to quantify the amount of released material. As shown in FIG. 12 panel A, orcinol reactivity as % of wild-type for compound treatment indicates that cultures treated with capsule inhibitors had decreased surface reactive material, similar to levels observed for capsule synthesis and assembly mutants.

As another independent measure of capsule inhibition by the DU compounds, K1 antigen was evaluated using whole-cell dot blots with anti-K1 serum. In all cases, treatment with these molecules reduced reactivity to levels resembling those of genetic capsule mutants (FIG. 12 panel B). The combined results from the phage, orcinol, and immune-dot blots demonstrate that these molecules inhibit normal capsule production and assembly, significantly reducing the amount of surface assembled capsule.

A major consideration was whether the inhibitors of K1 encapsulation were also able to inhibit the production of other important E. coli Group 2 capsule types. To confirm the range of activity, we first demonstrated that treatment with each of confirmed inhibitory molecules also inhibited K5 phage infection of a K5 capsule-expressing strain, DS 17 (FIG. 13 panel A). We next determined if leading capsule inhibitors would also inhibit the production of capsule in non-K1 serotypes. Capsular material was isolated from strains 536 (K15 serotype), CFT073 (K2 serotype) and DS17 (K5 serotype), and UTI89 (K1 serotype) in the presence and absence of capsule inhibitors. Capsule was isolated from the same amount of bacteria after growth in vehicle or with inhibitor DU011 (200 μM). Isolated material was separated on a polyacrylamide gel and stained with the cationic dye alcian blue. As shown in FIG. 13 panel B, capsule was reduced in each strain following growth with DU011, regardless of serotype. Although visibly reduced in capsule after growth in DU011, the reduction in capsular material from treated CFT073 appeared slightly less than the other serotypes tested. A similar reduction in extracted capsule was also seen with DU003 (data not shown).

Chemical inhibition sensitized UPEC to serum-mediated killing. Capsule offers protection against serum-mediated killing. In order to test whether compound treatment of UPEC increased serum-mediated killing, an in vitro serum resistance assay was used. As shown in FIG. 14, pooled human serum decreased the amount of viable UPEC as measured by an MTT metabolic activity assay. Treatment of UPEC with either 50 μM DU003 or DU011 further increased serum-mediated killing, thus significantly reducing the measurable bacteria as compared to DMSO treated cells (p=0.0067). This decrease was similar to the serum sensitivity observed for a genetic capsule mutant (Δneu).

DU003 & DU011 are biologically selective. DU003 and DU011 were submitted to the Eurofins Panlabs LeadProfilingScreen to assess off-target pharmacology 1421. Both compounds were tested in duplicate at 10 μM concentration and showed no significant activity across the panel of 68 targets (i.e., <32% inhibition for DU011 and <30% inhibition for DU003, except for one target, the norepinephrine transporter, for which 58% inhibition was observed; full data and assays are provided in Supplementary Information File S1). In review of PubChem data, DU011 (CID23602075) is reported to have shown activity in only 21 of 467 (4.5%, as of Sep. 5, 2013) bioassays in which it was tested (assays unrelated to the current project). Per PubChem, DU003 (CID18109210) is reported to have shown activity in only 5 of 427 (1.2%, as of Sep. 5, 2013) bioassays in which it was tested (assays unrelated to the current project). Together, these results suggest that DU011 and DU003 are not biologically promiscuous compounds.

Attenuation of E. coli disseminated infection by DU011. In order to test the ability of these compounds to prevent lethal systemic E. coli infection in mice, we selected DU011 for animal testing based on its favorable solubility, permeability, and plasma and microsome stability profiles (Table 3). As shown in FIG. 15 panel A, C57BL/6 mice were administered DU011 or 1% DMSO 12 hours prior to lethal challenge with $10^8$ CFU of UPEC UTI89 by intraperitoneal injection. All previously untreated mice receiving non-pretreated bacteria were moribund or died within 24 hr post-infection. In contrast, pretreatment of the bacteria and mice with DU011 conferred complete protection with 100% survival for the duration of the experiments (48 hrs) and recovery of pre-infection weights (FIG. 15 panel B), similar to the 100% survival of animals administered UTI89 ΔRII, an unencapsulated isogenic mutant (data not shown). Administration of subcutaneous DU011 and untreated UTI89 provided 80% survival with stabilization of weights at the end of the experiment. Pre-treatment of bacteria without pretreatment of the mice produced 50% survival with ongoing weight loss among surviving animals. Mice tolerated DU011 without evident side effects. These data indicate that pretreatment of mice with DU011 was able to significantly reduce mortality due to disseminated E. coli infection, demonstrating the potency of polysaccharide inhibition in vivo.

Discussion

E. coli infections play a significant role in community-acquired UTI with substantial morbidity and associated costs. With a diminishing arsenal of antibiotics available for the treatment of UTI, new therapeutics are in great demand. Anti-virulence agents capable of specifically attenuating a pathogenic organism during its infectious cycle hold great potential as they may spare the microbiota in commensal niches.

Previous work in our lab and in others has highlighted the importance of capsular polysaccharides in the pathogenesis of uropathogenic E. coli [27-29]. Group 2 and 3 capsules are highly conserved and represent the predominant circulating capsule types [46]. We have previously described the identification and characterization of a novel agent designated C7 that is active ($IC_{50}$ between 12.5-25 μM), blocks the production of K1 and K5 capsule biogenesis, and lacks obvious toxicity to cultured bladder epithelial cells [36]. We have since conducted a high-throughput screen for additional broad-spectrum capsule inhibitors, finding several structurally distinct and highly active new molecules with promising therapeutic characteristics.

Herein, we described the initial identification and characterization of these new small molecules. This group of capsule inhibitors features lower $IC_{50}$ values and improved solubility, permeability, and plasma and microsome stability profiles. We have demonstrated their activity in assays with human serum (FIG. 14). Most importantly, dosing of mice with DU011 had no detectable adverse effects on the animals and protected against a lethal *E. coli* systemic challenge (FIG. 15). In vivo results are shown in Figure This new approach may provide the basis for the next pre-clinical steps to test these inhibitors as UTI-specific therapeutics that render microbes vulnerable to host clearance mechanisms such as innate immunity, enhancing the adaptive immune responses in the process by allowing greater engagement of the immune system. While dosing and delivery will need to be evaluated in future pre-clinical pharmacokinetic and pharmacodynamics studies, we believe these data highlight the potential use of capsule inhibitors as specific anti-virulence therapeutics. The compounds listed in Tables 2 and 3 are synthetically amenable lead compounds and work is currently underway to improve upon their properties. Synthesis of large lots of DU011 and other compound hits has made animal testing possible as well as facilitated work on the mechanism of action of these compounds. This will aid in the identification of their biological target and will advance our understanding of capsule biogenesis and regulation in *E. coli* and other organisms with similarly conserved capsule loci. This could lead to the attenuation of diverse encapsulated organisms sharing similar capsule assembly and regulatory mechanisms. The generation of novel highly active small-molecule inhibitors of capsule biogenesis will also aid in our understanding of the role of the innate and adaptive immune systems in control of encapsulated bacterial pathogens during systemic infections. A better understanding of how DU003, DU011 and others affect the interaction of the bacterium with host immune responses will significantly aid in the development better anti-infectives that not only attenuate the organism, but also actively engage the host immune system to promote clearance.

8. REFERENCES EXAMPLE 3

1. NKUDIC (2005) Urinary Tract Infections in Adults.
2. Schappert S, Rechtsteiner E (2011) Ambulatory medical care utilization estimates for 2007. Vital and health statistics. Series 13.
3. Foxman B (2010) The epidemiology of urinary tract infection. Nat Rev Urol 7: 653-660. doi:10.1038/nrurol.2010.190.
4. Gupta K, Scholes D, Stamm W E (1999) Increasing prevalence of antimicrobial resistance among uropathogens causing acute uncomplicated cystitis in women. Jama 281: 736-738. doi:jbr80382 [pii].
5. Ma J F, Shortliffe L M D (2004) Urinary tract infection in children: etiology and epidemiology. Urol Clin North Am 31: 517-26, ix-x. doi:10.1016/j.ucl.2004.04.016.
6. Hooton T M, Scholes D, Stapleton A E, Roberts P L, Winter C, et al. (2000) A prospective study of asymptomatic bacteriuria in sexually active young women. N Engl J Med 343: 992-997. doi:10.1056/NEJM200010053431402.
7. Foxman B, Brown P (2003) Epidemiology of urinary tract infections: transmission and risk factors, incidence, and costs. Infect Dis Clin North Am 17: 227-241.
8. Gaschignard J, Levy C, Romain O, Cohen R, Bingen E, et al. (2011) Neonatal Bacterial Meningitis: 444 Cases in 7 Years. Pediatr Infect Dis J 30: 212-217.
9. Litwin M, Saigal C (2007) Introduction. In: Litwin M, Saigal C, editors. Urologic Diseases in America. Washington, D.C: NIH. pp. 3-7.
10. King T, Abedin A, Belal M (2012) Rise of multi-resistant urinary tract infections. BJU Int 110: 300-301. doi:10.1111/j.1464-410X.2012.11142.x.
11. Olson R P, Harrell L J, Kaye K S (2009) Antibiotic resistance in urinary isolates of *Escherichia coli* from college women with urinary tract infections. Antimicrob Agents Chemother 53: 1285-1286.
12. Edlin R S, Shapiro D J, Hersh A L, Copp H L (2013) Antibiotic resistance patterns of outpatient pediatric urinary tract infections. J Urol 190: 222-227. doi:10.1016/j.juro.2013.01.069.
13. Gupta K, Hooton T M, Naber K G, Wullt B, Colgan R, et al. (2011) International clinical practice guidelines for the treatment of acute uncomplicated cystitis and pyelonephritis in women: A 2010 update by the Infectious Diseases Society of America and the European Society for Microbiology and Infectious Diseases. Clin Infect Dis 52: e103-20. doi:ciq257 [pii] 10.1093/cid/ciq257.
14. Yang Q, Zhang H, Wang Y, Xu Y, Chen M, et al. (2013) A 10 year surveillance for antimicrobial susceptibility of *Escherichia coli* and *Klebsiella pneumoniae* in community- and hospital-associated intra-abdominal infections in China. J Med Microbiol 62: 1343-1349. doi:10.1099/jmm.0.059816-0.
15. Gupta K, Hooton T M, Stamm W E (2005) Isolation of fluoroquinolone-resistant rectal *Escherichia coli* after treatment of acute uncomplicated cystitis. J Antimicrob Chemother 56: 243-246.
16. Karlowsky J A, Hoban D J, Decorby M R, Laing N M, Zhanel G G (2006) Fluoroquinolone-resistant urinary isolates of *Escherichia coli* from outpatients are frequently multidrug resistant: results from the North American Urinary Tract Infection Collaborative Alliance-Quinolone Resistance study. Antimicrob Agents Chemother 50: 2251-2254.
17. Hang L, Wullt B, Shen Z, Karpman D, Svanborg C (1998) Cytokine repertoire of epithelial cells lining the human urinary tract. J Urol 159: 2185-2192.
18. Schilling J D, Mulvey M A, Vincent C D, Lorenz R G, Hultgren S J (2001) Bacterial invasion augments epithelial cytokine responses to *Escherichia coli* through a lipopolysaccharide-dependent mechanism. J Immunol 166: 1148-1155.
19. Hedges S, Anderson P, Lidin-Janson G, de Man P, Svanborg C (1991) Interleukin-6 response to deliberate colonization of the human urinary tract with gram-negative bacteria. Infect Immun 59: 421-427.
20. Svanborg C, Agace W, Hedges S, Linder H, Svensson M (1993) Bacterial adherence and epithelial cell cytokine production. Zentralbl Bakteriol 278: 359-364.
21. Schilling J D, Martin S M, Hung C S, Lorenz R G, Hultgren S J (2003) Toll-like receptor 4 on stromal and hematopoietic cells mediates innate resistance to uropathogenic *Escherichia coli*. Proc Natl Acad Sci USA 100: 4203-4208.

22. Li K, Sacks S H, Sheerin N S (2008) The classical complement pathway plays a critical role in the opsonisation of uropathogenic *Escherichia coli*. Mol Immunol 45: 954-962.
23. Valore E V, Park C H, Quayle A J, Wiles K R, McCray Jr. P B, et al. (1998) Human beta-defensin-1: an antimicrobial peptide of urogenital tissues. J Clin Invest 101: 1633-1642.
24. Ali A S M, Townes C L, Hall J, Pickard R S (2009) Maintaining a sterile urinary tract: the role of antimicrobial peptides. J Urol 182: 21-28. doi:10.1016/j.juro.2009.02.124.
25. Roberts I S (1995) Bacterial polysaccharides in sickness and in health. The 1995 Fleming Lecture. Microbiology 141 (Pt 9: 2023-2031.
26. Roberts I S (1996) The biochemistry and genetics of capsular polysaccharide production in bacteria. Annu Rev Microbiol 50: 285-315.
27. Buckles E L, Wang X, Lane M C, Lockatell C V, Johnson D E, et al. (2009) Role of the K2 capsule in *Escherichia coli* urinary tract infection and serum resistance. J Infect Dis 199: 1689-1697. doi:10.1086/598524.
28. Anderson G G, Goller C C, Justice S, Hultgren S J, Seed P C (2010) Polysaccharide Capsule and Sialic Acid-Mediated Regulation Promote Biofilm-like Intracellular Bacterial Communities During Cystitis. Infect Immun 78: 963-975. doi:IAI.00925-09 [pii] 10.1128/IAI.00925-09.
29. Mushtaq N, Redpath M B, Luzio J P, Taylor P W (2005) Treatment of experimental *Escherichia coli* infection with recombinant bacteriophage-derived capsule depolymerase. J Antimicrob Chemother 56: 160-165.
30. Llobet E, Tomas J M, Bengoechea J A (2008) Capsule polysaccharide is a bacterial decoy for antimicrobial peptides. Microbiology 154: 3877-3886. doi:154/12/3877 [pii] 10.1099/mic.0.2008/022301-0.
31. Varki A (2008) Sialic acids in human health and disease. Trends Mol Med 14: 351-360. doi:10.1016/j.molmed.2008.06.002.
32. Vimr E R, Steenbergen S M (2009) Early molecular-recognition events in the synthesis and export of group 2 capsular polysaccharides. Microbiology 155: 9-15. doi: 10.1099/mic.0.023564-0.
33. Rowe S, Hodson N, Griffiths G, Roberts I S (2000) Regulation of the *Escherichia coli* K5 capsule gene cluster: evidence for the roles of H—NS, BipA, and integration host factor in regulation of group 2 capsule gene clusters in pathogenic *E. coli*. J Bacteriol 182: 2741-2745.
34. Whitfield C, Roberts I S (1999) Structure, assembly and regulation of expression of capsules in *Escherichia coli*. Mol Microbiol 31: 1307-1319.
35. Stevens M P, Clarke B R, Roberts I S (1997) Regulation of the *Escherichia coli* K5 capsule gene cluster by transcription antitermination. Mol Microbiol 24: 1001-1012.
36. Goller C C, Seed P C (2010) High-Throughput Identification of Chemical Inhibitors of *E. coli* Group 2 Capsule Biogenesis as Anti-virulence Agents. PLoS One 5(7): e11642. doi:10.1371/journal.pone.0011642.
37. Sambrook Fritsch, E. F. and Maniatis, T. J (1989) Molecular Cloning: A Laboratory Manual. 2nd ed. Cold Spring Harbor, N.Y.: Cold Spring Harbor. p.
38. Molecular Libraries Program: Pathways to Discovery (2014). Available:http://mli.nih.gov/mli/compound-repository/mlsmr-compounds/.
39. Singh N, Guha R, Giulianotti M A, Pinilla C, Houghten R A, et al. (2009) Chemoinformatic analysis of combinatorial libraries, drugs, natural products, and molecular libraries small molecule repository. J Chem Inf Model 49: 1010-1024. doi:10.1021/ci800426u.
40. Scholl D, Merril C (2005) The genome of bacteriophage K1F, a T7-like phage that has acquired the ability to replicate on K1 strains of *Escherichia coli*. J Bacteriol 187: 8499-8503.
41. Scholl D, Adhya S, Merril C (2005) *Escherichia coli* K1's capsule is a barrier to bacteriophage T7. Appl Env Microbiol 71: 4872-4874.
42. Baell J B (2010) Observations on screening-based research and some concerning trends in the literature. Future Med Chem 2: 1529-1546. doi:10.4155/fmc.10.237.
43. Baell J B, Holloway G A (2010) New substructure filters for removal of pan assay interference compounds (PAINS) from screening libraries and for their exclusion in bioassays. J Med Chem 53: 2719-2740. doi:10.1021/jm901137j.
44. Noah J W, Severson W, Noah D L, Rasmussen L, White E L, et al. (2007) A cell-based luminescence assay is effective for high-throughput screening of potential influenza antivirals. Antiviral Res 73: 50-59. doi:10.1016/j.antiviral.2006.07.006.
45. YAMADA K (1963) Staining of sulphated polysaccharides by means of alcian blue. Nature 198: 799-800.
46. Johnson J R (1991) Virulence factors in *Escherichia coli* urinary tract infection. Clin Microbiol Rev 4: 80-128.
47. Noah J W, Anathan S, Evans C, Nebane M, Rasmussen L, et al. (2013) 3-(2,6-difluorobenzamido)-5-(4-ethoxyphenyl)thiophene-2-carboxylic acid inhibits *E. coli* UT189 bacterial capsule biogenesis.
48. Noah J W, Anathan S, Evans C, Nebane M, Rasmussen L, et al. (2013) N-(pyridin-4-yl)benzo[d]thiazole-6-carboxamide inhibits *E. coli* UT189 bacterial capsule biogenesis.
49. Mulvey M A, Lopez-Boado Y S, Wilson C L, Roth R, Parks W C, et al. (1998) Induction and evasion of host defenses by type 1-piliated uropathogenic *Escherichia coli*. Science (80-) 282: 1494-1497.
50. Roberts J A, Kaack M B, Baskin G, Marklund B I, Normark S (1997) Epitopes of the P-fimbrial adhesin of *E. coli* cause different urinary tract infections. J Urol 158: 1610-1613. doi:S0022-5347(01)64290-3 [pii].
51. Vimr E R, Troy F A (1985) Regulation of sialic acid metabolism in *Escherichia coli*: role of N-acylneuraminate pyruvate-lyase. J Bacteriol 164: 854-860.
52. Mobley H L, Jarvis K G, Elwood J P, Whittle D I, Lockatell C V, et al. (1993) Isogenic P-fimbrial deletion mutants of pyelonephritogenic *Escherichia coli*: the role of alpha Gal(1-4) beta Gal binding in virulence of a wild-type strain. Mol Microbiol 10: 143-155.
53. Hacker J, Bender L, Ott M, Wingender J, Lund B, et al. (1990) Deletions of chromosomal regions coding for fimbriae and hemolysins occur in vitro and in vivo in various extraintestinal *Escherichia coli* isolates. Microb Pathog 8: 213-225.
54. Serwer P (1974) Fast sedimenting bacteriophage T7 DNA from T7-infected *Escherichia coli*. Virology 59: 70-88.
55. Vimr E R, McCoy R D, Vollger H F, Wilkison N C, Troy F A (1984) Use of prokaryotic-derived probes to identify poly(sialic acid) in neonatal neuronal membranes. Proc Natl Acad Sci USA 81: 1971-1975.
56. Gupta D S, Jann B, Schmidt G, Golecki J R, Ãrskov I, et al. (1982) Coliphage K5, specific for *E. coli* exhibiting the capsular K5 antigen. FEMS Microbiol Lett 14: 75-78. doi:10.1111/j.1574-6968.1982.tb08638.x.

Background References

1. "Thiophene-2-carboxylic acid derivatives and their preparation and use for the treatment of flavivirus infections" Green, Jeremy; Wilson, Dean M.; Kong, Laval Chan Chun; Das, Sanjoy Kumar; Poisson, Carl; Court, John J.; Tang, Qing; Li, Pan; Collier, Philip N.; Waal, Nathan; et al, from PCT Int. Appl. (2012), WO 2012006055 A2 20120112

2. "Combining 3-D Quantitative Structure-Activity Relationship with Ligand Based and Structure Based Alignment Procedures for in Silico Screening of New Hepatitis C Virus NS5B Polymerase Inhibitors" Musmuca, Ira; Caroli, Antonia; Mai, Antonello; Kaushik-Basu, Neerja; Arora, Payal; Ragno, Rino, from Journal of Chemical Information and Modeling (2010), 50(4), 662-676.

3. "Preparation of carbonylaminothiophenecarboxylic acid derivatives for use as hepatitis C virus inhibitors" Harrison, David; Hartley, Charles David; Mordaunt, Jacqueline Elizabeth; Slater, Martin John, from PCT Int. Appl. (2008), WO 2009000818 A1 20081231

4. "Preparation of carboxythiophene derivatives for use as anti-viral agents" Harrison, David; Howes, Peter David; Mordaunt, Jacqueline Elizabeth; Shah, Pritom; Slater, Martin John, from PCT Int. Appl. (2008), WO 2008125599 A1 20081023

5. "Preparation of [(phenylcarbonyl)amino]arylthiophenecarboxylic acid derivatives for use as antiviral agents" Hartley, Charles David; Mordaunt, Jacqueline Elizabeth; Shah, Pritom; Slater, Martin John; White, Gemma Victoria, from PCT Int. Appl. (2008), WO 2008043791 A2 20080417

6. "Preparation of substituted (cyclohexylcarbonylamino) thiophenecarboxylic acids as antiviral agents for the treatment of hepatitis C infection" Corfield, John Andrew; Grimes, Richard Martin; Harrison, David; Hartley, Charles David; Howes, Peter David; Le, Joelle; Meeson, Malcolm Lees; Mordaunt, Jacqueline Elizabeth; Shah, Pritom; Slater, Martin John; et al, rom PCT Int. Appl. (2007), WO 2007071434 A1 20070628

7. "Crystal Structures of the RNA-dependent RNA Polymerase Genotype 2a of Hepatitis C Virus Reveal Two Conformations and Suggest Mechanisms of Inhibition by Non-nucleoside Inhibitors" By Biswal, Bichitra K.; Chemey, Maia M.; Wang, Meitian; Chan, Laval; Yannopoulos, Constantin G.; Bilimoria, Darius; Nicolas, Olivier; Bedard, Jean; James, Michael N. G., from Journal of Biological Chemistry (2005), 280(18), 18202-18210.

8. "Preparation of thiophenecarboxylates for the treatment or prevention of flavivirus infections" Chan Chun Kong, Laval; Das, Sanjoy Kumar; Nguyen-Ba, Nghe; Halab, Liliane; Hamelin, Bettina; Pereira, Oswy Z.; Poisson, Carl; Proulx, Melanie; Reddy, Thumkunta Jagadeeswar; Zhang, Ming-qiang, from PCT Int. Appl. (2004), WO 2004052885 A1 20040624

9. "Discovery of thiophene-2-carboxylic acids as potent inhibitors of HCV NS5B polymerase and HCV subgenomic RNA replication. Part 2: Tertiary amides" Chan, Laval; Pereira, Oswy; Reddy, T. Jagadeeswar; Das, Sanjoy K.; Poisson, Carl; Courchesne, Marc; Proulx, Melanie; Siddiqui, Arshad; Yannopoulos, Constantin G.; Nguyen-Ba, Nghe; et al, from Bioorganic & Medicinal Chemistry Letters (2004), 14(3), 797-800.

10. "Discovery of thiophene-2-carboxylic acids as potent inhibitors of HCV NS5B polymerase and HCV subgenomic RNA replication. Part 1: Sulfonamides" Chan, Laval; Das, Sanjoy K.; Reddy, T. Jagadeeswar; Poisson, Carl; Proulx, Melanie; Pereira, Oswy; Courchesne, Marc; Roy, Caroline; Wang, Wuyi; Siddiqui, Arshad; et al, from Bioorganic & Medicinal Chemistry Letters (2004), 14(3), 793-796.

11. "Preparation of thiophenecarboxylic acids and methods for the treatment or prevention of flaviviridae infections such as hepatitis C" Chan, Chun Kong Laval; Bedard, Jean; Das, Sanjoy Kumar; Nguyen Ba, Nghe; Pereira, Oswy Z.; Reddy, Thumkunta Jagadeeswar; Siddiqui, M. Arshad; Wang, Wuyi; Yannopoulos, Constantin, from PCT Int. Appl. (2002), WO 2002100851 A2 20021219

12. "Preparation of amino acid biaryl derivatives for the treatment or prevention of flavivirus infections" Chan, Chun Kong Laval; Bedard, Jean; Das, Sanjoy Kumar; Pereira, Oswy Z.; Shuttleworth, Steve; Siddiqui, M. Arshad; Wang, Wuyi, from PCT Int. Appl. (2002), WO 2002100846 A1 20021219

13. "3-Aminothiophene-2-carboxylic acids and their esters" No Inventor data available, from No Corporate Source data available (1960), GB 837086 19600609

It is to be understood that, while the invention has been described in conjunction with the detailed description, thereof, the foregoing description is intended to illustrate and not limit the scope of the invention. Other aspects, advantages, and modifications of the invention are within the scope of the claims set forth below. All publications, patents, and patent applications cited in this specification are herein incorporated by reference as if each individual publication or patent application were specifically and individually indicated to be incorporated by reference.

What is claimed is:

1. A method of inhibiting capsule biogenesis in a bacterium which comprises administering to the bacterium an effective amount of a composition comprising Compound 1

[chemical structure]

wherein $R^1$ is $C_{1-8}$ alkyl, $C_{1-8}$ alkoxy, $C_{1-8}$ haloalkoxy;

$R^2$ is hydrogen; and $R^3$ is substituted aryl or substituted furan group.

2. The method of claim 1, wherein the capsule biogenesis is K1 or K5 capsule biogenesis.

3. The method of claim 1, wherein the bacterium is a gram-negative bacteria.

4. The method of claim 3, wherein the gram-negative bacteria is *Campylobacter jejuni, Enterobacter cloacae, Escherichia Coli, Haemophilus influenzae, Klebsiella pneumoniae, Legionella pneumophila,* Methicillin-resistant *Staphylococcus aureus* (MRSA), *Neisseria meningitides, Proteus mirabilis, Pseudomonas aeruginosa, Salmonella typhimurium, Serratia marcescens, Staphylococcus aureus* or a combination thereof.

5. A method of treating a subject suffering from a bacterial infection comprising administering a therapeutically effective amount of a composition comprising

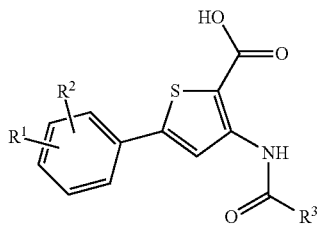

Compound 1 wherein $R^1$ is $C_{1-8}$ alkyl, $C_{1-8}$ alkoxy, $C_{1-8}$ haloalkoxy;
$R^2$ is hydrogen; and
$R^3$ is substituted furan group.

6. The method of claim 5, wherein the bacterium is a gram-negative bacteria.

7. The method of claim 6, wherein the gram-negative bacteria is *Campylobacter jejuni, Enterobacter cloacae, Escherichia Coli, Haemophilus influenzae, Klebsiella pneumoniae, Legionella pneumophila*, Methicillin-resistant *Staphylococcus aureus* (MRSA), *Neisseria meningitides, Proteus mirabilis, Pseudomonas aeruginosa, Salmonella typhimurium, Serratia marcescens, Staphylococcus aureus* or a combination thereof.

8. The method of claim 5, further comprising administering an agent that targets a bacterial cell wall.

9. The method of claim 8, wherein the agent is a penicillin or a cephalosporin.

10. The method of claim 5, wherein the bacterial infection is a urinary tract infection (UTI), or a disseminated *staphylococcus* infection.

11. The method of claim 10, wherein the bacterial infection is a urinary tract infection (UTI).

12. The method of claim 11 wherein the urinary tract infection (UTI) is a bladder infection.

13. The method of claim 11 wherein the urinary tract infection (UTI) is a kidney infection.

14. The method of claim 5, wherein the subject is a mammal.

15. The method of claim 14, wherein the mammal is a human.

16. The method of claim 1, wherein $R^1$ is a fluoro alkoxy group.

17. The method of claim 1, wherein $R^1$ is a methoxy, ethoxy, propoxy, or butoxy group.

18. The method of claim 1, wherein $R^3$ is a substituted aryl group with one or more fluoro substituents.

19. The method of claim 1, wherein $R^3$ is a bromo substituted furan group.

* * * * *